United States Patent
Rhode et al.

(10) Patent No.: US 12,325,734 B2
(45) Date of Patent: Jun. 10, 2025

(54) HUMAN IMMUNODEFICIENCY VIRUS-SPECIFIC T CELL RECEPTORS

(71) Applicants: ALTOR BIOSCIENCE, LLC, Miramar, FL (US); The USA, as represented by the Secretary, Department of Health and Human Services, Bethesda, MD (US)

(72) Inventors: Peter Rhode, Miami, FL (US); Mark Connors, Bethesda, MD (US); Stephen Migueles, Washington, DC (US)

(73) Assignees: Altor Bioscience LLC, Culver City, CA (US); The USA, as represented by the Secretary, Dept. of Health and Human Services, Bethesda, MD (US)

( * ) Notice: Subject to any disclaimer, the term of this patent is extended or adjusted under 35 U.S.C. 154(b) by 1002 days.

(21) Appl. No.: 17/422,523

(22) PCT Filed: Jan. 15, 2020

(86) PCT No.: PCT/US2020/013698
§ 371 (c)(1),
(2) Date: Jul. 13, 2021

(87) PCT Pub. No.: WO2020/150364
PCT Pub. Date: Jul. 23, 2020

(65) Prior Publication Data
US 2022/0098268 A1   Mar. 31, 2022

Related U.S. Application Data

(60) Provisional application No. 62/792,880, filed on Jan. 15, 2019.

(51) Int. Cl.
| | | |
|---|---|---|
| *A61P 31/18* | (2006.01) | |
| *A61K 38/00* | (2006.01) | |
| *A61K 40/10* | (2025.01) | |
| *A61K 40/11* | (2025.01) | |
| *A61K 40/32* | (2025.01) | |
| *A61K 40/46* | (2025.01) | |
| *C07K 14/725* | (2006.01) | |

(52) U.S. Cl.
CPC .......... *C07K 14/7051* (2013.01); *A61K 40/10* (2025.01); *A61K 40/11* (2025.01); *A61K 40/32* (2025.01); *A61K 40/46* (2025.01); *A61P 31/18* (2018.01); *A61K 38/00* (2013.01); *C07K 2319/02* (2013.01); *C07K 2319/03* (2013.01)

(58) Field of Classification Search
None
See application file for complete search history.

(56) References Cited

U.S. PATENT DOCUMENTS

| | | |
|---|---|---|
| 2014/0134128 A1 | 5/2014 | Wong et al. |
| 2015/0216937 A1 | 8/2015 | Wen et al. |
| 2016/0024174 A1 | 1/2016 | Odunsi et al. |
| 2017/0267737 A1 | 9/2017 | Protzer et al. |
| 2018/0085457 A1 | 3/2018 | Lu et al. |

FOREIGN PATENT DOCUMENTS

WO    WO 2018/157171    8/2018

OTHER PUBLICATIONS

Janeway, et. al, Immunobiology: The Immune System in Health and Disease, 5th ed., Garland Science, 2001 (Year: 2001).*
Sussman, et. al, Cell, 1988, 52, 85-95 (Year: 1988).*
Shah, et. al, Signal Transduction and Targeted Therapy, 2021, 6, 1-26 (Year: 2021).*
Card, et. al, Cancer Immunology, Immunotherapy, 2004, 53, 345-357 (Year: 2004).*
Harris, et. al, Trends Pharmacol Sci, 2016, 37, 220-230 (Year: 2016).*
Robinson, et. al, FEBS, 2021, 288, 6159-6173 (Year: 2021).*
Knies, et. al, Oncotarget, 2016, 16, 21999-21221 (Year: 2016).*
Zhang, et. al, Cancer Gene Therapy, 2004, 11, 487-496 (Year: 2004).*
Chung, et. al, PNAS, 1994, 91, 12654-12658 (Year: 1994).*
Mu, et. al, Frontiers in Cellular and Infection Microbiology, 2020, 10, 1-15 (Year: 2020).*
Huseby, et. al, Cell, 2005, 122, 247-260 (Year: 2005).*
Walseng, et. al, Sci Rep, 2017, 7, 1-10 (Year: 2017).*
Lonez, et. al, Cells, 2024, 13, 1-25 (Year: 2024).*
International Search Report and Written Opinion for International (PCT) Patent Application No. PCT/US2020/013698, dated Apr. 8, 2020 11 pages.
International Preliminary Report Patentability for International (PCT) Patent Application No. PCT/US2020/013698, dated Jul. 29, 2021 8 pages.

* cited by examiner

*Primary Examiner* — Misook Yu
*Assistant Examiner* — Samantha Lake Hopkins
(74) *Attorney, Agent, or Firm* — Sheridan Ross P.C.

(57) ABSTRACT

Engineered TCR molecules specific to retroviral peptide/HLA complexes guide direct killing and/or enable robust immune responses against HIV infected cells. In a first aspect, a TCR fusion polypeptide comprises a TCR variable alpha (Vα) domain, a TCR variable beta domain (Vβ) and a TCR constant region domain (C), wherein the TCR fusion polypeptide is specific for HIV peptides.

11 Claims, 24 Drawing Sheets

Specification includes a Sequence Listing.

scTCR

SEQUENCE LISTING

```
<160> NUMBER OF SEQ ID NOS: 28

<210> SEQ ID NO 1
<211> LENGTH: 1245
<212> TYPE: DNA
<213> ORGANISM: Homo sapiens

<400> SEQUENCE: 1
atggagacag acacactcct gttatgggta ctgttactct gggtgccagg tagtaccggt        60
agtcaacagg gagaagagga tcctcaggcc ttgagcatcc aggagggtga aaatgccacc       120
atgaactgca gttacaaaac tagtataaac aatttacagt ggtatagaca aaattcaggt       180
agaggccttg tccacctaat tttaatacgt tcaaatgaaa gagagaaaca cagtgggaga       240
```

```
ttaagagtca cgcttgacac ttccaagaaa agcagttcct tgttgatcac ggcttcccgg      300
gcagcagaca ctgcttctta cttctgtgct acggacgcta tcgacaagct catctttggg      360
actgggacca gattacaagt ctttccgact agtggaggag gtgggagcgg aggtggtgct      420
agcggtggcg gcggttctgg cggtggcggt cctcaagcg attctggagt cacacaaacc       480
ccaaagcacc tgatcacagc aactggacag cgagtgacgc tgagatgctc ccctaggtct      540
ggagacctct ctgtgtactg gtaccaacag agcctggacc agggcctcca gttcctcatt      600
cagtattata atggagaaga gagagcaaaa ggaaacattc ttgaacgatt ctccgcacaa      660
cagttccctg acttgcactc tgaactaaac ctgagctctc tggagctggg ggactcagct      720
ttgtatttct gtgccagcag cgtagttggg gacagccgag agacccagta cttcgggcca      780
ggcacgcggc tcctggtgct cgaggacctg aacaaggtgt tcccaccga ggtcgctgtg       840 tttgagccat cagaagcaga gatctcccac acccaaaagg ccacactggt gtgcctggcc      900
acaggcttct tccctgacca cgtggagctg agctggtggg tgaatgggaa ggaggtgcac      960
agtggggtca gcacggaccc gcagccctc aaggagcagc ccgccctcaa tgactccaga       1020
tactgcctga gcagccgcct gagggtctcg gccaccttct ggcagaaccc ccgcaaccac      1080
ttccgctgtc aagtccagtt ctacgggctc tcggagaatg acgagtggac ccaggatagg      1140
gccaaacccg tcacccagat cgtcagcgcc gaggcctggg gtagagcaga cgttaacggt      1200
ggtctgaacg acatcttcga agctcagaaa attgaatggc acgaa                     1245

<210> SEQ ID NO 2
<211> LENGTH: 415
<212> TYPE: PRT
<213> ORGANISM: Homo sapiens
<220> FEATURE:
<221> NAME/KEY: SIGNAL
<222> LOCATION: (1)..(20)
<220> FEATURE:
<221> NAME/KEY: SITE
<222> LOCATION: (48)..(51)
<223> OTHER INFORMATION: Complementarity determining region 1 (CDR1) V
      alpha
<220> FEATURE:
<221> NAME/KEY: SITE
<222> LOCATION: (70)..(75)
<223> OTHER INFORMATION: Complementarity determining region 2 (CDR2) V
      alpha
<220> FEATURE:
<221> NAME/KEY: SITE
<222> LOCATION: (110)..(118)
<223> OTHER INFORMATION: Complementarity determining region 3 (CDR3) V
      alpha
<220> FEATURE:
<221> NAME/KEY: DOMAIN
<222> LOCATION: (142)..(151)
<223> OTHER INFORMATION: Linker
<220> FEATURE:
<221> NAME/KEY: SITE
<222> LOCATION: (180)..(184)
<223> OTHER INFORMATION: CDR1 V beta
<220> FEATURE:
<221> NAME/KEY: SITE
<222> LOCATION: (202)..(207)
<223> OTHER INFORMATION: CDR2 V beta
<220> FEATURE:
<221> NAME/KEY: SITE
<222> LOCATION: (245)..(257)
<223> OTHER INFORMATION: CDR3 V beta
<220> FEATURE:
<221> NAME/KEY: DOMAIN
<222> LOCATION: (398)..(415)
<223> OTHER INFORMATION: BirA tag

<400> SEQUENCE: 2
```

-continued

```
Met Glu Thr Asp Thr Leu Leu Leu Trp Val Leu Leu Leu Trp Val Pro
1               5                   10                  15

Gly Ser Thr Gly Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Leu Leu Ile
                85                  90                  95

Thr Ala Ser Arg Ala Ala Asp Thr Ala Ser Tyr Phe Cys Ala Thr Asp
                100                 105                 110

Ala Ile Asp Lys Leu Ile Phe Gly Thr Gly Thr Arg Leu Gln Val Phe
            115                 120                 125

Pro Thr Ser Gly Gly Gly Ser Gly Gly Gly Ala Ser Gly Gly Gly
        130                 135                 140

Gly Ser Gly Gly Gly Ser Ser Ser Asp Ser Gly Val Thr Gln Thr
145                 150                 155                 160

Pro Lys His Leu Ile Thr Ala Thr Gly Gln Arg Val Thr Leu Arg Cys
                165                 170                 175

Ser Pro Arg Ser Gly Asp Leu Ser Val Tyr Trp Tyr Gln Gln Ser Leu
            180                 185                 190

Asp Gln Gly Leu Gln Phe Leu Ile Gln Tyr Tyr Asn Gly Glu Glu Arg
        195                 200                 205

Ala Lys Gly Asn Ile Leu Glu Arg Phe Ser Ala Gln Gln Phe Pro Asp
    210                 215                 220

Leu His Ser Glu Leu Asn Leu Ser Ser Leu Glu Leu Gly Asp Ser Ala
225                 230                 235                 240

Leu Tyr Phe Cys Ala Ser Ser Val Val Gly Asp Ser Arg Glu Thr Gln
                245                 250                 255

Tyr Phe Gly Pro Gly Thr Arg Leu Leu Val Leu Glu Asp Leu Asn Lys
            260                 265                 270

Val Phe Pro Pro Glu Val Ala Val Phe Glu Pro Ser Glu Ala Glu Ile
        275                 280                 285

Ser His Thr Gln Lys Ala Thr Leu Val Cys Leu Ala Thr Gly Phe Phe
    290                 295                 300

Pro Asp His Val Glu Leu Ser Trp Trp Val Asn Gly Lys Glu Val His
305                 310                 315                 320

Ser Gly Val Ser Thr Asp Pro Gln Pro Leu Lys Glu Gln Pro Ala Leu
                325                 330                 335

Asn Asp Ser Arg Tyr Cys Leu Ser Ser Arg Leu Arg Val Ser Ala Thr
            340                 345                 350

Phe Trp Gln Asn Pro Arg Asn His Phe Arg Cys Gln Val Gln Phe Tyr
        355                 360                 365

Gly Leu Ser Glu Asn Asp Glu Trp Thr Gln Asp Arg Ala Lys Pro Val
    370                 375                 380

Thr Gln Ile Val Ser Ala Glu Ala Trp Gly Arg Ala Asp Val Asn Gly
385                 390                 395                 400

Gly Leu Asn Asp Ile Phe Glu Ala Gln Lys Ile Glu Trp His Glu
                405                 410                 415
```

<210> SEQ ID NO 3
<211> LENGTH: 1272
<212> TYPE: DNA
<213> ORGANISM: Homo sapiens

<400> SEQUENCE: 3

| | | | | | |
|---|---|---|---|---|---|
| atggagacag | acacactcct | gttatgggta | ctgctgctct | gggttccagg | ttccaccggt | 60 |
| gctcagaagg | taactcaagc | gcagactgaa | atttctgtgg | tggagaagga | ggatgtgacc | 120 |
| ttggactgtg | tgtatgaaac | ccgtgatact | acttattact | tattctggta | caagcaacca | 180 |
| ccaagtggag | aattggtttt | cgttattcgt | cggaactctt | tgatgagca | aaatgaaata | 240 |
| agtggtcggt | attcttggaa | cttccagaaa | tccaccagtt | ccttcaactt | caccatcaca | 300 |
| gcctcacaag | tcgtggactc | agcagtatac | ttctgtgctc | tgaaaagcta | cgacagaggc | 360 |
| tcaaccctgg | ggaggctata | ctttggaaga | ggaactcagt | tgactgtctg | gcctactagt | 420 |
| ggaggaggtg | ggagcggagg | tggtgctagc | ggtggcggcg | ttctggcgg | tggcggttcc | 480 |
| tcaagcgaac | ctgaagtcac | ccagactccc | agccatcagg | tcacacagat | gggacaggaa | 540 |
| gtgatcttgc | gctgtgtccc | catctctaat | cacttatact | ctattggta | cagacaaatc | 600 |
| ttggggcaga | aagtcgagtt | tctggtttcc | ttttataata | atgaaatctc | agagaagtct | 660 |
| gaaatattcg | atgatcaatt | ctcagttgaa | aggcctgatg | gatcaaattt | cactctgaag | 720 |
| atccggtcca | caaagctgga | ggactcagcc | atgtacttct | gtgccagcag | tgaatggggc | 780 |
| gagaatgaaa | aactgttttt | tggcagtgga | acccagctct | ctgtcttgga | ggacctgaac | 840 |
| aaggtgttcc | cacccgaggt | cgctgtgttt | gagccatcag | aagcagagat | ctcccacacc | 900 |
| caaaaggcca | cactggtgtg | cctggccaca | ggcttcttcc | ctgaccacgt | ggagctgagc | 960 |
| tggtgggtga | tgggaagga | ggtgcacagt | ggggtcagca | cggacccgca | gcccctcaag | 1020 |
| gagcagcccg | ccctcaatga | ctccagatac | tgcctgagca | gccgcctgag | ggtctcggcc | 1080 |
| accttctggc | agaaccccg | caaccacttc | cgctgtcaag | tccagttcta | cgggctctcg | 1140 |
| gagaatgacg | agtggaccca | ggatagggcc | aaacccgtca | cccagatcgt | cagcgccgag | 1200 |
| gcctggggta | gagcagacgt | taacggtggt | ctgaacgaca | tcttcgaagc | tcagaaaatt | 1260 |
| gaatggcacg | aa | | | | | 1272 |

<210> SEQ ID NO 4
<211> LENGTH: 425
<212> TYPE: PRT
<213> ORGANISM: Homo sapiens
<220> FEATURE:
<221> NAME/KEY: SIGNAL
<222> LOCATION: (1)..(19)
<220> FEATURE:
<221> NAME/KEY: SITE
<222> LOCATION: (47)..(53)
<223> OTHER INFORMATION: CDR1 V alpha
<220> FEATURE:
<221> NAME/KEY: SITE
<222> LOCATION: (71)..(78)
<223> OTHER INFORMATION: CDR2 V alpha
<220> FEATURE:
<221> NAME/KEY: SITE
<222> LOCATION: (113)..(127)
<223> OTHER INFORMATION: CDR3 V alpha
<220> FEATURE:
<221> NAME/KEY: DOMAIN
<222> LOCATION: (141)..(161)
<223> OTHER INFORMATION: Linker
<220> FEATURE:
<221> NAME/KEY: SITE
<222> LOCATION: (190)..(194)

```
<223> OTHER INFORMATION: CDR1 V beta
<220> FEATURE:
<221> NAME/KEY: SITE
<222> LOCATION: (212)..(217)
<223> OTHER INFORMATION: CDR2 V beta
<220> FEATURE:
<221> NAME/KEY: SITE
<222> LOCATION: (256)..(267)
<223> OTHER INFORMATION: CDR3 V beta
<220> FEATURE:
<221> NAME/KEY: DOMAIN
<222> LOCATION: (408)..(425)
<223> OTHER INFORMATION: BirA tag

<400> SEQUENCE: 4

Met Glu Thr Asp Thr Leu Leu Leu Trp Val Leu Leu Leu Trp Val Pro
1               5                   10                  15

Gly Ser Thr Gly Ala Gln Lys Val Thr Gln Ala Gln Thr Glu Ile Ser
            20                  25                  30

Val Val Glu Lys Glu Asp Val Thr Leu Asp Cys Val Tyr Glu Thr Arg
        35                  40                  45

Asp Thr Thr Tyr Tyr Leu Phe Trp Tyr Lys Gln Pro Pro Ser Gly Glu
    50                  55                  60

Leu Val Phe Val Ile Arg Arg Asn Ser Phe Asp Glu Gln Asn Glu Ile
65                  70                  75                  80

Ser Gly Arg Tyr Ser Trp Asn Phe Gln Lys Ser Thr Ser Ser Phe Asn
                85                  90                  95

Phe Thr Ile Thr Ala Ser Gln Val Val Asp Ser Ala Val Tyr Phe Cys
            100                 105                 110

Ala Leu Lys Ser Tyr Asp Arg Gly Ser Thr Leu Gly Arg Leu Tyr Phe
            115                 120                 125

Gly Arg Gly Thr Gln Leu Thr Val Trp Pro Thr Ser Gly Gly Gly Gly
        130                 135                 140

Gly Ser Gly Gly Gly Ala Ser Gly Gly Gly Ser Gly Gly Gly Gly Gly
145                 150                 155                 160

Ser Ser Ser Glu Pro Glu Val Thr Gln Thr Pro Ser His Gln Val Thr
                165                 170                 175

Gln Met Gly Gln Glu Val Ile Leu Arg Cys Val Pro Ile Ser Asn His
            180                 185                 190

Leu Tyr Phe Tyr Trp Tyr Arg Gln Ile Leu Gly Gln Lys Val Glu Phe
            195                 200                 205

Leu Val Ser Phe Tyr Asn Asn Glu Ile Ser Glu Lys Ser Glu Ile Phe
            210                 215                 220

Asp Asp Gln Phe Ser Val Glu Arg Pro Asp Gly Ser Asn Phe Thr Leu
225                 230                 235                 240

Lys Ile Arg Ser Thr Lys Leu Glu Asp Ser Ala Met Tyr Phe Cys Ala
                245                 250                 255

Ser Ser Glu Trp Gly Glu Asn Glu Lys Leu Phe Phe Gly Ser Gly Thr
            260                 265                 270

Gln Leu Ser Val Leu Glu Asp Leu Asn Lys Val Phe Pro Pro Glu Val
            275                 280                 285

Ala Val Phe Glu Pro Ser Glu Ala Glu Ile Ser His Thr Gln Lys Ala
            290                 295                 300

Thr Leu Val Cys Leu Ala Thr Gly Phe Phe Pro Asp His Val Glu Leu
305                 310                 315                 320

Ser Trp Trp Val Asn Gly Lys Glu Val His Ser Gly Val Ser Thr Asp
                325                 330                 335
```

```
Pro Gln Pro Leu Lys Glu Gln Pro Ala Leu Asn Asp Ser Arg Tyr Cys
            340                 345                 350

Leu Ser Ser Arg Leu Arg Val Ser Ala Thr Phe Trp Gln Asn Pro Arg
        355                 360                 365

Asn His Phe Arg Cys Gln Val Gln Phe Tyr Gly Leu Ser Glu Asn Asp
    370                 375                 380

Glu Trp Thr Gln Asp Arg Ala Lys Pro Val Thr Gln Ile Val Ser Ala
385                 390                 395                 400

Glu Ala Trp Gly Arg Ala Asp Val Asn Gly Gly Leu Asn Asp Ile Phe
            405                 410                 415

Glu Ala Gln Lys Ile Glu Trp His Glu
            420                 425
```

```
<210> SEQ ID NO 5
<211> LENGTH: 1245
<212> TYPE: DNA
<213> ORGANISM: Homo sapiens

<400> SEQUENCE: 5
```

| | | | | | |
|---|---|---|---|---|---|
| atggagacag | acacactcct | gttatgggta | ctgctgctct | gggttccagg | ttccaccggt | 60 |
| agtcaacagg | agaagagga | tcctcaggcc | ttgagcatcc | aggagggtga | aaatgccacc | 120 |
| atgaactgca | gttacaaaac | tagtataaac | aatttacagt | ggtatagaca | aaattcaggt | 180 |
| agaggccttg | tccacctaat | tttaatacgt | tcaaatgaaa | agagagaaca | cagtggaaga | 240 |
| ttaagagtca | cgcttgacac | ttccaagaaa | agcagttcct | tgttgatcac | ggcttcccgg | 300 |
| gcagcagaca | ctgcttctta | cttctgtgct | acggacggca | aggcaggaac | tgctctgatc | 360 |
| tttgggaagg | gaaccacctt | atcagtgagt | tccactagtg | gaggaggtgg | gagcggaggt | 420 |
| ggtgctagcg | gtggcggcgg | ttctggcggt | ggcggttcct | caagcgaagc | ccaagtgacc | 480 |
| cagaacccaa | gataccctcat | cacagtgact | ggaaagaagt | taacagtgac | ttgttctcag | 540 |
| aatatgaacc | atgagtatat | gtcctggtat | cgacaagacc | cagggctggg | cttaaggcag | 600 |
| atctactatt | caatgaatgt | tgaggtgact | gataagggag | atgttcctga | agggtacaaa | 660 |
| gtctctcgaa | aagagaagag | gaatttcccc | ctgatcctgg | agtcgcccag | ccccaaccag | 720 |
| acctctctgt | acttctgtgc | cagcagtttg | gggaccttaa | gtgagcagtt | cttcgggcca | 780 |
| gggacacggc | tcaccgtgct | agaggacctg | aacaaggtgt | tcccacccga | ggtcgctgtg | 840 |
| tttgagccat | cagaagcaga | gatctcccac | acccaaaagg | ccacactggt | gtgcctggcc | 900 |
| acaggcttct | tccctgacca | cgtggagctg | agctggtggg | tgaatgggaa | ggaggtgcac | 960 |
| agtggggtca | gcacggaccc | gcagccccctc | aaggagcagc | ccgccctcaa | tgactccaga | 1020 |
| tactgcctga | gcagccgcct | gagggtctcg | gccaccttct | ggcagaaccc | ccgcaaccac | 1080 |
| ttccgctgtc | aagtccagtt | ctacgggctc | tcggagaatg | acgagtggac | ccaggatagg | 1140 |
| gccaaacccg | tcacccagat | cgtcagcgcc | gaggcctggg | gtagagcaga | cgttaacggt | 1200 |
| ggtctgaacg | acatcttcga | agctcagaaa | attgaatggc | acgaa | | 1245 |

```
<210> SEQ ID NO 6
<211> LENGTH: 415
<212> TYPE: PRT
<213> ORGANISM: Homo sapiens
<220> FEATURE:
<221> NAME/KEY: SIGNAL
<222> LOCATION: (1)..(20)
<220> FEATURE:
<221> NAME/KEY: SITE
<222> LOCATION: (47)..(51)
```

-continued

```
<223> OTHER INFORMATION: CDR1 V alpha
<220> FEATURE:
<221> NAME/KEY: SITE
<222> LOCATION: (69)..(75)
<223> OTHER INFORMATION: CDR2 V alpha
<220> FEATURE:
<221> NAME/KEY: SITE
<222> LOCATION: (110)..(120)
<223> OTHER INFORMATION: CDR3 V alpha
<220> FEATURE:
<221> NAME/KEY: DOMAIN
<222> LOCATION: (134)..(153)
<223> OTHER INFORMATION: Linker
<220> FEATURE:
<221> NAME/KEY: SITE
<222> LOCATION: (182)..(186)
<223> OTHER INFORMATION: CDR1 V beta
<220> FEATURE:
<221> NAME/KEY: SITE
<222> LOCATION: (204)..(209)
<223> OTHER INFORMATION: CDR2 V beta
<220> FEATURE:
<221> NAME/KEY: SITE
<222> LOCATION: (247)..(257)
<223> OTHER INFORMATION: CDR3 V beta
<220> FEATURE:
<221> NAME/KEY: DOMAIN
<222> LOCATION: (398)..(415)
<223> OTHER INFORMATION: BirA tag

<400> SEQUENCE: 6

Met Glu Thr Asp Thr Leu Leu Leu Trp Val Leu Leu Trp Val Pro
1               5                   10                  15

Gly Ser Thr Gly Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Ser Leu Leu Ile
                85                  90                  95

Thr Ala Ser Arg Ala Ala Asp Thr Ala Ser Tyr Phe Cys Ala Thr Asp
            100                 105                 110

Gly Lys Ala Gly Thr Ala Leu Ile Phe Gly Lys Gly Thr Thr Leu Ser
        115                 120                 125

Val Ser Ser Thr Ser Gly Gly Gly Ser Gly Gly Ala Ser Gly
    130                 135                 140

Gly Gly Gly Ser Gly Gly Gly Ser Ser Glu Ala Gln Val Thr
145                 150                 155                 160

Gln Asn Pro Arg Tyr Leu Ile Thr Val Thr Gly Lys Lys Leu Thr Val
                165                 170                 175

Thr Cys Ser Gln Asn Met Asn His Glu Tyr Met Ser Trp Tyr Arg Gln
            180                 185                 190

Asp Pro Gly Leu Gly Leu Arg Gln Ile Tyr Tyr Ser Met Asn Val Glu
        195                 200                 205

Val Thr Asp Lys Gly Asp Val Pro Glu Gly Tyr Lys Val Ser Arg Lys
    210                 215                 220

Glu Lys Arg Asn Phe Pro Leu Ile Leu Glu Ser Pro Ser Pro Asn Gln
225                 230                 235                 240

Thr Ser Leu Tyr Phe Cys Ala Ser Ser Leu Gly Thr Leu Ser Glu Gln
                245                 250                 255
```

```
Phe Phe Gly Pro Gly Thr Arg Leu Thr Val Leu Glu Asp Leu Asn Lys
            260                 265                 270

Val Phe Pro Pro Glu Val Ala Val Phe Glu Pro Ser Glu Ala Glu Ile
        275                 280                 285

Ser His Thr Gln Lys Ala Thr Leu Val Cys Leu Ala Thr Gly Phe Phe
    290                 295                 300

Pro Asp His Val Glu Leu Ser Trp Trp Val Asn Gly Lys Glu Val His
305                 310                 315                 320

Ser Gly Val Ser Thr Asp Pro Gln Pro Leu Lys Glu Gln Pro Ala Leu
                325                 330                 335

Asn Asp Ser Arg Tyr Cys Leu Ser Arg Leu Arg Val Ser Ala Thr
            340                 345                 350

Phe Trp Gln Asn Pro Arg Asn His Phe Arg Cys Gln Val Gln Phe Tyr
        355                 360                 365

Gly Leu Ser Glu Asn Asp Glu Trp Thr Gln Asp Arg Ala Lys Pro Val
    370                 375                 380

Thr Gln Ile Val Ser Ala Glu Ala Trp Gly Arg Ala Asp Val Asn Gly
385                 390                 395                 400

Gly Leu Asn Asp Ile Phe Glu Ala Gln Lys Ile Glu Trp His Glu
                405                 410                 415

<210> SEQ ID NO 7
<211> LENGTH: 1263
<212> TYPE: DNA
<213> ORGANISM: Homo sapiens

<400> SEQUENCE: 7
atggagacag acacactcct gttatgggta ctgctgctct gggttccagg ttccaccggt      60
cagaaggagg tggagcagaa ttctggaccc ctcagtgttc cagagggagc cattgcctct     120
ctcaactgca cttacagtga ccgaggttcc agtccttct tctggtacag acaatattct      180
gggaaaagcc ctgagttgat aatgtccata tactccaatg gtgacaaaga agatggaagg     240
tttacagcac agctcaataa agccagccag tatgttttctc tgctcatcag agactcccag     300
cccagtgatt cagccaccta cctctgtgcc gtgagaattc agggagccca gaagctggta     360
tttggccaag gaaccaggct gactatcaac ccaactagtg gaggaggtgg gagcggaggt     420
ggtgctagcg gtggcggcgg ttctggcggt ggcggttcct caagcgatgc tggaatcacc     480
cagagcccaa gacacaaggt cacagagaca ggaacaccag tgactctgag atgtcaccag     540
actgagaacc accgctacat gtactggtat cgacaagacc cggggcatgg gctgaggcta     600
atccattact catatggtgt taaagatact gacaaaggag aagtctcaga tggctatagt     660
gtctctagat caaagacaga ggatttcctc ctcactctgg agtccgctac cagctcccag     720
acatctgtgt acttctgtgc catcagtgag tcggcaggga atcgggtag cacggcctac     780 gagcagtact cgggccgggg caccaggctc acggtcacag gaggacctga acaaggtgttc     840 ccacccgagg tcgctgtgtt tgagccatca gaagcagaga tctcccacac ccaaaaggcc     900
acactggtgt gcctggccac aggcttcttc cctgaccacg tggagctgag ctggtgggtg     960
aatgggaagg aggtgcacag tggggtcagc acggaccccgc agcccctcaa ggagcagccc    1020
gccctcaatg actccagata ctgcctgagc agccgcctga gggtctcggc caccttctgg    1080 cagaacccc gcaaccactt ccgctgtcaa gtccagttct acgggctctc ggagaatgac    1140
gagtggaccc aggatagggc caaacccgtc acccagatcg tcagcgccga ggcctgggt    1200
```

```
agagcagacg ttaacggtgg tctgaacgac atcttcgaag ctcagaaaat tgaatggcac    1260
gaa                                                                 1263
```

<210> SEQ ID NO 8
<211> LENGTH: 421
<212> TYPE: PRT
<213> ORGANISM: Homo sapiens
<220> FEATURE:
<221> NAME/KEY: SIGNAL
<222> LOCATION: (1)..(20)
<220> FEATURE:
<221> NAME/KEY: SITE
<222> LOCATION: (47)..(52)
<223> OTHER INFORMATION: CDR1 V alpha
<220> FEATURE:
<221> NAME/KEY: SITE
<222> LOCATION: (70)..(75)
<223> OTHER INFORMATION: CDR2 V alpha
<220> FEATURE:
<221> NAME/KEY: SITE
<222> LOCATION: (110)..(120)
<223> OTHER INFORMATION: CDR3 V alpha
<220> FEATURE:
<221> NAME/KEY: DOMAIN
<222> LOCATION: (134)..(153)
<223> OTHER INFORMATION: Linker
<220> FEATURE:
<221> NAME/KEY: SITE
<222> LOCATION: (182)..(187)
<223> OTHER INFORMATION: CDR1 V beta
<220> FEATURE:
<221> NAME/KEY: SITE
<222> LOCATION: (204)..(209)
<223> OTHER INFORMATION: CDR2 V beta
<220> FEATURE:
<221> NAME/KEY: SITE
<222> LOCATION: (247)..(264)
<223> OTHER INFORMATION: CDR3 V beta
<220> FEATURE:
<221> NAME/KEY: DOMAIN
<222> LOCATION: (404)..(421)

<400> SEQUENCE: 8

```
Met Glu Thr Asp Thr Leu Leu Leu Trp Val Leu Leu Leu Trp Val Pro
 1               5                  10                  15

Gly Ser Thr Gly Gln Lys Glu Val Glu Gln Asn Ser Gly Pro Leu Ser
            20                  25                  30

Val Pro Glu Gly Ala Ile Ala Ser Leu Asn Cys Thr Tyr Ser Asp Arg
        35                  40                  45

Gly Ser Gln Ser Phe Phe Trp Tyr Arg Gln Tyr Ser Gly Lys Ser Pro
    50                  55                  60

Glu Leu Ile Met Ser Ile Tyr Ser Asn Gly Asp Lys Glu Asp Gly Arg
65                  70                  75                  80

Phe Thr Ala Gln Leu Asn Lys Ala Ser Gln Tyr Val Ser Leu Leu Ile
                85                  90                  95

Arg Asp Ser Gln Pro Ser Asp Ser Ala Thr Tyr Leu Cys Ala Val Arg
            100                 105                 110

Ile Gln Gly Ala Gln Lys Leu Val Phe Gly Gln Gly Thr Arg Leu Thr
        115                 120                 125

Ile Asn Pro Thr Ser Gly Gly Gly Ser Gly Gly Ala Ser Gly
    130                 135                 140

Gly Gly Gly Ser Gly Gly Gly Ser Ser Asp Ala Gly Ile Thr
145                 150                 155                 160

Gln Ser Pro Arg His Lys Val Thr Glu Thr Gly Thr Pro Val Thr Leu
                165                 170                 175
```

```
Arg Cys His Gln Thr Glu Asn His Arg Tyr Met Tyr Trp Tyr Arg Gln
            180                 185                 190

Asp Pro Gly His Gly Leu Arg Leu Ile His Tyr Ser Tyr Gly Val Lys
        195                 200                 205

Asp Thr Asp Lys Gly Glu Val Ser Asp Gly Tyr Ser Val Ser Arg Ser
210                 215                 220

Lys Thr Glu Asp Phe Leu Leu Thr Leu Glu Ser Ala Thr Ser Ser Gln
225                 230                 235                 240

Thr Ser Val Tyr Phe Cys Ala Ile Ser Glu Ser Ala Gly Lys Ser Gly
                245                 250                 255

Ser Thr Ala Tyr Glu Gln Tyr Phe Gly Pro Gly Thr Arg Leu Thr Val
            260                 265                 270

Thr Glu Asp Leu Asn Lys Val Phe Pro Pro Glu Val Ala Val Phe Glu
        275                 280                 285

Pro Ser Glu Ala Glu Ile Ser His Thr Gln Lys Ala Thr Leu Val Cys
290                 295                 300

Leu Ala Thr Gly Phe Phe Pro Asp His Val Glu Leu Ser Trp Trp Val
305                 310                 315                 320

Asn Gly Lys Glu Val His Ser Gly Val Ser Thr Asp Pro Gln Pro Leu
                325                 330                 335

Lys Glu Gln Pro Ala Leu Asn Asp Ser Arg Tyr Cys Leu Ser Ser Arg
            340                 345                 350

Leu Arg Val Ser Ala Thr Phe Trp Gln Asn Pro Arg Asn His Phe Arg
        355                 360                 365

Cys Gln Val Gln Phe Tyr Gly Leu Ser Glu Asn Asp Glu Trp Thr Gln
370                 375                 380

Asp Arg Ala Lys Pro Val Thr Gln Ile Val Ser Ala Glu Ala Trp Gly
385                 390                 395                 400

Arg Ala Asp Val Asn Gly Gly Leu Asn Asp Ile Phe Glu Ala Gln Lys
                405                 410                 415

Ile Glu Trp His Glu
            420

<210> SEQ ID NO 9
<211> LENGTH: 1251
<212> TYPE: DNA
<213> ORGANISM: Homo sapiens

<400> SEQUENCE: 9
atggagacag acacactcct gttatgggta ctgctgctct gggttccagg ttccaccggt     60
ggagattcag tgacccagat ggaagggcca gtgactctct cagaagaggc cttcctgact    120
ataaactgca cgtacacagc cacaggatac ccttcccttt tctggtatgt ccaatatcct    180
ggagaaggtc tacagctcct cctgaaagcc acgaaggctg atgacaaggg aagcaacaaa    240
ggttttgaag ccatataccg taagaaaacc acttcttttc cacttggaga aaggctcagtt   300 caagtgtcag actcagcggt gtacttctgt gcttccgtct atgggaacaa cagactcgct    360
tttgggaagg ggaaccaagt ggtggtcata ccaactagtg aggaggtgga gcggaggt      420 ggtgctagcg gtggcggcgg ttctggcggt ggcggttcct caagcgatgt gaaagtaacc    480
cagagctcga gatatctagt caaaaggacg ggagagaaag ttttctggaa atgtgtccag    540
gatatggacc atgaaaatat gttctggtat cgacaagacc aggtctgggc tacggctg     600 atctatttct catatgatgt taaaatgaaa gaaaaggag atattcctga gggtatcagt     660
gtctctagag agaagaagga gcacttctcc ctgattctgg agtccgccag caccaaccag    720
```

```
acatctatgt acctctgtgc cagcagtttg ggctcgggga gcacagatac gcagtatttt    780
ggcccaggca cccggctgac agtgctcgag gacctgaaca aggtgttccc acccgaggtc    840
gctgtgtttg agccatcaga agcagagatc tcccacaccc aaaaggccac actggtgtgc    900
ctggccacag gcttcttccc tgaccacgtg agctgagct ggtgggtgaa tgggaaggag     960
gtgcacagtg gggtcagcac ggacccgcag cccctcaagg agcagcccgc cctcaatgac   1020
tccagatact gcctgagcag ccgcctgagg gtctcggcca ccttctggca gaaccccgc    1080 aaccacttcc gctgtcaagt ccagttctac gggctctcgg agaatgacga gtggacccag   1140
gatagggcca aacccgtcac ccagatcgtc agcgccgagg cctggggtag agcagacgtt   1200
aacggtggtc tgaacgacat cttcgaagct cagaaaattg aatggcacga a            1251
```

```
<210> SEQ ID NO 10
<211> LENGTH: 417
<212> TYPE: PRT
<213> ORGANISM: Homo sapiens
<220> FEATURE:
<221> NAME/KEY: SIGNAL
<222> LOCATION: (1)..(20)
<220> FEATURE:
<221> NAME/KEY: SITE
<222> LOCATION: (47)..(52)
<223> OTHER INFORMATION: CDR1 V alpha
<220> FEATURE:
<221> NAME/KEY: SITE
<222> LOCATION: (70)..(76)
<223> OTHER INFORMATION: CDR2 V alpha
<220> FEATURE:
<221> NAME/KEY: SITE
<222> LOCATION: (111)..(120)
<223> OTHER INFORMATION: CDR3 V alpha
<220> FEATURE:
<221> NAME/KEY: DOMAIN
<222> LOCATION: (134)..(153)
<223> OTHER INFORMATION: Linker
<220> FEATURE:
<221> NAME/KEY: SITE
<222> LOCATION: (182)..(186)
<223> OTHER INFORMATION: CDR1 V beta
<220> FEATURE:
<221> NAME/KEY: SITE
<222> LOCATION: (204)..(209)
<223> OTHER INFORMATION: CDR2 V beta
<220> FEATURE:
<221> NAME/KEY: SITE
<222> LOCATION: (247)..(260)
<223> OTHER INFORMATION: CDR3 V beta
<220> FEATURE:
<221> NAME/KEY: DOMAIN
<222> LOCATION: (400)..(417)
<223> OTHER INFORMATION: BirA tag

<400> SEQUENCE: 10

Met Glu Thr Asp Thr Leu Leu Leu Trp Val Leu Leu Trp Val Pro
1               5                   10                  15

Gly Ser Thr Gly Gly Asp Ser Val Thr Gln Met Glu Gly Pro Val Thr
            20                  25                  30

Leu Ser Glu Glu Ala Phe Leu Thr Ile Asn Cys Thr Tyr Thr Ala Thr
        35                  40                  45

Gly Tyr Pro Ser Leu Phe Trp Tyr Val Gln Tyr Pro Gly Glu Gly Leu
    50                  55                  60

Gln Leu Leu Leu Lys Ala Thr Lys Ala Asp Asp Lys Gly Ser Asn Lys
65                  70                  75                  80

Gly Phe Glu Ala Thr Tyr Arg Lys Glu Thr Thr Ser Phe His Leu Glu
                85                  90                  95
```

Lys Gly Ser Val Gln Val Ser Asp Ser Ala Val Tyr Phe Cys Ala Ser
                100                 105                 110

Val Tyr Gly Asn Asn Arg Leu Ala Phe Gly Lys Gly Asn Gln Val Val
            115                 120                 125

Val Ile Pro Thr Ser Gly Gly Gly Ser Gly Gly Ala Ser Gly
130                 135                 140

Gly Gly Ser Gly Gly Gly Ser Ser Asp Val Lys Val Thr
145                 150                 155                 160

Gln Ser Ser Arg Tyr Leu Val Lys Arg Thr Gly Glu Lys Val Phe Leu
                165                 170                 175

Glu Cys Val Gln Asp Met Asp His Glu Asn Met Phe Trp Tyr Arg Gln
            180                 185                 190

Asp Pro Gly Leu Gly Leu Arg Leu Ile Tyr Phe Ser Tyr Asp Val Lys
        195                 200                 205

Met Lys Glu Lys Gly Asp Ile Pro Glu Gly Tyr Ser Val Ser Arg Glu
    210                 215                 220

Lys Lys Glu His Phe Ser Leu Ile Leu Glu Ser Ala Ser Thr Asn Gln
225                 230                 235                 240

Thr Ser Met Tyr Leu Cys Ala Ser Ser Leu Gly Ser Gly Ser Thr Asp
                245                 250                 255

Thr Gln Tyr Phe Gly Pro Gly Thr Arg Leu Thr Val Leu Glu Asp Leu
            260                 265                 270

Asn Lys Val Phe Pro Pro Glu Val Ala Val Phe Glu Pro Ser Glu Ala
        275                 280                 285

Glu Ile Ser His Thr Gln Lys Ala Thr Leu Val Cys Leu Ala Thr Gly
    290                 295                 300

Phe Phe Pro Asp His Val Glu Leu Ser Trp Trp Val Asn Gly Lys Glu
305                 310                 315                 320

Val His Ser Gly Val Ser Thr Asp Pro Gln Pro Leu Lys Glu Gln Pro
                325                 330                 335

Ala Leu Asn Asp Ser Arg Tyr Cys Leu Ser Ser Arg Leu Arg Val Ser
            340                 345                 350

Ala Thr Phe Trp Gln Asn Pro Arg Asn His Phe Arg Cys Gln Val Gln
        355                 360                 365

Phe Tyr Gly Leu Ser Glu Asn Asp Glu Trp Thr Gln Asp Arg Ala Lys
    370                 375                 380

Pro Val Thr Gln Ile Val Ser Ala Glu Ala Trp Gly Arg Ala Asp Val
385                 390                 395                 400

Asn Gly Gly Leu Asn Asp Ile Phe Glu Ala Gln Lys Ile Glu Trp His
                405                 410                 415

Glu

<210> SEQ ID NO 11
<211> LENGTH: 1251
<212> TYPE: DNA
<213> ORGANISM: Homo sapiens

<400> SEQUENCE: 11
atggagacag acacactact gttatgggta ctgctgctct gggttccagg ttccaccggt    60
ggagagagtg tggggctgca tcttcctacc ctgagtgtcc aggagggtga caactctatt    120
atcaactgtg cttattcaaa cagcgcctca gactacttca tttggtacaa gcaagaatct    180
ggaaaaggtc tcaattcat tatagacatt cgttcaaata tggacaaaag gcaaggccaa    240

```
agagtcaccg tttttattgaa taagacagtg aaacatctct ctctgcaaat tgcagctact    300
caacctggag actcagctgt ctacttttgt gcagagagcg ggtactatgg tcagaatttt    360
gtctttggtc ccggaaccag attgtcagtg ctgccgacta gtggaggagg tgggagcgga    420
ggtggtgcta gcggtggcgg cggctctggc ggtggcggtt cctcaagcga agcccaagtg    480
acccagaacc caagatacct catcacagtg actggaaaga agttgacagt gacttgttct    540
cagaatatga accatgagta tatgtcctgg tatcgacaag acccagggct gggcttaagg    600
cagatctact attcaatgaa tgttgaggtg actgataagg gagatgttcc tgaagggtac    660
aaagtctctc gaaaagagaa gaggaatttc cccctgatcc tggagtcgcc cagccccaac    720
cagacctctc tgtacttctg tgccagcaga cccggacagg gaggctacga gcagtacttc    780
gggccgggca ccaggctcac ggtcacagag gacctgaaaa acgtgttccc acccgaggtc    840
gctgtgtttg agccatcaga agcagagatc tcccacaccc aaaaggccac actggtgtgc    900
ctggccacag gcttcttccc tgaccacgtg agctgagct ggtgggttaa cgggaaggag    960
gtgcacagtg gggtcagcac ggacccgcag ccctcaagg agcagcccgc cctcaatgac   1020
tccagatact gcctgagcag ccgcctgagg gtctcggcca ccttctggca gaaccccgc    1080 aaccacttcc gctgtcaagt ccagttctac gggctctcgg agaatgacga gtggaccag    1140 gatagggcca aacccgtcac ccagatcgtc agcgccgagg cctggggtag agcagacgtt   1200
aacggtggtc tgaacgacat cttcgaagct cagaaaattg aatggcacga a          1251
```

```
<210> SEQ ID NO 12
<211> LENGTH: 417
<212> TYPE: PRT
<213> ORGANISM: Homo sapiens
<220> FEATURE:
<221> NAME/KEY: SIGNAL
<222> LOCATION: (1)..(20)
<220> FEATURE:
<221> NAME/KEY: SITE
<222> LOCATION: (47)..(52)
<223> OTHER INFORMATION: CDR1 V alpha
<220> FEATURE:
<221> NAME/KEY: SITE
<222> LOCATION: (70)..(76)
<223> OTHER INFORMATION: CDR2 V alpha
<220> FEATURE:
<221> NAME/KEY: SITE
<222> LOCATION: (111)..(120)
<223> OTHER INFORMATION: CDR3 V alpha
<220> FEATURE:
<221> NAME/KEY: DOMAIN
<222> LOCATION: (135)..(154)
<223> OTHER INFORMATION: Linker
<220> FEATURE:
<221> NAME/KEY: SITE
<222> LOCATION: (183)..(187)
<223> OTHER INFORMATION: CDR1 V beta
<220> FEATURE:
<221> NAME/KEY: SITE
<222> LOCATION: (205)..(210)
<223> OTHER INFORMATION: CDR2 V beta
<220> FEATURE:
<221> NAME/KEY: SITE
<222> LOCATION: (248)..(260)
<223> OTHER INFORMATION: CDR3 V beta
<220> FEATURE:
<221> NAME/KEY: DOMAIN
<222> LOCATION: (400)..(417)
<223> OTHER INFORMATION: BirA tag

<400> SEQUENCE: 12

Met Glu Thr Asp Thr Leu Leu Leu Trp Val Leu Leu Leu Trp Val Pro
1               5                   10                  15
```

```
Gly Ser Thr Gly Gly Glu Ser Val Gly Leu His Leu Pro Thr Leu Ser
            20                  25                  30

Val Gln Glu Gly Asp Asn Ser Ile Ile Asn Cys Ala Tyr Ser Asn Ser
        35                  40                  45

Ala Ser Asp Tyr Phe Ile Trp Tyr Lys Gln Ser Gly Lys Gly Pro
50                  55                  60

Gln Phe Ile Ile Asp Ile Arg Ser Asn Met Asp Lys Arg Gln Gly Gln
65                  70                  75                  80

Arg Val Thr Val Leu Leu Asn Lys Thr Val Lys His Leu Ser Leu Gln
                85                  90                  95

Ile Ala Ala Thr Gln Pro Gly Asp Ser Ala Val Tyr Phe Cys Ala Glu
            100                 105                 110

Ser Gly Tyr Tyr Gly Gln Asn Phe Val Phe Gly Pro Gly Thr Arg Leu
        115                 120                 125

Ser Val Leu Pro Thr Ser Gly Gly Gly Ser Gly Gly Gly Ala Ser
130                 135                 140

Gly Gly Gly Gly Ser Gly Gly Gly Ser Ser Glu Ala Gln Val
145                 150                 155                 160

Thr Gln Asn Pro Arg Tyr Leu Ile Thr Val Thr Gly Lys Lys Leu Thr
                165                 170                 175

Val Thr Cys Ser Gln Asn Met Asn His Glu Tyr Met Ser Trp Tyr Arg
            180                 185                 190

Gln Asp Pro Gly Leu Gly Leu Arg Gln Ile Tyr Tyr Ser Met Asn Val
        195                 200                 205

Glu Val Thr Asp Lys Gly Asp Val Pro Glu Gly Tyr Lys Val Ser Arg
    210                 215                 220

Lys Glu Lys Arg Asn Phe Pro Leu Ile Leu Glu Ser Pro Ser Pro Asn
225                 230                 235                 240

Gln Thr Ser Leu Tyr Phe Cys Ala Ser Arg Pro Gly Gln Gly Gly Tyr
                245                 250                 255

Glu Gln Tyr Phe Gly Pro Gly Thr Arg Leu Thr Val Thr Glu Asp Leu
            260                 265                 270

Lys Asn Val Phe Pro Pro Glu Val Ala Val Phe Glu Pro Ser Glu Ala
        275                 280                 285

Glu Ile Ser His Thr Gln Lys Ala Thr Leu Val Cys Leu Ala Thr Gly
    290                 295                 300

Phe Phe Pro Asp His Val Glu Leu Ser Trp Trp Val Asn Gly Lys Glu
305                 310                 315                 320

Val His Ser Gly Val Ser Thr Asp Pro Gln Pro Leu Lys Glu Gln Pro
                325                 330                 335

Ala Leu Asn Asp Ser Arg Tyr Cys Leu Ser Ser Arg Leu Arg Val Ser
            340                 345                 350

Ala Thr Phe Trp Gln Asn Pro Arg Asn His Phe Arg Cys Gln Val Gln
        355                 360                 365

Phe Tyr Gly Leu Ser Glu Asn Asp Glu Trp Thr Gln Asp Arg Ala Lys
    370                 375                 380

Pro Val Thr Gln Ile Val Ser Ala Glu Ala Trp Gly Arg Ala Asp Val
385                 390                 395                 400

Asn Gly Gly Leu Asn Asp Ile Phe Glu Ala Gln Lys Ile Glu Trp His
                405                 410                 415

Glu
```

<210> SEQ ID NO 13
<211> LENGTH: 1257
<212> TYPE: DNA
<213> ORGANISM: Homo sapiens

<400> SEQUENCE: 13

```
atggagacag acacactcct gttatgggta ctgctgctct gggttccagg ttccaccggt      60
gcccagaaga taactcaaac ccaaccagga atgttcgtgc aggaaaagga ggctgtgact     120
ctggactgca catatgacac cagtgatcaa agttatggtc tattctggta caagcagccc     180
agcagtgggg aaatgatttt tcttatttat caggggtctt atgacgagca aaatgcaaca     240
gaaggtcgct actcattgaa tttccagaag gcaagaaaat ccgccaacct tgtcatctcc     300
gcttcacaac tgggggactc agcaatgtat ttctgtgcaa tgagagatgg cggaacctcc     360
tacgacaagg tgatatttgg gccagggaca agcttatcag tcattccaac tagtggagga     420
ggtgggagcg gaggtggtgc tagcggtggc ggcggttctg gcggtggcgg ttcctcaagc     480
gaagcccaag tgaccagaa cccaagatac ctcatcacag tgactggaaa gaagttaaca     540
gtgacttgtt ctcagaatat gaaccatgag tatatgtcct ggtatcgaca agacccaggg     600
ctgggcttaa ggcagatcta ctattcaatg aatgttgagg tgactgataa gggagatgtt     660
cctgaagggt acaaagtctc tcgaaaagag aagaggaatt cccccctgat cctggagtcg     720
cccagcccca accagacctc tctgtacttc tgtgccagca gcgtcatat ggatacgcag     780
tattttggcc caggcacccg gctgacagtg ctcgaggacc tgaacaaggt gttcccaccc     840
gaggtcgctg tgtttgagcc atcagaagca gagatctccc acacccaaaa ggccacactg     900
gtgtgcctgg ccacaggctt cttccctgac cacgtggagc tgagctggtg ggtgaatggg     960
aaggaggtgc acagtggggt cagcacggac ccgcagcccc tcaaggagca gcccgccctc    1020
aatgactcca gatactgcct gagcagccgc ctgagggtct cggccacctt ctggcagaac    1080
ccccgcaacc acttccgctg tcaagtccag ttctacgggc tctcggagaa tgacgagtgg    1140
acccaggata gggccaaacc cgtcacccag atcgtcagcg ccgaggcctg ggtagagca     1200
gacgttaacg gtggtctgaa cgacatcttc gaagctcaga aaattgaatg gcacgaa       1257
```

<210> SEQ ID NO 14
<211> LENGTH: 419
<212> TYPE: PRT
<213> ORGANISM: Homo sapiens
<220> FEATURE:
<221> NAME/KEY: SIGNAL
<222> LOCATION: (1)..(20)
<220> FEATURE:
<221> NAME/KEY: SITE
<222> LOCATION: (47)..(53)
<223> OTHER INFORMATION: CDR1 V alpha
<220> FEATURE:
<221> NAME/KEY: SITE
<222> LOCATION: (71)..(78)
<223> OTHER INFORMATION: CDR2 V alpha
<220> FEATURE:
<221> NAME/KEY: SITE
<222> LOCATION: (113)..(125)
<223> OTHER INFORMATION: CDR3 V alpha
<220> FEATURE:
<221> NAME/KEY: DOMAIN
<222> LOCATION: (139)..(158)
<223> OTHER INFORMATION: Linker
<220> FEATURE:
<221> NAME/KEY: SITE
<222> LOCATION: (187)..(191)
<223> OTHER INFORMATION: CDR1 V beta
<220> FEATURE:
<221> NAME/KEY: SITE -continued

```
<222> LOCATION: (209)..(214)
<223> OTHER INFORMATION: CDR2 V beta
<220> FEATURE:
<221> NAME/KEY: SITE
<222> LOCATION: (252)..(261)
<223> OTHER INFORMATION: CDR3 V beta
<220> FEATURE:
<221> NAME/KEY: DOMAIN
<222> LOCATION: (402)..(419)
<223> OTHER INFORMATION: BirA tag

<400> SEQUENCE: 14
```

Met Glu Thr Asp Thr Leu Leu Leu Trp Val Leu Leu Leu Trp Val Pro
1               5                   10                  15

Gly Ser Thr Gly Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Gln Ser Tyr Gly Leu Phe Trp Tyr Lys Gln Pro Ser Ser Gly Glu
    50                  55                  60

Met Ile Phe Leu Ile Tyr Gln Gly Ser Tyr Asp Glu Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Arg Asp Gly Gly Thr Ser Tyr Asp Lys Val Ile Phe Gly Pro
        115                 120                 125

Gly Thr Ser Leu Ser Val Ile Pro Thr Ser Gly Gly Gly Ser Gly
    130                 135                 140

Gly Gly Ala Ser Gly Gly Gly Ser Gly Gly Gly Gly Ser Ser
145                 150                 155                 160

Glu Ala Gln Val Thr Gln Asn Pro Arg Tyr Leu Ile Thr Val Thr Gly
                165                 170                 175

Lys Lys Leu Thr Val Thr Cys Ser Gln Asn Met Asn His Glu Tyr Met
            180                 185                 190

Ser Trp Tyr Arg Gln Asp Pro Gly Leu Gly Leu Arg Gln Ile Tyr Tyr
        195                 200                 205

Ser Met Asn Val Glu Val Thr Asp Lys Gly Asp Val Pro Glu Gly Tyr
    210                 215                 220

Lys Val Ser Arg Lys Glu Lys Arg Asn Phe Pro Leu Ile Leu Glu Ser
225                 230                 235                 240

Pro Ser Pro Asn Gln Thr Ser Leu Tyr Phe Cys Ala Ser Ser Gly His
                245                 250                 255

Met Asp Thr Gln Tyr Phe Gly Pro Gly Thr Arg Leu Thr Val Leu Glu
            260                 265                 270

Asp Leu Asn Lys Val Phe Pro Pro Glu Val Ala Val Phe Glu Pro Ser
        275                 280                 285

Glu Ala Glu Ile Ser His Thr Gln Lys Ala Thr Leu Val Cys Leu Ala
    290                 295                 300

Thr Gly Phe Phe Pro Asp His Val Glu Leu Ser Trp Trp Val Asn Gly
305                 310                 315                 320

Lys Glu Val His Ser Gly Val Ser Thr Asp Pro Gln Pro Leu Lys Glu
                325                 330                 335

Gln Pro Ala Leu Asn Asp Ser Arg Tyr Cys Leu Ser Ser Arg Leu Arg
            340                 345                 350

```
Val Ser Ala Thr Phe Trp Gln Asn Pro Arg Asn His Phe Arg Cys Gln
        355                 360                 365

Val Gln Phe Tyr Gly Leu Ser Glu Asn Asp Glu Trp Thr Gln Asp Arg
    370                 375                 380

Ala Lys Pro Val Thr Gln Ile Val Ser Ala Glu Ala Trp Gly Arg Ala
385                 390                 395                 400

Asp Val Asn Gly Gly Leu Asn Asp Ile Phe Glu Ala Gln Lys Ile Glu
                405                 410                 415

Trp His Glu

<210> SEQ ID NO 15
<211> LENGTH: 1254
<212> TYPE: DNA
<213> ORGANISM: Homo sapiens

<400> SEQUENCE: 15
```

| | | | | | |
|---|---|---|---|---|---|
| atggagacag | acacactcct | gttatgggta | ctgctgctct | gggttccagg | ttccaccggt | 60 |
| atactgatca | agcaatgctg | gtgtcactca | gaccccaaaa | ttccgcatcc | tgaagatagg | 120 |
| acagagcatg | acactgcagt | gtacccagga | tatgaaccat | aactacatgt | actggtatcg | 180 |
| acaagaccca | ggcatggggc | tgaagctgat | ttattattca | gttggtgctg | gtatcactga | 240 |
| taaaggagaa | gtcccgaatg | ctacaacgt | ctccagatca | accacagagg | attttccgct | 300 |
| caggctggag | ttggctgctc | cctcccagac | atctgtgtac | ttctgtgcca | gcacccgggg | 360 |
| ccgaggtggg | acccagtact | tcgggccagg | cacgcggctc | ctggtgctcg | aggacctgaa | 420 |
| caaggtgttc | ccacccgagg | tcgctgtgtt | tgagccatca | gaagcagaga | tctcccacac | 480 |
| ccaaaaggcc | acactggtgt | gcctggccac | aggcttcttc | cctgaccacg | tggagctgag | 540 |
| ctggtgggtg | aatgggaagg | aggtgcacag | tggggtcagc | acggaccgc | agcccctcaa | 600 |
| ggagcagccc | gcctcaatg | actccagata | ctgcctgagc | agccgcctga | ggtctcggc | 660 |
| caccttctgg | cagaaccccc | gcaaccactt | ccgctgtcaa | gtccagttct | acgggctctc | 720 |
| ggagaatgac | gagtggaccc | aggataggc | caaacccgtc | acccagatcg | tcagcgccga | 780 |
| ggcctggggt | agagcagaca | cgtggaacaa | agtcctcagt | cactgcatgt | tcaggaggga | 840 |
| gacagcacca | atttcacctg | cagcttccct | tccagcaatt | tttatgcctt | acactggtac | 900 |
| agatgggaaa | ctgcaaaaag | ccccgaggcc | ttgtttgtaa | tgactttaaa | tggggatgaa | 960 |
| aagaagaaag | gacgaataag | tgccactctt | aataccaagg | agggttacag | ctatttgtac | 1020 |
| atcaaaggat | cccagcctga | agactcagcc | acatacctct | gtgcctcctg | ggataactat | 1080 |
| ggtcagaatt | ttgtctttgg | tcccggaacc | agattgtccg | tgctgcccac | tagtggagga | 1140 |
| ggaggaagcg | gaggtggtgc | tagcggtggc | ggcggttctg | gcggtggcgg | ttccgttaac | 1200 |
| atcgatggcg | gtctgaacga | catcttcgaa | gctcagaaaa | tagaatggca | cgaa | 1254 |

```
<210> SEQ ID NO 16
<211> LENGTH: 418
<212> TYPE: PRT
<213> ORGANISM: Homo sapiens
<220> FEATURE:
<221> NAME/KEY: SIGNAL
<222> LOCATION: (1)..(20)
<220> FEATURE:
<221> NAME/KEY: SITE
<222> LOCATION: (47)..(52)
<223> OTHER INFORMATION: CDR1 V alpha
<220> FEATURE:
<221> NAME/KEY: SITE
<222> LOCATION: (70)..(76)
```

-continued

```
<223> OTHER INFORMATION: CDR2 V alpha
<220> FEATURE:
<221> NAME/KEY: SITE
<222> LOCATION: (111)..(121)
<223> OTHER INFORMATION: CDR3 V alpha
<220> FEATURE:
<221> NAME/KEY: DOMAIN
<222> LOCATION: (135)..(154)
<223> OTHER INFORMATION: Linker
<220> FEATURE:
<221> NAME/KEY: SITE
<222> LOCATION: (183)..(187)
<223> OTHER INFORMATION: CDR1 V beta
<220> FEATURE:
<221> NAME/KEY: SITE
<222> LOCATION: (205)..(210)
<223> OTHER INFORMATION: CDR2 V beta
<220> FEATURE:
<221> NAME/KEY: SITE
<222> LOCATION: (248)..(258)
<223> OTHER INFORMATION: CDR3 V beta
<220> FEATURE:
<221> NAME/KEY: DOMAIN
<222> LOCATION: (399)..(418)
<223> OTHER INFORMATION: BirA tag

<400> SEQUENCE: 16

Met Glu Thr Asp Thr Leu Leu Leu Trp Val Leu Leu Trp Val Pro
1               5                   10                  15

Gly Ser Thr Gly Ile Leu Asn Val Glu Gln Ser Pro Gln Ser Leu His
            20                  25                  30

Val Gln Glu Gly Asp Ser Thr Asn Phe Thr Cys Ser Phe Pro Ser Ser
        35                  40                  45

Asn Phe Tyr Ala Leu His Trp Tyr Arg Trp Glu Thr Ala Lys Ser Pro
    50                  55                  60

Glu Ala Leu Phe Val Met Thr Leu Asn Gly Asp Glu Lys Lys Lys Gly
65                  70                  75                  80

Arg Ile Ser Ala Thr Leu Asn Thr Lys Glu Gly Tyr Ser Tyr Leu Tyr
                85                  90                  95

Ile Lys Gly Ser Gln Pro Glu Asp Ser Ala Thr Tyr Leu Cys Ala Ser
            100                 105                 110

Trp Asp Asn Tyr Gly Gln Asn Phe Val Phe Gly Pro Gly Thr Arg Leu
        115                 120                 125

Ser Val Leu Pro Thr Ser Gly Gly Gly Ser Gly Gly Gly Ala Ser
    130                 135                 140

Gly Gly Gly Gly Ser Gly Gly Gly Ser Ser Asn Ala Gly Val
145                 150                 155                 160

Thr Gln Thr Pro Lys Phe Arg Ile Leu Lys Ile Gly Gln Ser Met Thr
                165                 170                 175

Leu Gln Cys Thr Gln Asp Met Asn His Asn Tyr Met Tyr Trp Tyr Arg
            180                 185                 190

Gln Asp Pro Gly Met Gly Leu Lys Leu Ile Tyr Tyr Ser Val Gly Ala
        195                 200                 205

Gly Ile Thr Asp Lys Gly Glu Val Pro Asn Gly Tyr Asn Val Ser Arg
    210                 215                 220

Ser Thr Thr Glu Asp Phe Pro Leu Arg Leu Glu Leu Ala Ala Pro Ser
225                 230                 235                 240

Gln Thr Ser Val Tyr Phe Cys Ala Ser Thr Arg Gly Arg Gly Thr
                245                 250                 255

Gln Tyr Phe Gly Pro Gly Thr Arg Leu Leu Val Leu Glu Asp Leu Asn
            260                 265                 270
```

```
Lys Val Phe Pro Pro Glu Val Ala Val Phe Pro Ser Glu Ala Glu
            275                 280                 285

Ile Ser His Thr Gln Lys Ala Thr Leu Val Cys Leu Ala Thr Gly Phe
        290                 295                 300

Phe Pro Asp His Val Glu Leu Ser Trp Trp Val Asn Gly Lys Glu Val
305                 310                 315                 320

His Ser Gly Val Ser Thr Asp Pro Gln Pro Leu Lys Glu Gln Pro Ala
                325                 330                 335

Leu Asn Asp Ser Arg Tyr Cys Leu Ser Ser Arg Leu Arg Val Ser Ala
            340                 345                 350

Thr Phe Trp Gln Asn Pro Arg Asn His Phe Arg Cys Gln Val Gln Phe
        355                 360                 365

Tyr Gly Leu Ser Glu Asn Asp Glu Trp Thr Gln Asp Arg Ala Lys Pro
    370                 375                 380

Val Thr Gln Ile Val Ser Ala Glu Ala Trp Gly Arg Ala Asp Val Asn
385                 390                 395                 400

Ile Asp Gly Gly Leu Asn Asp Ile Phe Glu Ala Gln Lys Ile Glu Trp
                405                 410                 415

His Glu

<210> SEQ ID NO 17
<211> LENGTH: 1266
<212> TYPE: DNA
<213> ORGANISM: Homo sapiens

<400> SEQUENCE: 17
atggagacag acacactcct gttatgggta ctgctgctct gggttccagg ttccaccggt      60
gagctgaaag tggaacaaaa ccctctgttc ctgagcatgc aggagggaaa aaactatacc     120
atctactgca attattcaac cacttcagac agactgtatt ggtacaggca ggatcctggg     180
aaaagtctgg aatctctgtt tgtgttgcta tcaaatggag cagtgaagca gagggacga     240 ttaatggcct cacttgatac caaagcccgt ctcagcaccc tccacatcac agctgccgtg     300
catgacctct ctgccaccta cttctgtgcc gtggacgaag gtggggagc ccagaagctg      360 gtatttggcc aaggaaccag gctgactatc aatccgacta gtggaggagg tgggagcgga     420
ggtggtgcta gcggtggcgg cggttctggc ggtggcggtt cctcaagcga cactgaagtt     480
acccagacac aaaacacct ggtcatggga atgacaaata gaagtctttt gaatgtgaa      540 caacatatgg ggcacagggc tatgtattgg tacaagcaga aagctaagaa gccaccggag     600
ctcatgtttg tctacagcta tgagaaactc tctataaatg aaagtgtgcc aagtcgcttc     660
tcacctgaat gccccaacag ctctctctta aaccttcacc tacacgccct gcagccagaa     720
gactcagccc tgtatctctg cgccagcagc catcctttta gcggatctag cacagatacg     780
cagtattttg gcccaggcac ccggctgaca gtgctcgagg acctgaaaaa cgtgttccca     840
cccgaggtcg ctgtgtttga gccatcagaa gcagagatct cccacaccca aaaggccaca     900
ctggtgtgcc tggccacagg cttcttccct gaccacgtgg agctgagctg gtgggtgaat     960
gggaaggagg tgcacagtgg ggtcagcacg gaccgcagc ccctcaagga gcagcccgcc    1020
ctcaatgact ccagatactg cctgagcagc cgcctgaggg tctcggccac cttctggcag    1080 aaccccgca accacttccg ctgtcaagtc cagttctacg gctctcggga gaatgacgag    1140
tggacccagg atagggccaa acccgtcacc cagatcgtca gcgccgaggc tggggtaga    1200 gcagacgtta acatcgatgg cggtctgaac gacatcttcg aagctcagaa aatagaatgg    1260
``` cacgaa                                                                  1266

<210> SEQ ID NO 18
<211> LENGTH: 422
<212> TYPE: PRT
<213> ORGANISM: Homo sapiens
<220> FEATURE:
<221> NAME/KEY: SIGNAL
<222> LOCATION: (1)..(20)
<220> FEATURE:
<221> NAME/KEY: SITE
<222> LOCATION: (47)..(51)
<223> OTHER INFORMATION: CDR1 V alpha
<220> FEATURE:
<221> NAME/KEY: SITE
<222> LOCATION: (69)..(75)
<223> OTHER INFORMATION: CDR2 V alpha
<220> FEATURE:
<221> NAME/KEY: SITE
<222> LOCATION: (110)..(121)
<223> OTHER INFORMATION: CDR3 V alpha
<220> FEATURE:
<221> NAME/KEY: DOMAIN
<222> LOCATION: (135)..(154)
<223> OTHER INFORMATION: Linker
<220> FEATURE:
<221> NAME/KEY: SITE
<222> LOCATION: (183)..(187)
<223> OTHER INFORMATION: CDR1 V beta
<220> FEATURE:
<221> NAME/KEY: SITE
<222> LOCATION: (205)..(210)
<223> OTHER INFORMATION: CDR2 V beta
<220> FEATURE:
<221> NAME/KEY: SITE
<222> LOCATION: (248)..(262)
<223> OTHER INFORMATION: CDR3 V beta
<220> FEATURE:
<221> NAME/KEY: DOMAIN
<222> LOCATION: (403)..(422)
<223> OTHER INFORMATION: BirA tag

<400> SEQUENCE: 18

Met Glu Thr Asp Thr Leu Leu Leu Trp Val Leu Leu Leu Trp Val Pro
1               5                   10                  15

Gly Ser Thr Gly Glu Leu Lys Val Glu Gln Asn Pro Leu Phe Leu Ser
            20                  25                  30

Met Gln Glu Gly Lys Asn Tyr Thr Ile Tyr Cys Asn Tyr Ser Thr Thr
        35                  40                  45

Ser Asp Arg Leu Tyr Trp Tyr Arg Gln Asp Pro Gly Lys Ser Leu Glu
    50                  55                  60

Ser Leu Phe Val Leu Leu Ser Asn Gly Ala Val Lys Gln Glu Gly Arg
65                  70                  75                  80

Leu Met Ala Ser Leu Asp Thr Lys Ala Arg Leu Ser Thr Leu His Ile
                85                  90                  95

Thr Ala Ala Val His Asp Leu Ser Ala Thr Tyr Phe Cys Ala Val Asp
            100                 105                 110

Glu Gly Trp Gly Ala Gln Lys Leu Val Phe Gly Gln Gly Thr Arg Leu
        115                 120                 125

Thr Ile Asn Pro Thr Ser Gly Gly Gly Ser Gly Gly Gly Ala Ser
    130                 135                 140

Gly Gly Gly Gly Ser Gly Gly Gly Gly Ser Ser Asp Thr Glu Val
145                 150                 155                 160

Thr Gln Thr Pro Lys His Leu Val Met Gly Met Thr Asn Lys Lys Ser
                165                 170                 175

Leu Lys Cys Glu Gln His Met Gly His Arg Ala Met Tyr Trp Tyr Lys

```
                    180                 185                 190
Gln Lys Ala Lys Lys Pro Pro Glu Leu Met Phe Val Tyr Ser Tyr Glu
            195                 200                 205

Lys Leu Ser Ile Asn Glu Ser Val Pro Ser Arg Phe Ser Pro Glu Cys
    210                 215                 220

Pro Asn Ser Ser Leu Leu Asn Leu His Leu His Ala Leu Gln Pro Glu
225                 230                 235                 240

Asp Ser Ala Leu Tyr Leu Cys Ala Ser Ser His Pro Phe Ser Gly Ser
                245                 250                 255

Ser Thr Asp Thr Gln Tyr Phe Gly Pro Gly Thr Arg Leu Thr Val Leu
            260                 265                 270

Glu Asp Leu Lys Asn Val Phe Pro Pro Glu Val Ala Val Phe Glu Pro
        275                 280                 285

Ser Glu Ala Glu Ile Ser His Thr Gln Lys Ala Thr Leu Val Cys Leu
    290                 295                 300

Ala Thr Gly Phe Phe Pro Asp His Val Glu Leu Ser Trp Trp Val Asn
305                 310                 315                 320

Gly Lys Glu Val His Ser Gly Val Ser Thr Asp Pro Gln Pro Leu Lys
                325                 330                 335

Glu Gln Pro Ala Leu Asn Asp Ser Arg Tyr Cys Leu Ser Ser Arg Leu
            340                 345                 350

Arg Val Ser Ala Thr Phe Trp Gln Asn Pro Arg Asn His Phe Arg Cys
        355                 360                 365

Gln Val Gln Phe Tyr Gly Leu Ser Glu Asn Asp Glu Trp Thr Gln Asp
    370                 375                 380

Arg Ala Lys Pro Val Thr Gln Ile Val Ser Ala Glu Ala Trp Gly Arg
385                 390                 395                 400

Ala Asp Val Asn Ile Asp Gly Gly Leu Asn Asp Ile Phe Glu Ala Gln
                405                 410                 415

Lys Ile Glu Trp His Glu
            420

<210> SEQ ID NO 19
<211> LENGTH: 9
<212> TYPE: PRT
<213> ORGANISM: Human immunodeficiency virus type 1

<400> SEQUENCE: 19

Arg Leu Arg Pro Gly Gly Lys Lys Lys
1               5

<210> SEQ ID NO 20
<211> LENGTH: 10
<212> TYPE: PRT
<213> ORGANISM: Human immunodeficiency virus type 1

<400> SEQUENCE: 20

Arg Tyr Pro Leu Thr Phe Gly Trp Cys Phe
1               5                   10

<210> SEQ ID NO 21
<211> LENGTH: 8
<212> TYPE: PRT
<213> ORGANISM: Human immunodeficiency virus type 1

<400> SEQUENCE: 21

Glu Ile Tyr Lys Arg Trp Ile Ile
1               5
```

```
<210> SEQ ID NO 22
<211> LENGTH: 8
<212> TYPE: PRT
<213> ORGANISM: Human immunodeficiency virus type 1

<400> SEQUENCE: 22

Phe Leu Lys Glu Lys Gly Gly Leu
1               5

<210> SEQ ID NO 23
<211> LENGTH: 9
<212> TYPE: PRT
<213> ORGANISM: Human immunodeficiency virus type 1

<400> SEQUENCE: 23

Asp Arg Phe Tyr Lys Thr Leu Arg Ala
1               5

<210> SEQ ID NO 24
<211> LENGTH: 10
<212> TYPE: PRT
<213> ORGANISM: Human immunodeficiency virus type 1

<400> SEQUENCE: 24

Lys Arg Trp Ile Ile Leu Gly Leu Asn Lys
1               5                   10

<210> SEQ ID NO 25
<211> LENGTH: 11
<212> TYPE: PRT
<213> ORGANISM: Human immunodeficiency virus type 1

<400> SEQUENCE: 25

Arg Pro Gln Val Pro Leu Arg Pro Met Thr Tyr
1               5                   10

<210> SEQ ID NO 26
<211> LENGTH: 11
<212> TYPE: PRT
<213> ORGANISM: Human immunodeficiency virus type 1

<400> SEQUENCE: 26

Lys Ala Phe Ser Pro Glu Val Ile Pro Met Phe
1               5                   10

<210> SEQ ID NO 27
<211> LENGTH: 9
<212> TYPE: PRT
<213> ORGANISM: Human immunodeficiency virus type 1

<400> SEQUENCE: 27

Ile Ser Pro Arg Thr Leu Asn Ala Trp
1               5

<210> SEQ ID NO 28
<211> LENGTH: 9
<212> TYPE: PRT
<213> ORGANISM: Human immunodeficiency virus type 1

<400> SEQUENCE: 28

Gln Ala Ser Gln Glu Val Lys Asn Trp
1               5
```

HUMAN IMMUNODEFICIENCY VIRUS-SPECIFIC T CELL RECEPTORS

CROSS REFERENCE TO RELATED APPLICATIONS

This application is a national stage application under 35 U.S.C. 371 and claims the benefit of PCT Application No. PCT/US2020/013698 having an international filing date of 15 Jan. 2020, which designated the United States, which PCT application claimed the benefit of U.S. Provisional Application No. 62/792,880, filed 15 Jan. 2019, the disclosures of each of which are incorporated herein by reference in their entireties.

GOVERNMENT INTEREST

This invention was made with government support by scientists working for the National Institutes of Health. The government has certain rights in the invention.

REFERENCE TO A SEQUENCE LISTING

This application contains references to amino acid sequences and/or nucleic acid sequences which have been submitted concurrently herewith as the sequence listing text file entitled "48277-539P01PCT ST25.TXT", file size 55,434 bytes, created on 8 Jan. 2020. The aforementioned sequence listing is hereby incorporated by reference in its entirety pursuant to 37 C.F.R. § 1.52 (e) (5).

FIELD

Embodiments of the invention are directed to T cell receptor (TCR) molecules specific for retrovirus peptide/human leukocyte antigen (HLA) complexes. In particular, the retrovirus is human immunodeficiency virus (HIV).

BACKGROUND

HIV infection remains a major public health problem, affecting more than 35 million people worldwide and more than 1.2 million people in the United States. Combined antiretroviral therapy (cART) can achieve a "functional cure," but HIV resurgence in latently infected cells after cART withdrawal is a main obstacle to a permanent cure of HIV infection. Current cART does not eliminate integrated and transcriptionally silent HIV-1 provirus in latently infected cells. While combined antiretroviral therapy (cART) has greatly improved survival rates among AIDS patients, many HIV infected individuals develop AIDS when latently infected cells reactivate. Reactivation can result from non-adherence to medication and from drug-resistant virus emergence. Moreover, HIV+ long term survivors continue to develop comorbidities, including an accelerated aging process, neurocognitive disorders, heart failure, and others. Current antiretroviral therapy does not eliminate the integrated and transcriptionally silent HIV provirus in latently infected cells.

SUMMARY

There is a need in the art for therapeutic approaches to target retroviruses specifically. Accordingly, engineered TCR molecules are disclosed herein, specific for HIV peptide/HLA complexes. These TCRs guide direct killing and/or enable robust immune responses against virally infected cells. In certain embodiments, the TCRs embodied herein are soluble TCRs.

In certain embodiments, TCR molecules specifically recognize HIV peptide antigens, which were known to be presented in the context of HLA molecules on antigen presenting cells and/or CD4 T cells during infection.

In a first aspect, a TCR fusion polypeptide comprises a TCR variable alpha (Vα) domain, a TCR variable beta domain (Vβ) and a TCR constant region domain (C), wherein the TCR fusion polypeptide is specific for HIV peptides. The TCR fusion polypeptide further comprises a linker molecule linking the Vα and the Vβ domains. In certain embodiments, the TCR polypeptide is a single chain fragment, such as, a single chain variable fragment (scFv). In certain embodiments, the TCR polypeptide is HLA class I or class II-restricted. In certain embodiments, the TCR is HLA class I-restricted. In certain embodiments, the TCR fusion polypeptide is HLA-A, HLA-B or HLA-C restricted. In certain embodiments, the TCR polypeptide specifically binds one or more of HIV Gag, Pol, Nef, or combinations thereof. In certain embodiments the TCR fusion polypeptide comprises at least a 50% sequence identity to any one of SEQ ID NOs: 2, 4, 6, 8, 10, 12, 14, 16, or 18. In certain embodiments, the TCR fusion polypeptide comprises any one of SEQ ID NOs: 2, 4, 6, 8, 10, 12, 14, 16, or 18.

In certain embodiments, the TCR fusion polypeptide further comprises immune signaling domains, transmembrane domains, cytoplasmic domains, biologically active domains, or combinations thereof. In certain embodiments, the biologically active domains comprise: cytokines, monokines, checkpoint inhibitors, antigen specific antibody domains, enzymes, or combinations thereof.

In a second aspect, the TCR fusion polypeptide is multimeric.

In a third aspect, a nucleic acid polynucleotide sequence encoding a TCR fusion polypeptide is provided, comprising a TCR Vα domain, a TCR Vβ domain, and a TCR C domain, wherein the TCR fusion polypeptide is specific for HIV peptides. In certain embodiments, the nucleic acid polynucleotide sequence comprises a nucleic sequence encoding a linker molecule linking the Vα and the Vβ domains. In certain embodiments, the encoded TCR is HLA class I or class II-restricted. In certain embodiments, the encoded TCR is HLA class I-restricted, such as, HLA-A, HLA-B or HLA-C restricted. In certain embodiments, the nucleic acid polynucleotide sequence further comprises nucleic acid sequences encoding immune signaling domains, transmembrane domains, cytoplasmic domains, biologically active domains, or combinations thereof. Examples of biologically active domains include cytokines, checkpoint inhibitors, antigen specific antibody domains, enzymes, or combinations thereof. In certain embodiments, the TCR nucleic acid polynucleotide sequence comprises at least a 90% sequence identity to any one of SEQ ID NOs: 1, 3, 5, 7, 9, 11, 13, 15, or 17. In certain embodiments, the TCR nucleic acid polynucleotide sequence comprises any one of SEQ ID NOs: 1, 3, 5, 7, 9, 11, 13, 15, or 17.

In a fourth aspect, a TCR fusion polypeptide comprises a TCR Vα domain, a TCR domain, a TCR C domain, and an immune effector domain, wherein the TCR fusion polypeptide is specific for HIV peptides. In certain embodiments, the TCR fusion polypeptide further comprises a linker molecule linking the Vα and the Vβ domains. In certain embodiments, the TCR is HLA class I or class II-restricted. In certain embodiments, the TCR is HLA class I-restricted. In certain embodiments, the TCR fusion polypeptide specifically binds to HIV Gag, Pol, Nef, or combinations thereof. In certain embodiments, the immune effector domains comprise CD3 or CD28 signaling domains. In certain embodiments, the TCR fusion polypeptide is soluble or membrane bound. In certain embodiments, the membrane bound TCR fusion polypeptide comprises transmembrane domains, cytoplasmic domain, biologically active domains, or combinations thereof. The biologically active domains, include, without limitation: cytokines, checkpoint inhibitors, antigen specific antibody domains, enzymes, or combinations thereof.

In some embodiments, the intracellular signaling domain is or includes a primary signaling domain, a signaling domain capable of inducing a primary activation signal in a T cell. The intracellular signaling domain may include an intracellular signaling domain of a CD3 chain, optionally a CD3-zeta (CD3ζ) chain, or a signaling portion thereof. In some embodiments, the intracellular signaling domain further includes a second signaling domain. In some embodiments, the second signaling domain is a costimulatory signaling domain that may include an intracellular signaling domain of a CD28, or a signaling portion thereof.

In a fifth aspect, an isolated cell comprises any one or more TCR polypeptides, or nucleic acid polynucleotide sequences encoding a TCR fusion polypeptides as described herein. In certain embodiments, the isolated cell is an autologous cell, allogeneic cell, haplotype matched cell, haplotype mismatched cell, haplo-identical cell, xenogeneic cell, stem cell, a cell line, or combinations thereof. In certain embodiments, the isolated cell is a T cell. In certain embodiments, the T cell is a CD4$^+$ T cell, a CD8$^+$ T cell, or a combination thereof. In certain embodiments, the isolated T cell is modified to express an HLA-restricted HIV-specific antigen binding polypeptide, comprising: an antigen specific binding domain, a transmembrane domain, and an intracellular signaling region, the signaling region comprising a primary signaling domain, optionally derived from a CD3 chain domain, and a second signaling domain which is a costimulatory or inhibitory signaling domain of a protein selected from the group consisting of: CD28, ICOS, CTLA4, 41BB, CD27, CD30, CD132, OX-40, TACI, GITR, HVEM, TIM3, PD1, LAG5, TIGIT, and derivatives, mutants, variants, fragments, and combinations thereof.

In a sixth aspect, a polypeptide comprises an antigen binding domain, a transmembrane domain, a signaling domain, the signaling domain comprising a primary signaling domain, a co-signaling domain, biologically active domains, or combinations thereof. In certain embodiments, a co-signaling domain comprises a signaling domain or functional fragment thereof, of: CD28, inducible T cell co-stimulator (ICOS, CD278), 41BB (CD137, tumor necrosis factor receptor superfamily member 9 (TNFRS9)), CD27, CD30, CD132, OX-40, TACI (Transmembrane activator and CAML interactor; tumor necrosis factor receptor superfamily member 13B (TNFRSF13B)), GITR (glucocorticoid-induced TNFR-related protein), HVEM (Herpesvirus entry mediator; tumor necrosis factor receptor superfamily member 14 (TNFRSF14)), other TNFR superfamily members, and derivatives, mutants, variants, fragments, and combinations thereof, wherein the antigen binding domain specifically binds to HIV antigens. In certain embodiments, the antigen specific binding domain comprises an antibody, a TCR variable region, a soluble T cell receptor, aptamer, or fragments thereof. In certain embodiments, the T cell receptor or antibody is a single chain fragment, for example an scFv. In certain embodiments, the primary signaling domain comprises a CD3 chain domain selected from the group consisting of: a CD3ζ chain, a CD3γ chain, a CD3δ chain, a CD3ε chain, derivatives, mutants, variants, fragments, and combinations thereof. In certain embodiments, the signaling domain optionally comprises an Fcγ domain, derivatives, mutants, variants, fragments, or combinations thereof. In certain embodiments, the co-signaling domain is a costimulatory domain derived from a protein selected from the group consisting of: CD28, ICOS, 41BB, CD27, CD30, derivatives, mutants, variants, fragments, and combinations thereof. In certain embodiments, the co-signaling domain comprises a CD28, a 41BB, derivatives, mutants, fragments, or combinations thereof. In certain embodiments, the signaling domain is selected from the group consisting of: (i) CD28, ICOS, 41BB, or combinations thereof; (ii) at least one domain selected from TACI, HVEM, GITR, OX40, CD27, CD30; and (iii) a CD3ζ chain, a CD3γ chain, a CD3δ chain, a CD3ε chain, Fcγ, or combinations thereof.

In a seventh aspect, a method of preventing or treating a subject infected with HIV comprises administering to the subject a pharmaceutical composition comprising an effective amount of: a TCR polypeptide embodied herein; a nucleic acid polynucleotide sequence encoding a TCR fusion polypeptide embodied herein; the isolated cell embodied herein; or combinations thereof, thereby, preventing or treating the subject infected with HIV. In certain embodiments, the isolated cell is an autologous cell, allogeneic cell, haplotype matched cell, haplotype mismatched cell, haplo-identical cell, xenogeneic cell, stem cell, a cell line, or combinations thereof. The presence or absence of the HIV virus can be determined via any means, such as for example, p24 detection or lack thereof, etc.

In an eighth aspect, the polypeptides, nucleic acid sequences, or isolated cells embodied herein are administered as part of a therapeutic regimen with one or more standard therapeutic agents. In certain embodiments, the therapeutic agents comprise a therapeutically effective amount of a non-nucleoside reverse transcriptase inhibitor (NNRTI), a nucleoside reverse transcriptase inhibitor (NRTI), a protease inhibitor, or combinations thereof. In certain embodiments, the NNRTI comprises: etravirine, efavirenz, nevirapine, rilpivirine, delavirdine, nevirapine, or combinations thereof. In certain embodiments, the NRTI comprises: lamivudine, zidovudine, emtricitabine, abacavir, zalcitabine, dideoxycytidine, azidothymidine, tenofovir disoproxil fumarate, didanosine (ddI EC), dideoxyinosine, stavudine, abacavir sulfate, or combinations thereof. In certain embodiments, a protease inhibitor comprises: amprenavir, tipranavir, indinavir, saquinavir mesylate, lopinavir and ritonavir (LPV/RTV), fosamprenavir Ca (FOS-APV), ritonavir, darunavir, atazanavir sulfate, nelfinavir mesylate, or combinations thereof.

In a ninth aspect, an expression vector is disclosed herein encoding any one of the TCRs embodied herein.

In a tenth aspect, a method is provided for treating a subject suffering from a HIV infection, comprising: isolating and separating CD8$^+$ T cells from a biological sample; contacting the T cells with an expression vector encoding a TCR embodied herein; stimulating the T cells with a specific antigen to obtain a therapeutically effective number of antigen-specific T cells; and, reinfusing the T cells into the subject, thereby treating the subject. The presence or absence of the HIV virus can be determined via any means, such as for example, p24 detection or lack thereof, etc. Other aspects are described infra.

Definitions. Unless defined otherwise, all technical and scientific terms used herein have the same meaning as commonly understood by one of ordinary skill in the art to which the invention pertains. Although any methods and materials similar or equivalent to those described herein can be used, the preferred materials and methods are described herein. In describing and claiming the molecules and methods disclosed herein, the following terminology will be used. The terminology used herein describes particular embodiments only, and is not intended to be limiting.

The articles "a" and "an" refer to one or to more than one (i.e., to at least one) of the grammatical object of the article. By way of example, "an element" means one element or more than one element. Thus, "a cell," for example, includes a plurality of the cells of the same type. Furthermore, "including," "includes," "having," "has," "with," or variants thereof are used in either the detailed description and/or the claims in a manner similar "comprising."

Where particular values are described in the application and claims, unless otherwise stated "about" conveys any numbers in a range that would round to the last significant digit.

As used herein, "anti-viral agent" or "anti-retroviral agent" refer to any molecule used for the treatment of a virus. The terms include agents to alleviate any symptoms associated with the virus, for example, anti-pyretic agents, anti-inflammatory agents, chemotherapeutic agents, and the like. An antiviral agent includes, without limitation: antibodies, aptamers, adjuvants, anti-sense oligonucleotides, chemokines, cytokines, immune stimulating agents, immune modulating agents, B-cell modulators, T-cell modulators, NK cell modulators, antigen presenting cell modulators, enzymes, siRNAs, ribavirin, protease inhibitors, helicase inhibitors, polymerase inhibitors, neuraminidase inhibitors, nucleoside reverse transcriptase inhibitors, non-nucleoside reverse transcriptase inhibitors, purine nucleosides, chemokine receptor antagonists, interleukins, or combinations thereof. The term also refers to NNRTIs, NRTIs, analogs, variants, etc.

As used herein, "comprising," "comprise," or "comprised," and variations thereof, in reference to defined or described elements are inclusive or open ended, permitting additional elements. "Comprise" and its variants indicate that the defined or described item, composition, apparatus, method, process, system, etc. includes those specified elements—or, as appropriate, equivalents thereof—and that other elements can be included and still fall within the scope/definition of the defined item, etc.

As used herein, "domain" and "motif" are used interchangeably to refer to both structured domains having one or more particular functions and unstructured segments of a polypeptide that, although unstructured, retain one or more particular functions. For example, a structured domain may encompass but is not limited to a continuous or discontinuous plurality of amino acids, or portions thereof, in a folded polypeptide comprising a three-dimensional structure which contributes to a particular function of the polypeptide. A domain may include an unstructured segment of a polypeptide comprising a plurality of two or more amino acids, or portions thereof, that maintains a particular function of the polypeptide unfolded or disordered. Also encompassed within "domain" or "motif" are disordered or unstructured stretches that can become structured or ordered upon association with a target or binding partner. Non-limiting examples of intrinsically unstructured domains and domains of intrinsically unstructured proteins are described, e.g., in Dyson & Wright (2005) *Nat. Rev. Mol. Cell Biol.* 6:197-208.

An "effective amount" means an amount which provides a therapeutic or prophylactic benefit.

"Encoding" refers to the inherent property of specific nucleotide sequences—such as a gene, a cDNA, or an mRNA—to serve as templates for synthesis of other macromolecules in biological processes. Thus, a gene "encodes" a protein if transcription and translation of mRNA corresponding to that gene produces the protein. Both the coding strand—the nucleotide sequence of which is identical to the mRNA sequence and is usually provided in sequence listings—and the non-coding strand—used as the template for transcription of a gene or cDNA—can be referred to as "encoding" the protein or other product. Unless otherwise specified, a "nucleotide sequence encoding" an amino acid sequence includes all nucleotide sequences that are degenerate versions of each other and that encode the same amino acid sequence. The phrase "nucleotide sequence that encodes a protein or an RNA" may also include introns to the extent that the nucleotide sequence encoding the protein may in some version contain an intron(s).

As used herein, "expression" conveys the transcription and/or translation of a particular nucleotide sequence driven by its promoter. An "expression vector" comprises a recombinant polynucleotide with expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes), and viruses (e.g., lentiviruses, retroviruses, adenoviruses, and adeno-associated viruses) that incorporate the recombinant polynucleotide.

"Optional" or "optionally" means that the subsequently described event or circumstance can occur or cannot occur, and that the description includes instances where the event or circumstance occurs and instances where it does not.

As used herein, "or" is generally employed in its sense including "and/or" unless the content clearly dictates otherwise.

"Parenteral" administration of an immunogenic composition includes, e.g., subcutaneous (s.c.), intravenous (i.v.), intramuscular (i.m.), or intrasternal injection, or infusion techniques.

As used herein, "patient" or "individual" or "subject" are used interchangeably herein to convey a mammalian subject to be treated, with human patients being preferred. In some cases, the methods described herein find use in experimental animals, in veterinary application, and in the development of animal models for disease, including, but not limited to, rodents (e.g., mice, rats, & hamsters) and primates.

A polypeptide or nucleic acid molecule is "substantially identical" when it exhibits at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison. "Identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window. The degree of amino acid or nucleic acid sequence identity for purposes of the present disclosure is determined using the BLAST algorithm, described in Altschul et al. (199) *J. Mol. Biol.* 215:403-10. This algorithm identifies high scoring sequence pairs (HSPS) by identifying short words of length W in the query sequence, which either match or satisfy some positive-valued threshold score T when aligned with a word of the same length in a database sequence. T is referred to as the neighborhood word score threshold (Altschul et al., supra.). Initial neighborhood word hits act as seeds for initiating searches to find longer HSPs containing them. The word hits are then extended in both directions along each sequence for as far as the cumulative alignment score can be increased. Cumulative scores are calculated for nucleotides sequences using the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below due to the accumulation of one or more negative-scoring residue alignments; or the end of either sequence is reached. For determining the percent identity of an amino acid sequence the BLASTP settings are: word length (W), 3; expectation (E), 10; and the BLOSUM62 scoring matrix. For analysis of nucleic acid sequences, the BLASTN program settings are word length (W), 11; expectation (E), 10; M=5; N=−4; and a comparison of both strands. The TBLASTN program (using a protein sequence to query nucleotide sequence databases) uses a word length (W) of 3, an expectation (E) of 10, and a BLOSUM 62 scoring matrix. (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul (1993) *Proc. Nat'l. Acad. Sci. USA* 90:5873-87). The smallest sum probability (P(N)), provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01.

As used herein, a "pharmaceutically acceptable" component/carrier etc. is suitable for use with humans and/or animals without undue adverse side effects (such as toxicity, irritation, and allergic response) commensurate with a reasonable benefit/risk ratio.

To "treat" a disease conveys reducing the frequency or severity of at least one sign or symptom of a disease or disorder experienced by a subject. Treatment of a disease or disorders includes the eradication of a virus. "Treatment" is an intervention to alter the pathology or symptoms of a disorder including: (1) eradicating HIV; (2) delaying the appearance of clinical symptoms of HIV infection in an infected human or other mammal that does not yet experience or display clinical or subclinical symptoms; (3) inhibiting progression to AIDS, i.e., arresting, reducing or delaying the development of the disease or a relapse thereof (in case of maintenance treatment) or at least one clinical or subclinical symptom thereof; or (4) relieving the disease, i.e., causing regression of the state, disorder or condition or at least one of its clinical or subclinical symptoms. The benefit to an individual in "treatment" is either statistically significant or at least perceptible to the patient or to the physician.

As used herein, a "therapeutically effective" amount (i.e., an effective dosage) means an amount sufficient to produce a therapeutically (e.g., clinically) desirable result. The compositions can be administered from one or more times per day to one or more times per week; including once every other day. Certain factors can influence the dosage and timing required for effective treatment, including but not limited to disease severity, previous treatments, patient's general health and/or age, and other diseases present. Moreover, treatment with a therapeutically effective amount can include a single treatment or a series of treatments.

Where any amino acid sequence is specifically referred to by a Swiss Prot. or GENBANK Accession number, the sequence is incorporated herein by reference. Information associated with the accession number, such as identification of signal peptide, extracellular domain, transmembrane domain, promoter sequence and translation start, is also incorporated herein in its entirety by reference.

Genes: All genes, gene names, and gene products disclosed herein are intended to correspond to homologs from any species for which the compositions and methods disclosed herein are applicable. When a gene or gene product from a particular species is disclosed, this disclosure is exemplary only, and is not to be interpreted as a species limitation unless expressly indicated. Thus, for example, genes or gene products disclosed herein are intended to encompass homologous and/or orthologous genes and gene products from other species.

Ranges: various aspects of the TCRs and methods described herein can be presented in a range format. The description in range format is merely for convenience and brevity and should not be construed as an inflexible limitation. Description of a range should be considered to have specifically disclosed all the possible subranges as well as individual numerical values within that range. For example, "from 1 to 6" should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of range breadth.

BRIEF DESCRIPTION OF THE DRAWINGS

FIG. 8A shows results with no peptide; FIG. 8B shows results with the E18 peptide.

DETAILED DESCRIPTION

Figure 1:
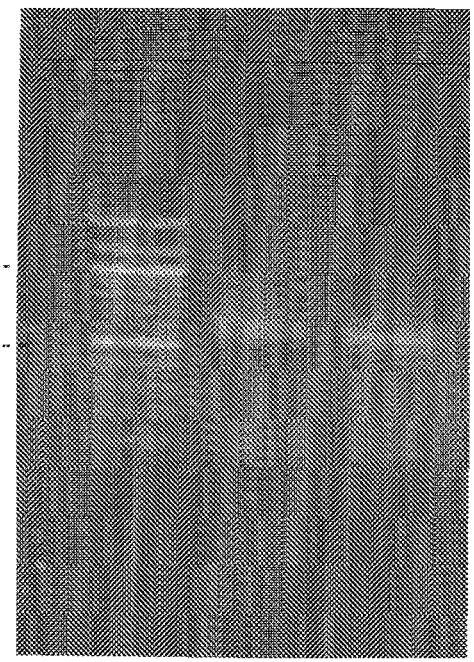
FIG. 1 shows a blot of SMARTer RACE PCR products for human TCR α and β genes specific to HLA-B8/HIV p24 gag (260-267) peptide complex (B08EI8).

Therapeutic approaches described herein to treat HIV infections involve engineered TCR molecules specific to HIV peptide/HLA complexes. These TCRs guide direct killing and/or enable robust immune responses against virally infected cells. Specifically, novel TCR molecules were generated that recognize HIV peptide antigens, which present in HLA molecules on antigen presenting cells and/or CD4+ T cells during infection. For example, HIV peptide/HLA molecules shown in Table 1 serve as TCR targets derived from HIV-specific cytotoxic CD8+ T cells (CTLs).

Human Immunodeficiency Virus. Acquired Immunodeficiency Disease (AIDS) remains incurable due to the permanent integration of HIV-1 into the host genome. Current therapy (HAART) for controlling HIV-1 infection and impeding AIDS development profoundly reduces viral replication and reduces plasma viremia to a minimal level, but HAART fails to suppress low level viral genome expression and replication in tissues. HAART also cannot target latently-infected cells (e.g., resting memory T cells, brain macrophages, microglia, astrocytes, and gut-associated lymphoid cells) that serve as HIV-1 reservoirs. Persistent HIV-1 infection is also linked to co-morbidities including heart disease, renal disease, osteopenia, and neurological disorders. HIV and other retroviruses are highly mutable, so there is a need for a broader spectrum of reagents and methods for targeting the infected or latently infected cells.

Disclosed herein are engineered TCR molecules specific for HIV peptide/HLA complexes. These TCRs guide direct killing and/or enable robust immune responses against virally infected cells.

Viral Reservoirs: Whereas most HIV replication takes place in activated CD4+ T lymphocytes, other cell populations may become infected. Resting T cells constitute a latent HIV reservoir. At one end of the spectrum, in the activated T cell, multiple cellular factors and the viral Tat protein upregulate HIV transcription. At the other end of the spectrum, fully quiescent T cells—those in the G0 phase of the cell cycle—cannot sustain productive HIV replication. Between those extremes, cytokine exposure can induce quiescent cells to move far enough along the cell cycle (i.e., to the G1 phase) to induce reverse transcription. Such cells are susceptible to HIV infection, but do not undergo full activation and cell cycling.

HIV can infect T cells that are not fully activated. During the course of HIV infection, integrated and infection-competent provirus remains among resting memory CD4+ T cells. The frequency of these cells remains stable for years, decreasing only minimally with the antiretroviral therapy combinations.

Other potential infection reservoirs include genitourinary tract sites, certain monocyte populations, certain tissue macrophages, and possibly the kidney. This reservoir replenishes over time in the resting memory cell compartment. The long half-life of these cells indicates that current treatment strategies will not eradicate infection in this compartment. Neither intensive and prolonged antiretroviral therapies nor strategies to activate expression of virus from these reservoirs has eradicated virus in infected persons, although such therapies modestly diminish frequency with which virus is found in resting memory cells.

T Cell Receptor Molecules. Generation of TCR molecules which specifically recognize HIV peptide antigens can be used to treat HIV infection where HIV antigens are presented in HLA molecules on antigen presenting cells (APCs) and/or CD4 T cells during infection.

The TCR complex is composed of a ligand-binding subunit, the α and β chains, and a signaling subunit, namely the CD3ε, γ, and δ chains and the TCR chain. This complex participates in T-cell activation upon the presentation of the antigen peptide bound to HLA on APCs, including dendritic cells, macrophages and B cells. Co-stimulatory receptors (e.g., CD2, CD28, CD4, CD8, and integrin molecules) contribute to signal transduction by modulating the response threshold. All the above components along with accessory proteins essential for HLA are a part of the immunological synapse that initiates T-cell activation.

The TCR fusion polypeptides provided herein comprise a TCR variable alpha (Vα) domain, a TCR variable beta domain (Vβ) and a TCR constant region domain (C), wherein the TCR fusion polypeptide is specific for HIV peptides. The TCR fusion polypeptide further comprises a linker molecule linking the Vα and the Vβ domains. In certain embodiments, the TCR polypeptide is a single chain fragment, such as, a single chain variable fragment (scFv). In certain embodiments, the TCR polypeptide is HLA class II-restricted. In certain embodiments, the TCR is HLA class I-restricted. In certain embodiments, the TCR fusion polypeptide is HLA-A, HLA-B or HLA-C restricted. In certain embodiments, the TCR polypeptide specifically binds to one or more of HIV Gag, Pol, Nef, or combinations thereof. In certain embodiments, the HIV peptides comprise amino acid sequences from Gag, Gag-Pol precursor, Pro (protease), Reverse Transcriptase (RT), integrase (In), Env, or combinations thereof. In certain embodiments, the HIV peptides comprise amino acid sequences from regulatory proteins e.g. Tat, Rev, accessory proteins, e.g. Nef, Vpr, Vpu, Vif, or combinations thereof.

In certain embodiments, the TCR polypeptides are soluble polypeptides. In certain embodiments, the molecules embodied herein are specific for one or more HIV antigens comprising Gag, Gag-Pol precursor, Pro, Reverse Transcriptase (RT), integrase (In), Env, Tat, Rev, Nef, Vpr, Vpu, Vif, or combinations thereof.

In certain embodiments, the TCR fusion polypeptide, further comprises immune signaling domains, transmembrane domains, cytoplasmic domains, biologically active domains, or combinations thereof. In certain embodiments, the biologically active domains comprise: cytokines, monokines, checkpoint inhibitors, antigen specific antibody domains, enzymes, or combinations thereof.

In certain embodiments, the TCR fusion polypeptide is multimeric. In certain embodiments, a TCR fusion polypeptide comprises a TCR Vα domain, a TCR Vβ domain, a TCR C domain, and an immune effector domain, wherein the TCR fusion polypeptide is specific for HIV peptides. In certain embodiments, the TCR fusion polypeptide further comprises a linker molecule linking the Vα and the Vβ domains. In certain embodiments, the TCR is HLA class II-restricted. In certain embodiments, the TCR is HLA class I-restricted. In certain embodiments, the TCR fusion polypeptide specifically binds to HIV peptides, wherein the HIV peptides comprise Gag, Pol, Nef, or combinations thereof. In certain embodiments, the immune effector domains comprise CD3 or CD28 signaling domains. In certain embodiments, the TCR fusion polypeptide is soluble or membrane bound. In certain embodiments, the membrane bound TCR fusion polypeptide comprises transmembrane domains, cytoplasmic domain, biologically active domains, or combinations thereof. The biologically active domains, include, without limitation: cytokines, checkpoint inhibitors, antigen specific antibody domains, enzymes, or combinations thereof.

In certain embodiments, the TCR molecule comprises one or more co-stimulatory domains comprising: CD28, ICOS, OX-40, or 41BB. The intracellular signaling region of a TCR or cell as described herein may comprise signaling regions from one, two, three, four, or all five of these proteins in addition to the other regions specified herein. The co-stimulatory domains may comprise co-stimulatory domains from both 41BB and CD28. The 41BB co-stimulatory domain can be downstream of the CD28 co-stimulatory domains.

The TCR molecule may also comprise a spacer or hinge region situated between the antigen binding region and T cell plasma membrane. Commonly a spacer or hinge is a sequence derived from IgG subclass IgG1, IgG4, IgD, or CD8. In certain embodiments, the hinge region comprises a CD28 motif. The hinge region can be any length, for example 1 amino acid, or 10 amino acids, or 20 amino acids, or 50 amino acids, or 60 amino acids, or 70 amino acids, or 80 amino acids, or 100 amino acids, or 120 amino acids, or 140 amino acids, or 160 amino acids, or 180 amino acids, or 200 amino acids, or 250 amino acids, or 300 amino acids, or any number therebetween.

A TCR molecule may further comprise a linker region, for example a region rich in glycine for flexibility. Additionally or alternatively, the linker may be rich in serine/threonine for solubility. The linker region can connect the variable heavy ($V_H$) chain N-terminus with the variable light ($V_L$) chain C-terminus, or vice versa.

Suitable TCR sequences for uses as disclosed herein include TCRs having at least 85% sequence identity to any one of SEQ ID NOs: 2, 4, 6, 8, 10, 12, 14, 16, or 18. In certain embodiments, the TCR has at least 90% (e.g., at least 91%, at least 92%, at least 93%, at least 94%, at least 95%, at least 96%, at least 97%, at least 98%, at least 99%, or even 100%) sequence identity to any one of SEQ ID NOs: 2, 4, 6, 8, 10, 12, 14, 16, or 18. In certain embodiments, the TCR has at least 70% (e.g., at least 75%, at least 80%, at least 85%, at least 90%, at least 91%, at least 92%, at least 93%, at least 94%, at least 95%, at least 96%, at least 97%, at least 98%, or at least 99%) sequence identity to any one of SEQ ID NOs: 2, 4, 6, 8, 10, 12, 14, 16, or 18, but retains 99% identity or even 100% identity to the complementarity determining region (CDR) portions of the Vα and/or Vβ domains. In certain embodiments, the signal peptide is cleaved from the mature TCE. In certain embodiments, the BirA tag may be removed or omitted from the TCR.

Antigen binding domain: In certain embodiments a TCR polypeptide comprises an antigen binding domain, a transmembrane domain, a signaling domain, the signaling domain comprising a primary signaling domain, a co-signaling domain, biologically active domains, or combinations thereof. In certain embodiments, the antigen specific binding domain comprises an antibody, a TCR variable region, a soluble T cell receptor, aptamer or fragments thereof. In certain embodiments, the T cell receptor or antibody is a single chain fragment, e.g., an scFv.

In certain embodiments, the antigen binding domain is or comprises an antibody or antibody fragment. In certain embodiments, the antibodies are human antibodies, including any known to bind a targeting molecule. "Antibody" is used herein in the broadest sense and includes polyclonal and monoclonal antibodies, intact antibodies and functional (antigen-binding) antibody fragments, fragment antigen binding (Fab) fragments, F(ab')$_2$ fragments, Fab' fragments, Fv fragments, recombinant IgG (rIgG) fragments, $V_H$ regions capable of specifically binding the antigen, single chain antibody fragments, including single chain variable fragments (scFv), and single domain antibodies (e.g., sdAb, sdFv, nanobody) fragments. "Antibody" encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, "antibody" should be understood to encompass functional antibody fragments thereof. The term also encompasses intact or full-length antibodies, including antibodies of any class or sub-class, including IgG and sub-classes thereof, IgM, IgE, IgA, and IgD.

Signaling domains: In some embodiments, an intracellular signaling domain is or includes a primary signaling domain, a signaling domain capable of inducing a primary activation signal in a T cell. The intracellular signaling domain may include a CD3 intracellular signaling domain, optionally a CD3ζ chain, or a signaling portion thereof. In some embodiments, the intracellular signaling domain further includes a second signaling domain. In some embodiments, the second signaling domain is a costimulatory signaling domain that may include an intracellular signaling domain of a CD28, or a signaling portion thereof.

In certain embodiments, a co-signaling domain comprises a signaling domain or functional fragment thereof derived from: CD28, CD278, CD137, CD27, CD30, CD132, OX-40, TACI, GITR, HVEM, other TNFR superfamily members, and derivatives, mutants, variants, fragments, and combinations thereof, wherein the antigen binding domain specifically binds to HIV antigens. In certain embodiments, the antigen specific binding domain comprises an antibody, a TCR variable region, a soluble T cell receptor, aptamer, or fragments thereof. In certain embodiments, the T cell receptor or antibody is a single chain fragment, e.g., an scFv. In certain embodiments, the primary signaling domain comprises a CD3 chain domain selected from the group consisting of a CD3ζ chain, a CD3γ chain, a CD3δ chain, a CD3ε chain, derivatives, mutants, variants, fragments, and combinations thereof. In certain embodiments, the signaling domain optionally comprises an Fcγ domain, derivatives, mutants, variants, fragments, or combinations thereof. In certain embodiments, the co-signaling domain is a costimulatory domain derived from a protein selected from the group consisting of CD28, ICOS, 41BB, CD27, CD30, derivatives, mutants, variants, fragments, and combinations thereof. In certain embodiments, the co-signaling domain comprises a CD28, a 41BB, derivatives, mutants, fragments, or combinations thereof. In certain embodiments, the signaling domain is selected from the group consisting of: (i) CD28, ICOS, 41BB, or combinations thereof; (ii) at least one domain selected from TACI, HVEM, GITR, OX40, CD27, CD30; and (iii) a CD3ζ chain, a CD3γ chain, a CD3δ chain, a CD3ε chain, Fcγ, or combinations thereof.

Methods of Treatment. Method are disclosed herein for treating a subject infected with HIV. These methods comprise administering to the subject a pharmaceutical composition comprising an effective amount of: a TCR polypeptide embodied herein; a nucleic acid polynucleotide sequence encoding a TCR fusion polypeptide embodied herein; the isolated cell embodied herein; or combinations thereof. In certain embodiments, the isolated cell is an autologous cell, allogeneic cell, haplotype matched cell, haplotype mismatched cell, haplo-identical cell, xenogeneic cell, stem cell, a cell line, or combinations thereof.

In certain embodiments, a subject suffering from HIV infection may be treated by: isolating and separating CD8$^+$ T cells from a biological sample; contacting the T cells with an expression vector encoding a TCR embodied herein which specifically binds to an antigen associated with an HIV; stimulating the T cells with a specific antigen to obtain a therapeutically effective number of antigen-specific T cells; and reinfusing the T cells into the subject.

Any number of methods known in the art can be used to isolate cells, for transduction with any number of TCRs embodied herein, such as CD8$^+$ T cells, or any other cell type that may be used in carrying out the treatment of a subject. Thus, also provided are various other genetically engineered cells expressing the TCRs embodied herein. The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, CD4$^+$ cells, CD8$^+$ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells and/or of CD4$^+$ and/or of CD8$^+$ T cells are naive T ($T_N$) cells, effector T cells ($T_{EFF}$), memory T cells and sub-types thereof, such as stem cell memory T ($T_{SCMX}$), central memory T ($T_{CM}$ effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and induced regulatory T (Treg) cells, helper T cells, such as $T_H1$ cells, $T_H2$ cells, $T_H3$ cells, $T_H17$ cells, $T_H9$ cells, $T_H22$ cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cells include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

In some embodiments, preparation of the engineered cells includes one or more culture and/or preparation steps. The cells for introduction of the TCRs, may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered. In certain embodiments, a biological sample is obtained from one or more sources comprising: autologous, allogeneic, haplotype matched, haplotype mismatched, haplo-identical, xenogeneic, cell lines, or combinations thereof.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, or pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturers instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

T cells, are isolated by positive or negative selection techniques. For example, $CD3^+$, $CD28^+$ T cells can be positively selected using anti-CD3/anti-CD28 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker"1") at a relatively higher level (marker$^{high}$) on the positively or negatively selected cells, respectively.

In some embodiments, T cells are separated from a PBMC sample by negative selection of markers expressed on non-T cells, such as B cells, monocytes, or other white blood cells, such as CD 14. In some aspects, a $CD4^+$ or $CD8^+$ selection step is used to separate $CD4^+$ helper and $CD8^+$ cytotoxic T cells. Such $CD4^+$ and $CD8^+$ populations can be further sorted into sub-populations by positive or negative selection for markers expressed or expressed to a relatively higher degree on one or more naive, memory, and/or effector T cell subpopulations.

In some aspects, a CD4 expression-based selection step is used to generate the $CD4^+$ cell population or sub-population, such that both the positive and negative fractions from the CD4-based separation are retained and used in subsequent steps of the methods, optionally following one or more further positive or negative selection steps. $CD4^+$ T helper cells are sorted into naïve, central memory, and effector cells by identifying cell populations that have cell surface antigens. $CD4^+$ lymphocytes can be obtained by standard methods. In some embodiments, naïve $CD4^+$ T lymphocytes are $CD45RO^+$, $CD45RA^+$, $CD62L^+$, $CD4^+$ T cells. In some embodiments, central memory $CD4^+$ cells are $CD62L^+$ and $CD45RO^+$.

In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR, e.g. anti-CD3. In some embodiments, the stimulating conditions include one or more agent, e.g. ligand, which is capable of stimulating a costimulatory receptor, e.g., anti-CD28. In some embodiments, such agents and/or ligands may be, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2, IL-15, and/or IL-7. In some aspects, IL-2 concentration is at least about 10 units/mL.

In some aspects, incubation is carried out in accordance with techniques such as those described in U.S. Pat. No. 6,040,177 to Riddell; Klebanoff et al. (2012) *J Immunother.* 35(9):651-60, Terakura et al. (2012) *Blood.* 1:72-82; and/or Wang et al. (2012) *J Immunother.* 35(9):689-701.

In some embodiments, the T cells are expanded by adding to the culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

Typically, administration of T cell therapies is defined by number of cells per kilogram of body weight. However, because T cells will replicate and expand after transfer, the administered cell dose will not resemble the final steady-state number of cells.

In an embodiment, a pharmaceutical composition comprising the cells as described herein may be administered at a dosage of $10^4$ to $10^9$ cells/kg body weight. In another embodiment, the pharmaceutical composition may be administered at a dosage of $10^5$ to $10^6$ cells/kg body weight, including all integer values within those ranges.

Compositions comprising the cells described herein may also be administered multiple times at these dosages. The cells can be administered by using infusion techniques that are known in the art (see, e.g., Rosenberg et al. (1988) NEJM 319:1676). The optimal dosage and treatment regimen for a particular subject can be readily determined by one skilled in the art by monitoring the patient for signs of disease and adjusting the treatment accordingly.

Pharmaceutical Compositions. In certain embodiments, any of the compositions described herein—e.g. soluble TCR fusion polypeptides, cells comprising a TCR fusion polypeptide embodied herein—may be administered to treat an HIV infection. These therapeutics can be combined with other cell-based therapies (e.g., stem cells, APCs, etc).

The compositions described herein may be prepared in a manner known in the art. These compositions are suitable for parenteral administration to mammals, particularly humans. The compositions comprise a therapeutically effective amount of the TCRs or cells alone, or in combination with one or more pharmaceutically acceptable carriers or diluents. "Pharmaceutically acceptable carrier" as used herein means any suitable carriers, diluents, or excipients. These include all aqueous and non-aqueous isotonic sterile injection solutions which may contain anti-oxidants, buffers, and solutes. Suitable carriers render the composition isotonic with the blood of the intended recipient, e.g., aqueous and non-aqueous sterile suspensions, which may include suspending agents and thickening agents, dispersion media, antifungal agents, antibacterial agents, isotonicity agents, absorption agents, and the like. Compositions as described herein may also include other supplementary physiologically active agents.

The carrier must be pharmaceutically "acceptable" in the sense of being compatible with the other ingredients of the composition and not injurious to the subject. Compositions include those suitable for parenteral administration, including subcutaneous, intramuscular, intravenous and intradermal administration. The compositions may conveniently be presented in unit dosage form and may be prepared by any method well known in the art of pharmacy. In general, the compositions are prepared by uniformly and intimately bringing into association any active ingredients with liquid carriers.

In an embodiment, the composition is suitable for parenteral administration. In another embodiment, the composition is suitable for intravenous administration.

Compositions suitable for parenteral administration include aqueous and nonaqueous isotonic sterile injection solutions which may contain anti-oxidants, buffers, bactericides and solutes, which render the composition isotonic with the blood of the intended recipient; and aqueous and non-aqueous sterile suspensions which may include suspending agents and thickening agents.

The TCRs and cells disclosed herein may also be combined with other drugs and/or other treatment regimens or modalities such as surgery. When the TCRs and cells disclosed herein are used in combination with known therapeutic agents the combination may be administered either in sequence (either continuously or broken up by periods of no treatment) or concurrently or as an admixture. Treatment in combination may also encompass treatment with either the compositions disclosed herein followed by a known treatment, or treatment with a known agent followed by treatment with the compositions disclosed herein (e.g., as maintenance therapy).

In other embodiments, the TCRs or cells embodied herein are administered as part of a therapeutic regimen with one or more standard therapeutic agents. In certain embodiments, the therapeutic agents comprise a therapeutically effective amount of NNRTI, NRTI, protease inhibitor, or combinations thereof. In certain embodiments, the NNRTI comprises: etravirine, efavirenz, nevirapine, rilpivirine, delavirdine, nevirapine, or combinations thereof. In certain embodiments, the NRTI comprises: lamivudine, zidovudine, emtricitabine, abacavir, zalcitabine, dideoxycytidine, azidothymidine, tenofovir disoproxil fumarate, didanosine (ddI EC), dideoxyinosine, stavudine, abacavir sulfate, or combinations thereof. In certain embodiments, a protease inhibitor comprises: amprenavir, tipranavir, indinavir, saquinavir mesylate, lopinavir and ritonavir (LPV/RTV), fosamprenavir Ca (FOS-APV), ritonavir, darunavir, atazanavir sulfate, nelfinavir mesylate, or combinations thereof.

Suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1: Generation of novel T cell receptors specific to HIV antigens. T cell responses against specific HIV peptide/HLA complexes can control of viral load and subsequent disease progression in HIV infected individuals. Through understanding the critical HIV epitopes and antiviral T cell activity responsible for controlling viral replication, effective vaccines, immunotherapies and cell-based therapies can mimic this control and provide protection to exposed individuals early in infection. Such therapies may also target and reduce latent HIV reservoirs in chronic HIV infections. TCRs can guide direct killing and/or enable robust immune responses against virally infected cells. Specifically, HIV peptide/HLA molecules shown in Table 1 serve as targets for TCRs derived from HIV-specific cytotoxic CD8 T cells (CTLs). Details of the isolation and expression of such TCRs and their characterization are provided below.

TABLE 1

HIV peptide/HLA complex specificities of human CD8+ T cells for TCR isolation

| HLA | HIV-1 Protein | AA | Peptide Sequence | Peptide Name |
|---|---|---|---|---|
| A3 | Gag p17 | 20-28 | SEQ ID NO: 19 | RK9 |
| A24 | Nef | 134-143 | SEQ ID NO: 20 | RF10 |
| B8 | Gag p24 | 260-267 | SEQ ID NO: 21 | EI8 |
| B8 | Nef | 90-97 | SEQ ID NO: 22 | FL8 |
| B14 | Gag p24 | 298-306 | SEQ ID NO: 23 | DA9 |
| B27 | Gag p24 | 263-272 | SEQ ID NO: 24 | KK10 |
| B35 | Nef | 71-81 | SEQ ID NO: 25 | RY11 |
| B57 | Gag p24 | 162-172 | SEQ ID NO: 26 | KF11 |
| B57 | Gag p24 | 147-155 | SEQ ID NO: 27 | ISP |
| B57 | Gag p24 | 308-316 | SEQ ID NO: 28 | QW9 |

HIV-specific CTLs of HIV infected individuals were isolated and further purified by flow cytometry sorting using cognate HIV peptide/HLA tetramers or antibodies specific to the known TCR Vβ chain. Total CTL RNA was purified with RNeasy Plus Mini Kit (Cat. No. 74134, QIAGEN). SMARTer RACE (SMARTer PCR cDNA synthesis Kit Cat. No. 634925, 634926, Clontech) amplified α and β genes of HIV-specific TCR. FIG. 1 shows exemplary SMARTer RACE PCR products for human TCR α and β genes specific to HLA-B8/HIV p24 gag (260-267) peptide complex (B08EI8).

Figure 2:
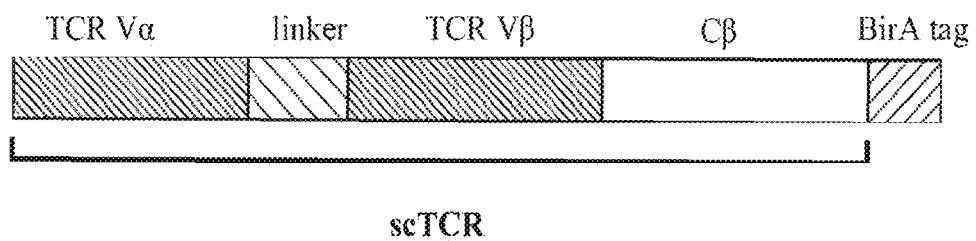
FIG. 2 schematically presents an HIV-specific scTCR-birA fusion construct.
Figure 3A:
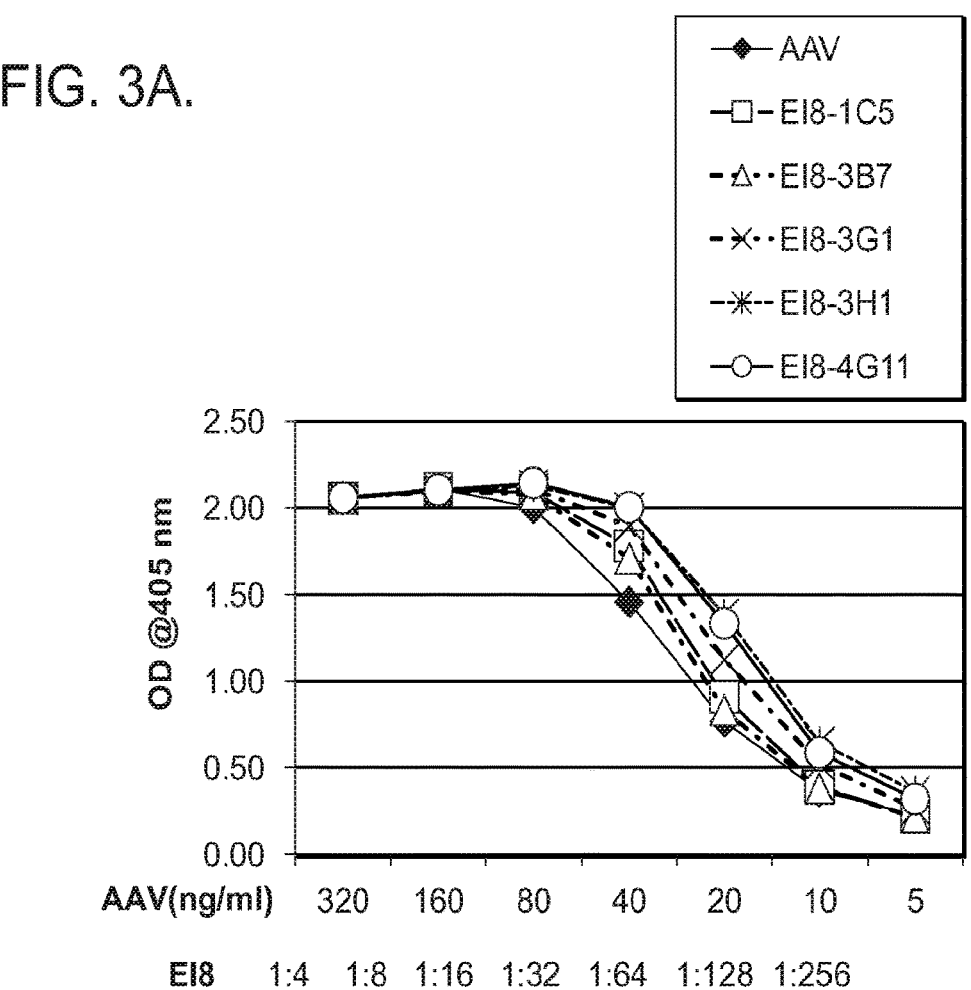
FIGS. 3A-3F show ELISA measurements of scTCR-BirA proteins secreted from CHO cell transfectants carrying vectors expressing the B08EI8 (FIG. 3A), B57ISP (FIG. 3B), B57QW9 (FIG. 3C), B08FL8 (FIG. 3D), A24RF10 (FIG. 3F) or B35RY11 (FIG. 3E) scTCR-BirA fusion proteins into culture supernatant measured using anti-TCR Cβ chain Ab (BF1) (capture) and biotinylated anti-TCR Cβ Ab (W4F) (probe). Multiple clones express B08EI8, B57ISP, B57QW9, B08FL8, A24RF10, RK9 or B35RY11 scTCR-BirA fusions.
Figure 3B:
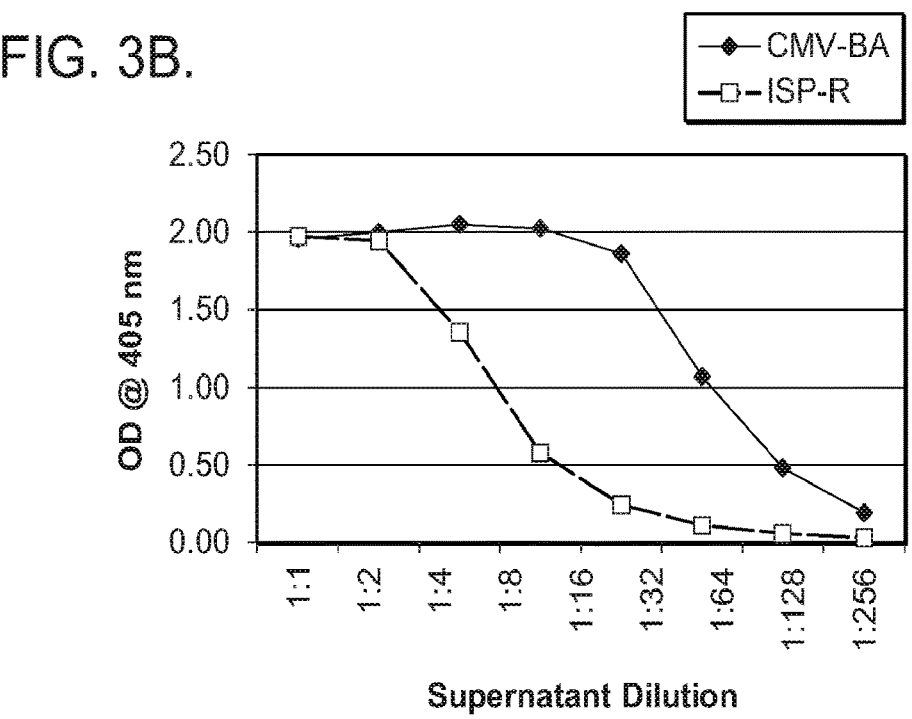
Figure 3C:
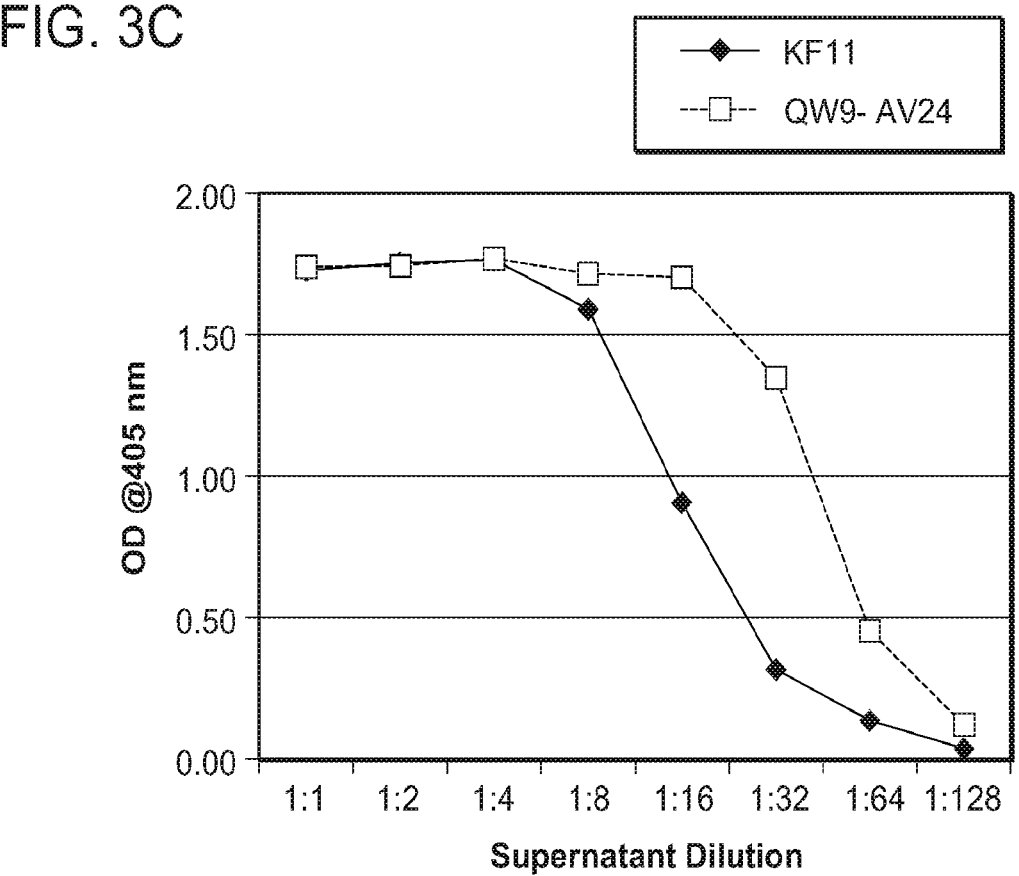
Figure 3D:
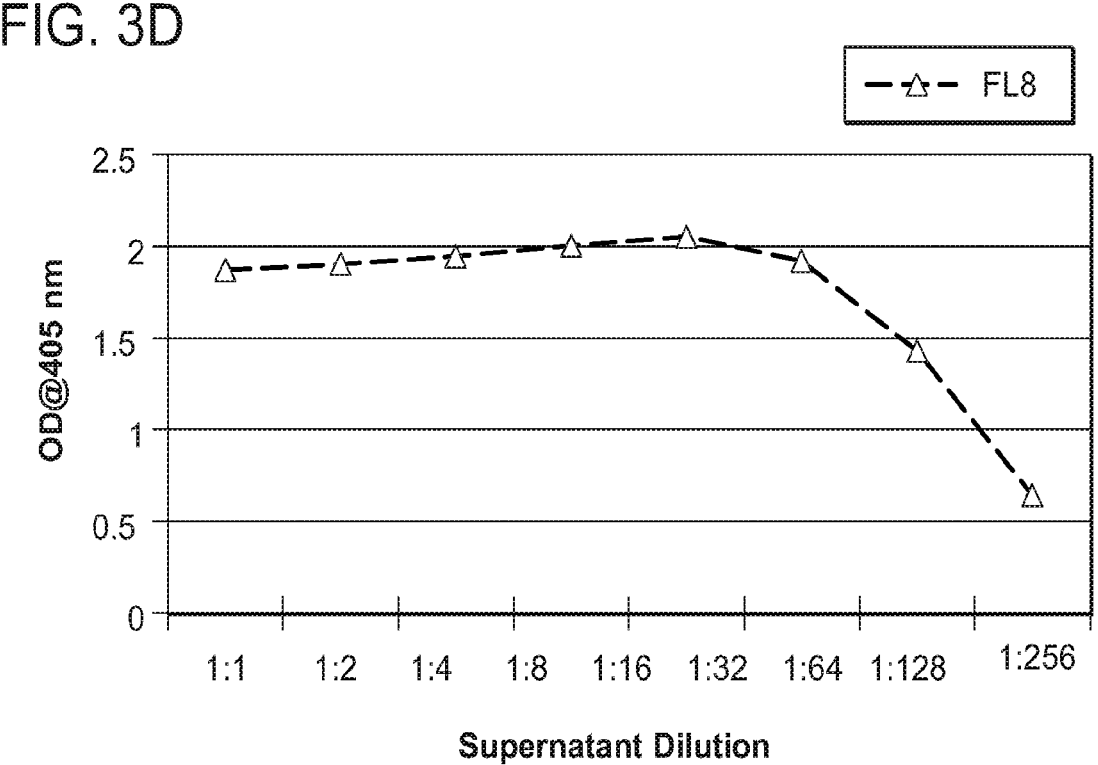
Figure 3E:
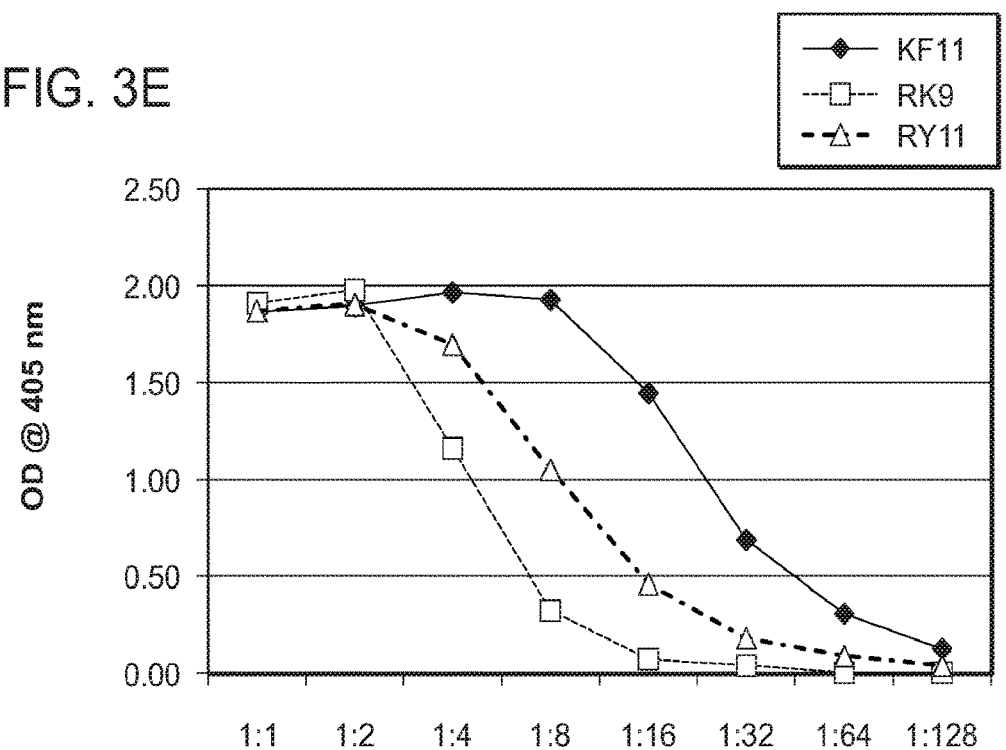
Figure 3F:
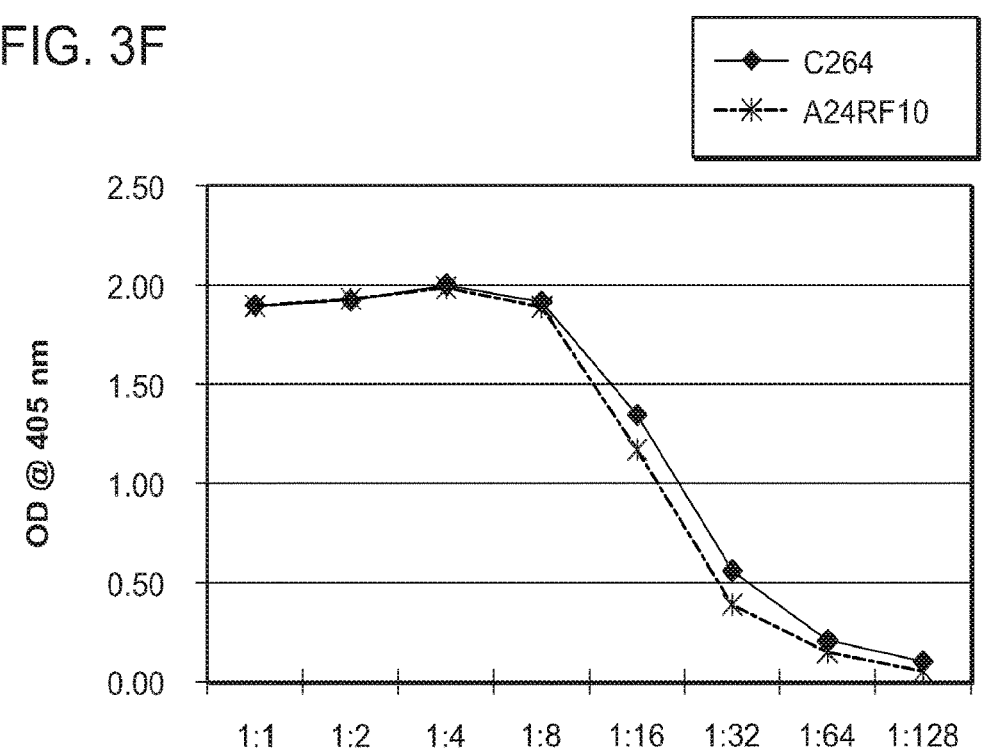
Figure 4B:
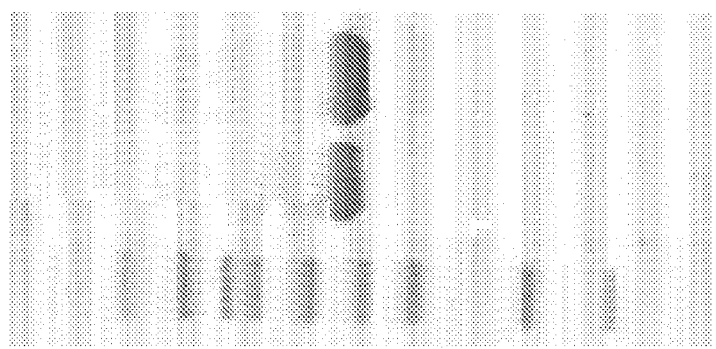
FIGS. 4A-4D demonstrate affinity-purified scTCR-BirA comprises primarily a single protein band of the expected molecular mass. B08EI8 scTCR (FIG. 4A lanes 2 and 3; molecule weight marker in lane 1); ISP-BirA (FIG. 4B in lanes 2 and 3; molecular weight marker in lane 1); QW9-BirA (FIG. 4C in lanes 1 and 2; molecular marker in lane 3); RY11-BirA (lane 2, FIG. 4D); and RK9-BirA (lanes 3 and 4, FIG. 4D; molecular weight marker in lane 1).
Figure 4A:
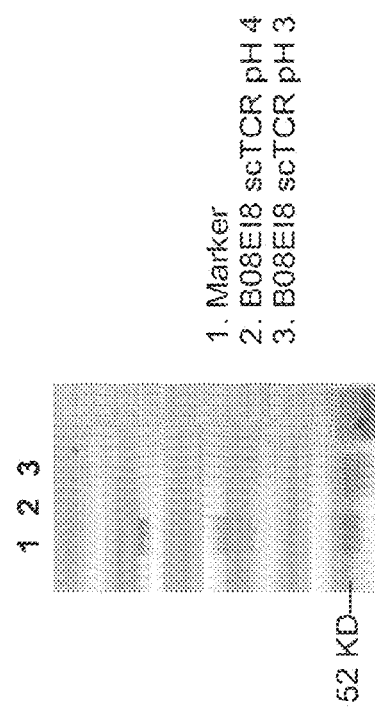
Figure 4C:
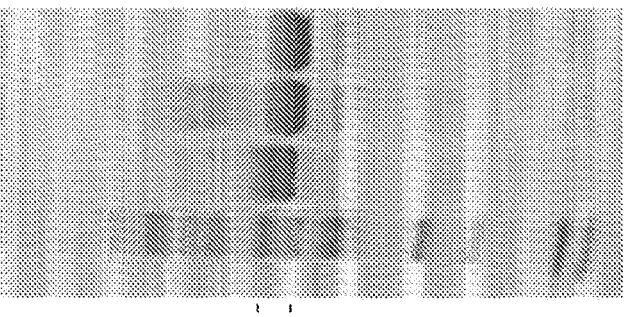
Figure 4D:
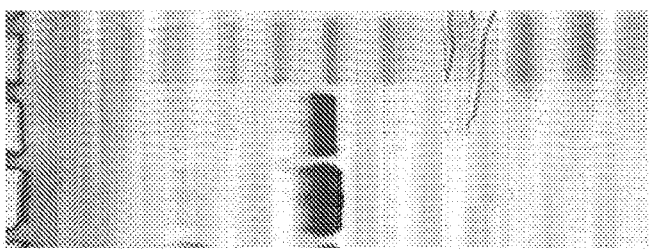
Figure 5A:
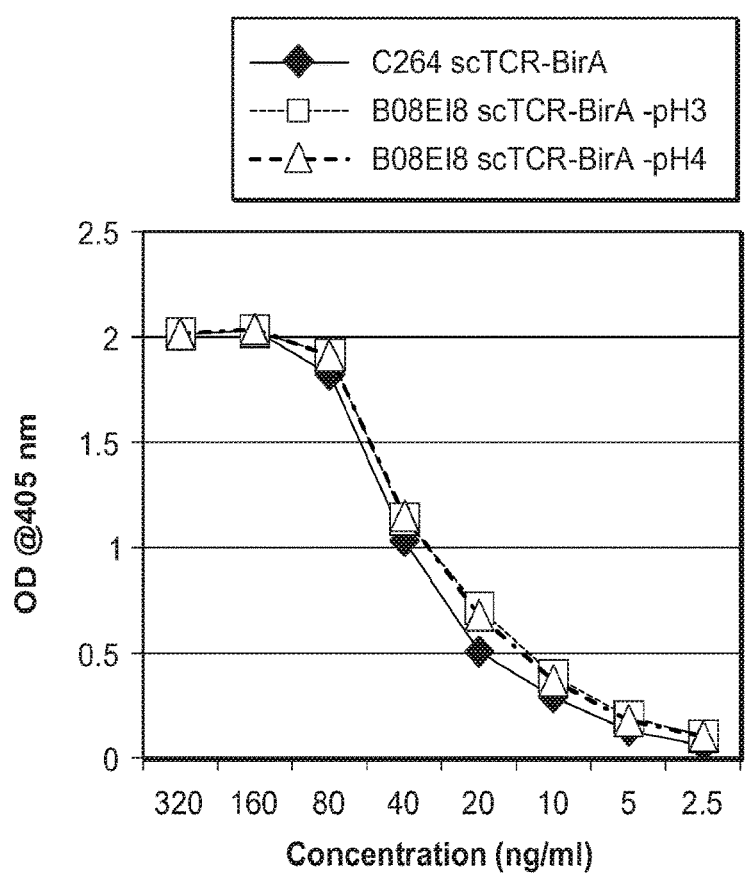
FIGS. 5A-5D demonstrate that purified scTCR-BirA reacts in TCR specific ELISA. Results for B08E18 scTCR-BirA are shown in FIG. 5A; results for ISP in FIG. 5B; results for QW9 in FIG. 5C; and results for E18-BA, RK9-BA and RY11-BA in FIG. 5D.
Figure 5B:
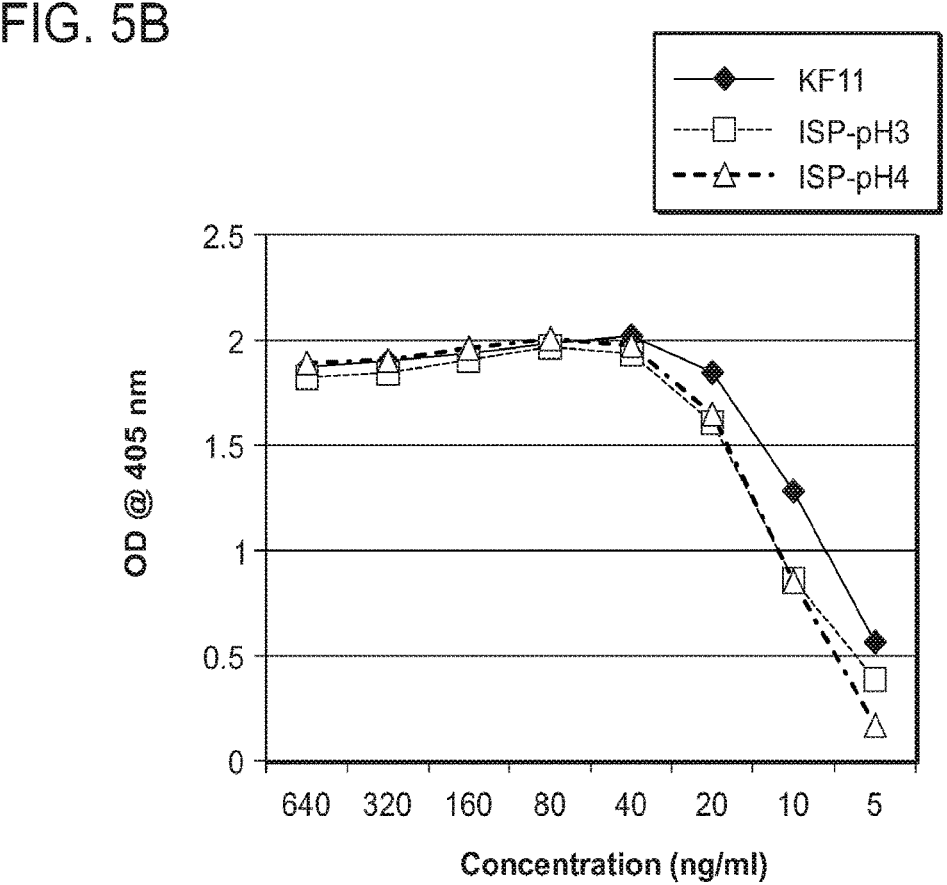
Figure 5C:
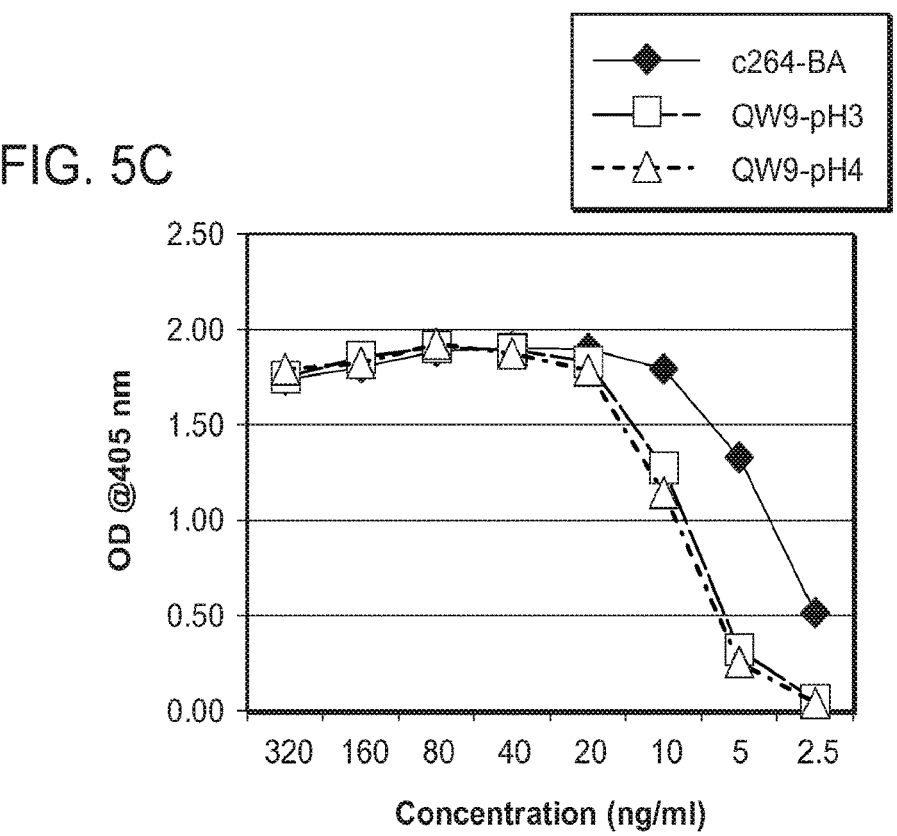
Figure 5D:
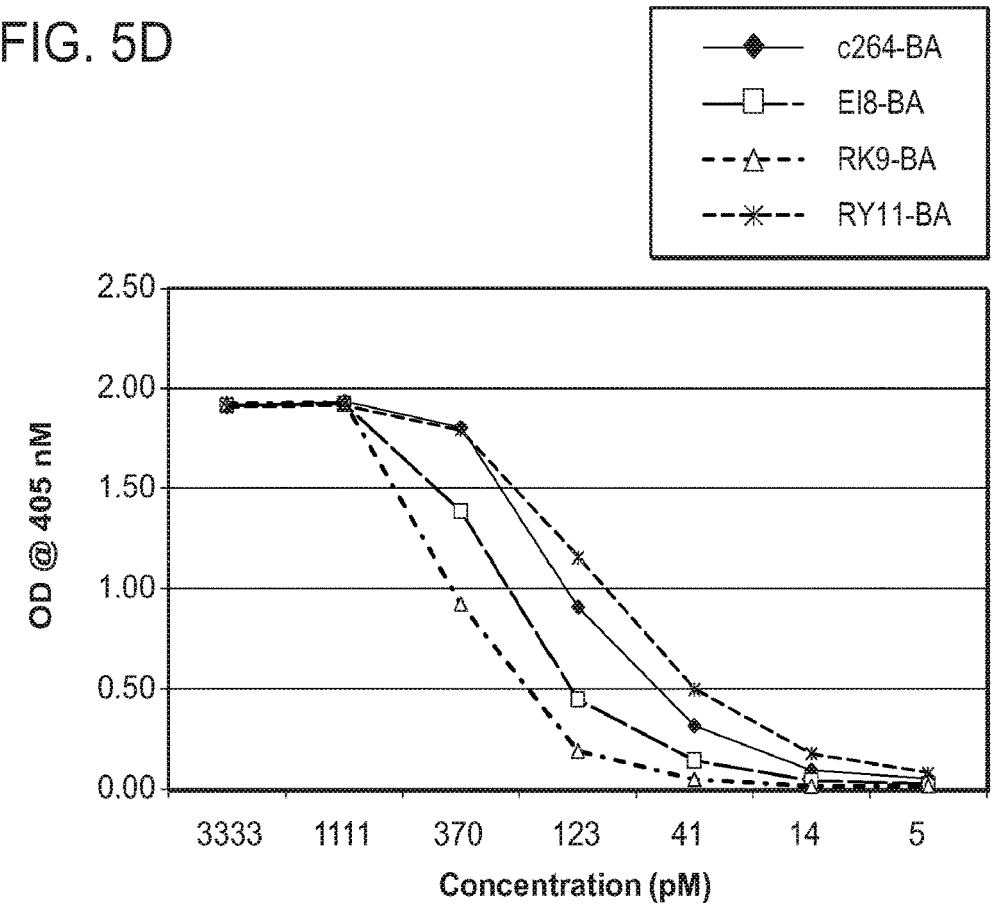
Figure 6A:
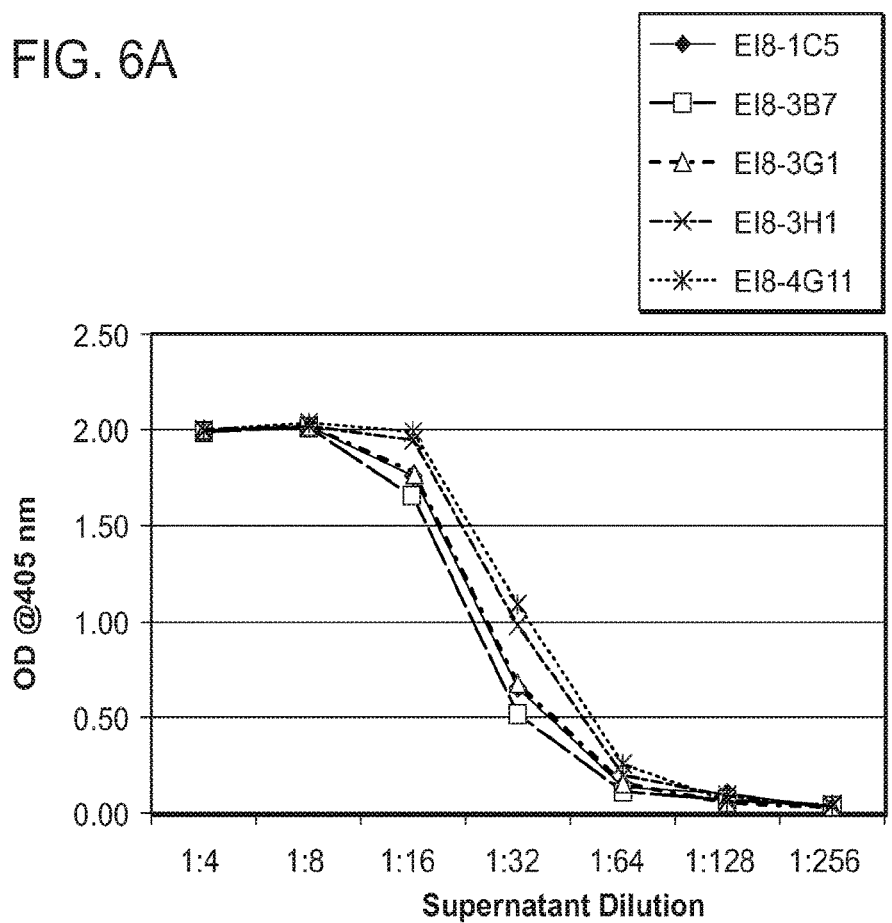
FIGS. 6A-6F demonstrate that scTCR proteins binding specifically to HIV peptide/HLA complexes. Results for E18 are shown in FIG. 6A; results for ISP-R are shown in FIG. 6B; results for QW9-AV24 are shown in FIG. 6C; results for FL8 are shown in FIG. 6D; results for RK9 and RY11 are shown in FIG. 6E; and results for A24RF10 are shown in FIG. 6F.
Figure 6B:
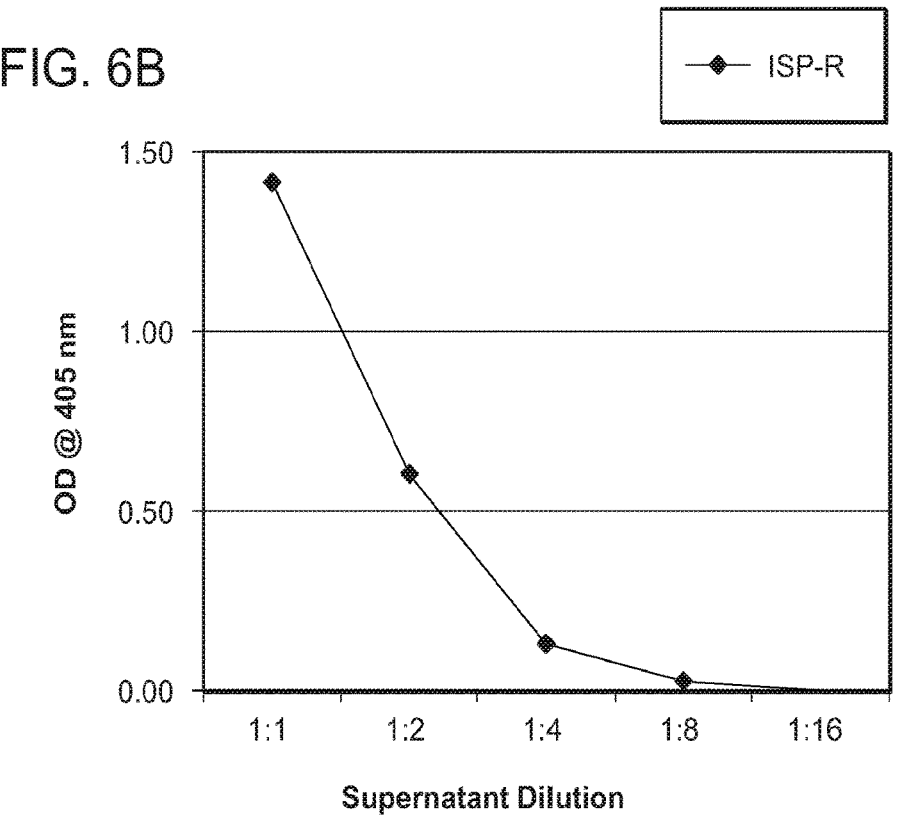
Figure 6C:
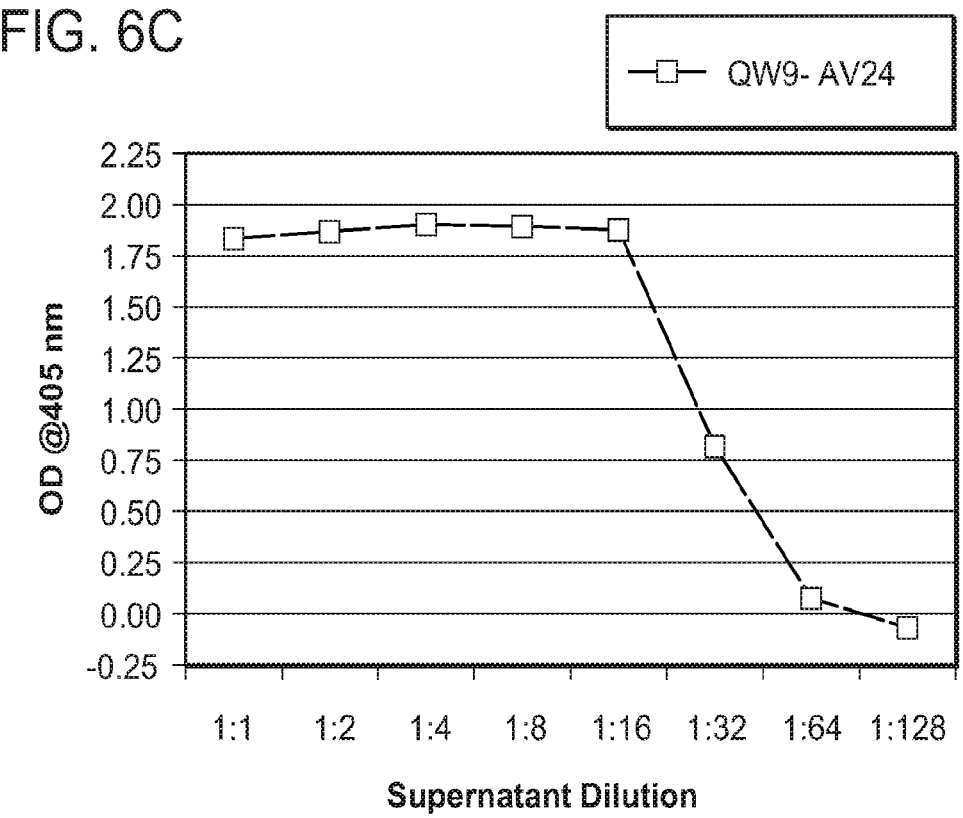
Figure 6D:
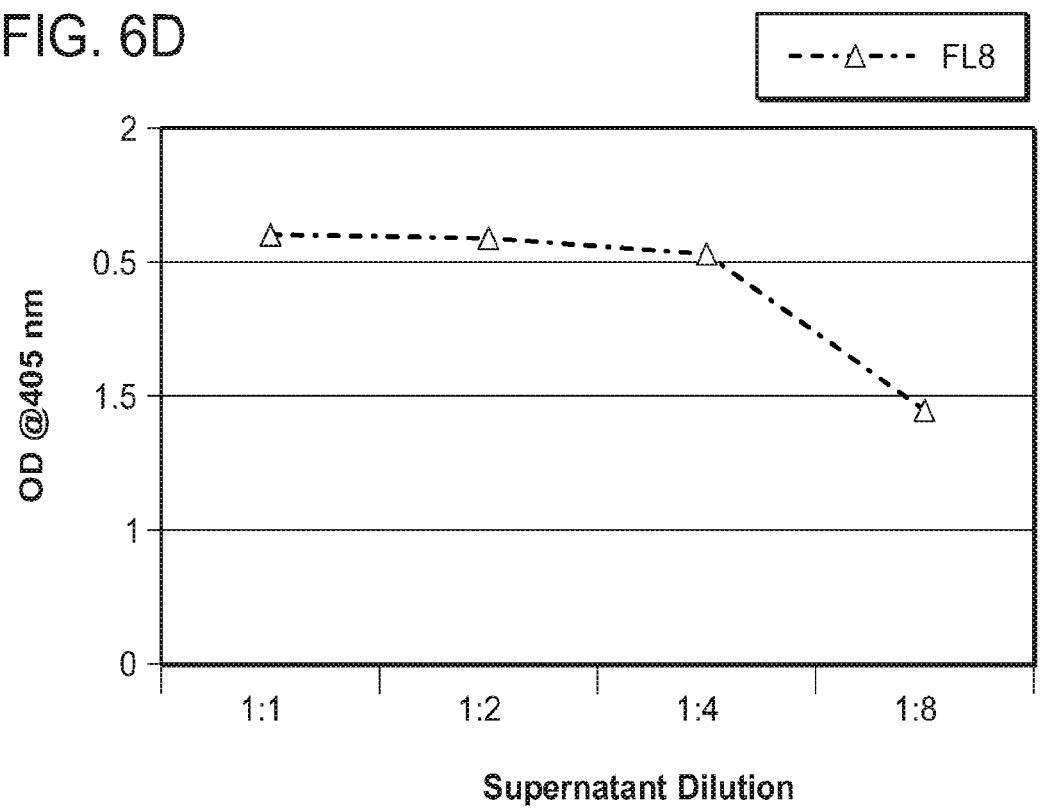
Figure 6E:
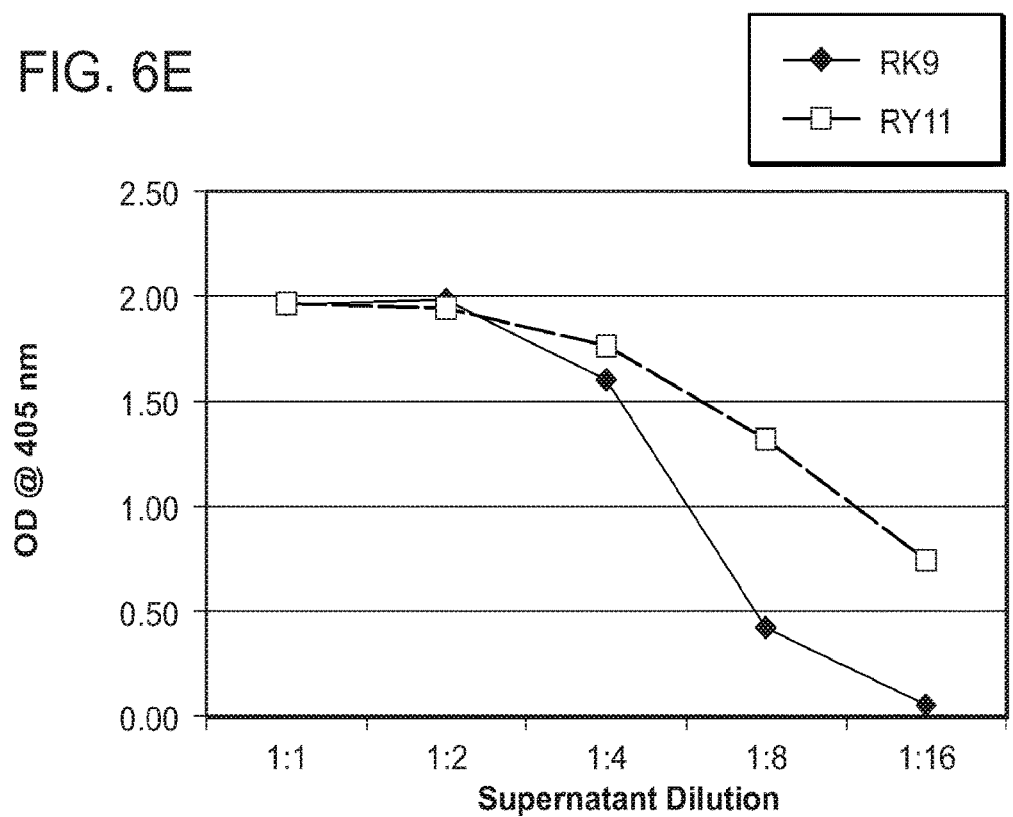
Figure 6F:
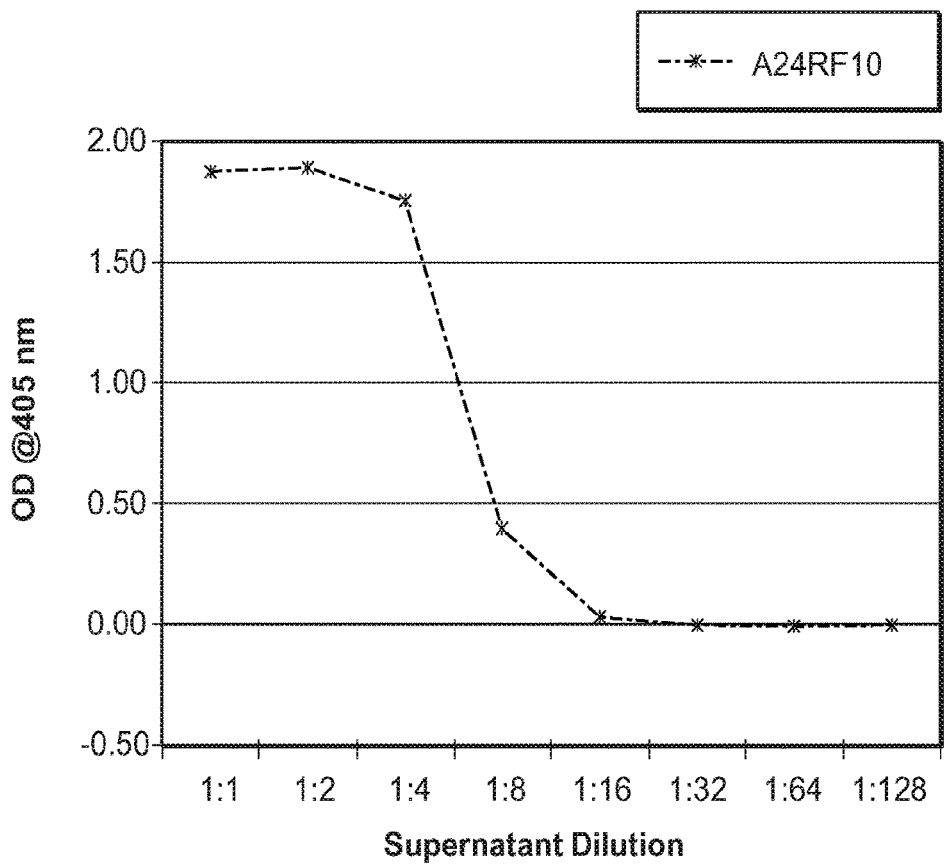
Figure 7A:
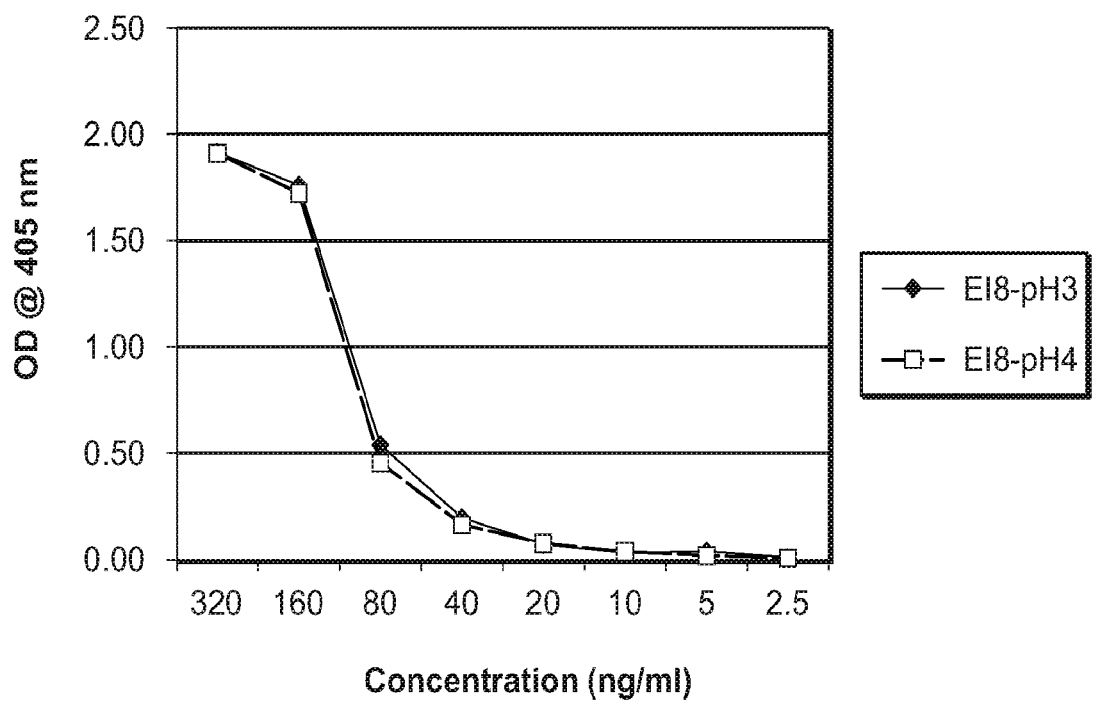
FIGS. 7A-7D demonstrate that the binding activity in FIGS. 6A-6F was confirmed with affinity purified scTCR-BirA. Results for E18 are shown in FIG. 7A; results for ISP are shown in FIG. 7B; results for QW9 are shown in FIG. 7C; and results for RK9 and RY11 are shown in FIG. 7D.
Figure 7B:
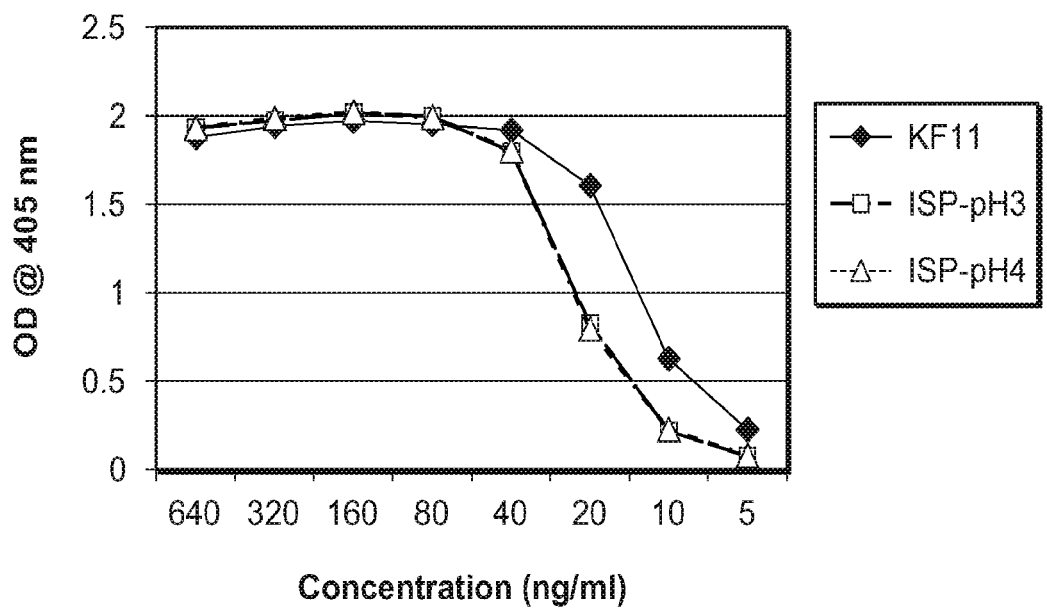
Figure 7C:
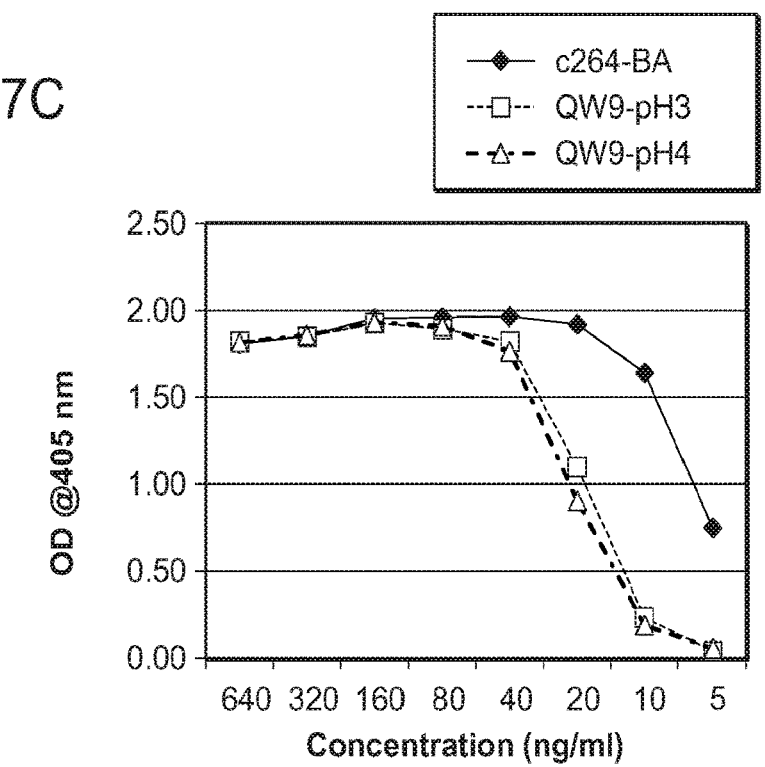
Figure 7D:
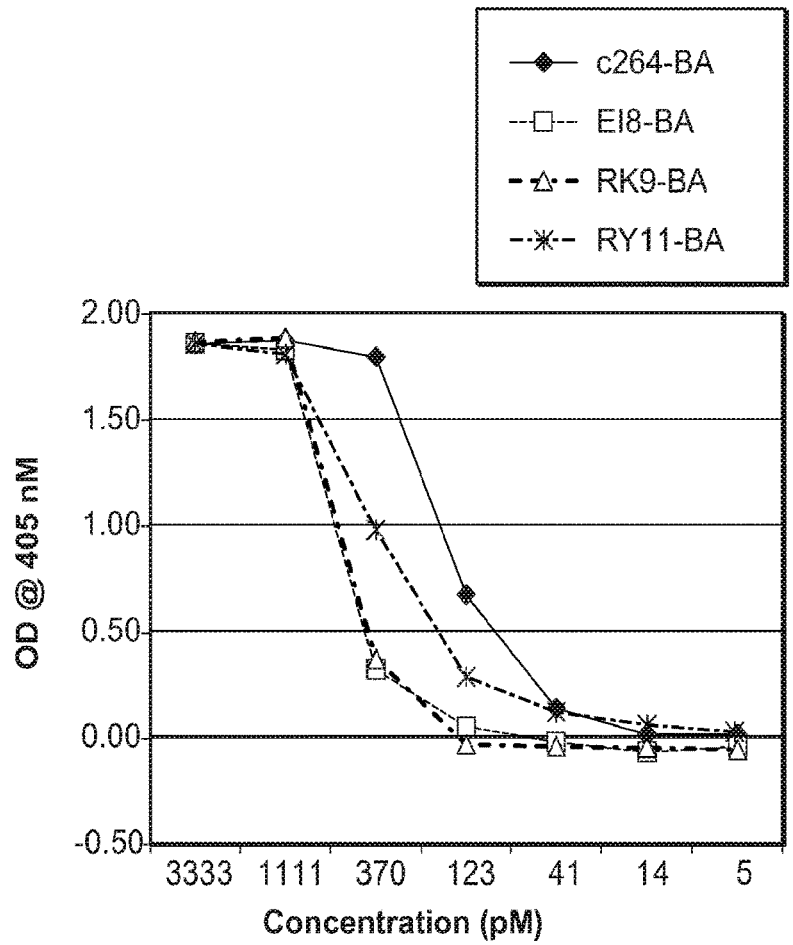

PCR products of α and β TCR gene cDNA were cloned into pGEM T-easy vector for sequence verification. The TCR variable region of a gene and both TCR variable and extracellular constant regions of β gene were PCR-amplified from the pGEM T-easy vectors using specific primers and subcloned into the pMSGV expression vector with $(G_4S)_3$ linker located between the TCR Vα region and TCR Vβ-Cβ regions. A BirA tag sequence was fused at the end of TCR Cβ for site specific biotinylation and TCR multiplexing with fluor-labeled streptavidin (SA). The format of the single-chain TCR (scTCR) construct is depicted in FIG. 2. The pMSGV vector has sequences (i.e., enhancer, promoter, transcription and translational start/stop sequences and poly A signal regions) for appropriate expression of the scTCR gene and to direct secretion of the soluble scTCR protein.

The scTCR-BirA sequences were cloned into expression vectors as described previously (U.S. Pat. No. 8,507,222, incorporated herein by reference), and the expression vectors transfected into CHO cells. Transfected CHO cells secreted soluble scTCR-BirA fusion proteins, which were detected with ELISA using TCR specific antibodies. Transfected CHO cells were subcloned to generate production cell lines. Soluble scTCR-BirA fusion proteins were purified from culture supernatant using affinity chromatography with an anti-human TCR Cβ antibody (BF-1 mAb).

Clonal CHO cell transfectants carrying vectors expressing B08E18, B57ISP, B57QW9, BO8FL8, A24RF10, or B35RY11 scTCR-BirA fusion proteins were selected and cultured. The different scTCR-BirA proteins were secreted into the culture supernatant and measured using an ELISA comprising anti-TCR Cβ chain Ab (BF1) (capture) and biotinylated anti-TCR Cβ Ab (W4F) (probe). Multiple clones expressed B08E18, B57ISP, B57QW9, B08FL8, A24RF10, RK9, or B35RY11 scTCR-BirA fusion proteins (FIGS. 3A-3F). Additionally, scTCR-BirA proteins were purified from the culture media by BF-1 Ab affinity purification following elution with buffer at pH 4 or subsequently with buffer at pH 3. The different affinity-purified scTCR-BirA proteins were analyzed by reduced SDS PAGE and found to comprise primarily a single protein band of the expected molecular mass (FIGS. 4A-4D). The purified scTCR-BirA proteins also showed reactivity in the TCR specific ELISA (FIGS. 5A-5D).

In some cases, the scTCR-BirA proteins were biotinylated. Biotinylated proteins were conjugated with streptavidin to form a multimeric complex. Additionally, other HIV-specific TCR constructs described above were used to generate expression vectors and CHO transfectants. The resulting HIV-specific TCR proteins were produced and purified with similar results as shown for the B08E18, B57ISP, B57QW9, B08FL8, A24RF10 or B35RY11 scTCR constructs.

Additional constructs can be generated to express HIV-specific scTCR fusion proteins comprising immune effector domains including but not limited to cytokines (i.e., IL-2, IL-15, IL-7, IL-21, IFNγ, IFNα), IgG Fc, or antibody domains specific to disease targets or checkpoint inhibitors. The constructs comprising the variable domains or CDR regions of the TCRs described above could also be generated to express heterodimeric TCRs that are soluble or expressed on the cell surface, including molecules that further comprise immune signaling domains such as the TCR or CD (i.e., CD3 or CD28) transmembrane/cytoplasmic domains.

Example 2: Antigen recognition activity of HIV-specific TCRs. To verify scTCR-BirA binding activities to their cognate peptide/HLA complexes, ELISA-based methods used labelled peptide/HLA tetramers as probes. ELISA plate wells were coated with anti-TCR Cβ chain Ab (BF1). The scTCR-BirA protein was added, followed by incubation and wash steps. Peptide/HLA tetramers labeled with horse radish peroxidase (HRP) were added. Following additional wash steps, HRP substrate was added. FIGS. 6A-6F show specific binding to HIV peptide/HLA complexes with scTCR proteins secreted in CHO transfectant supernatant. Binding activity was confirmed with affinity purified scTCR-BirA protein (FIGS. 7A-7D). Similar results were obtained with other HIV specific scTCR constructs described above.

Figure 8A:
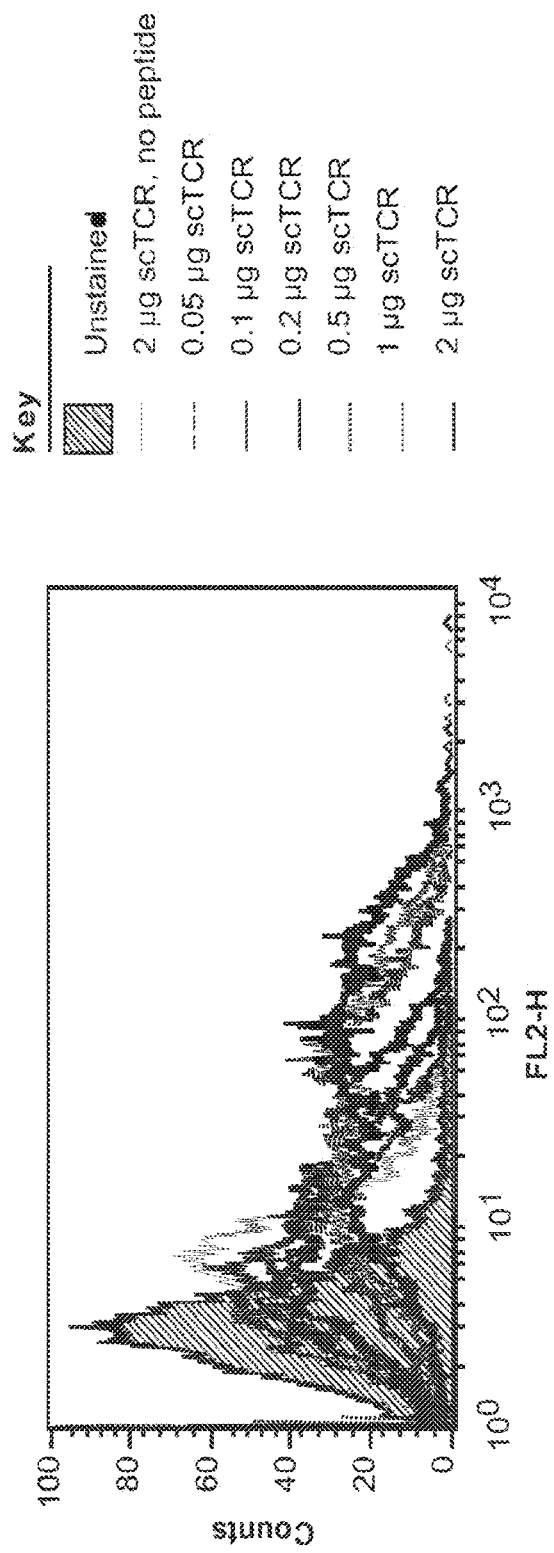
FIGS. 8A & 8B demonstrate that B08EI8 scTCR tetramer binding to HIV EI8 loaded HLA-B8 molecules depends on both the amount of loaded peptide and scTCR used.
Figure 8B:
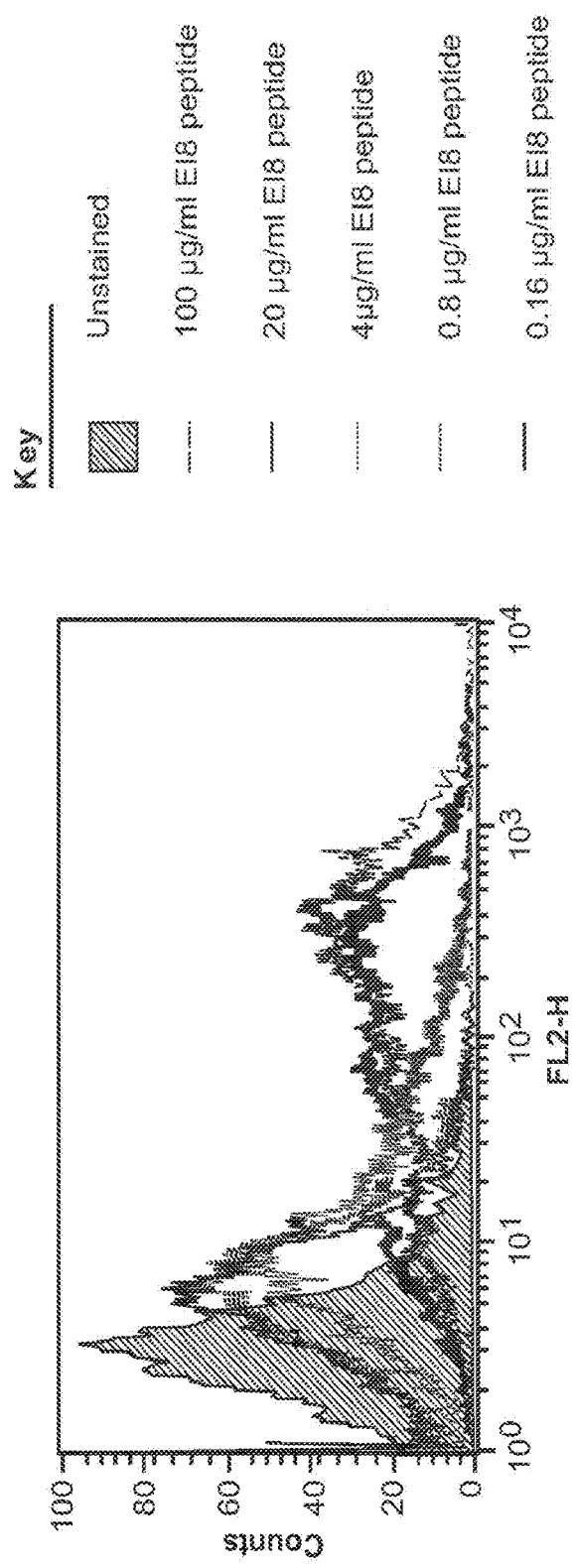
Figure 9A:
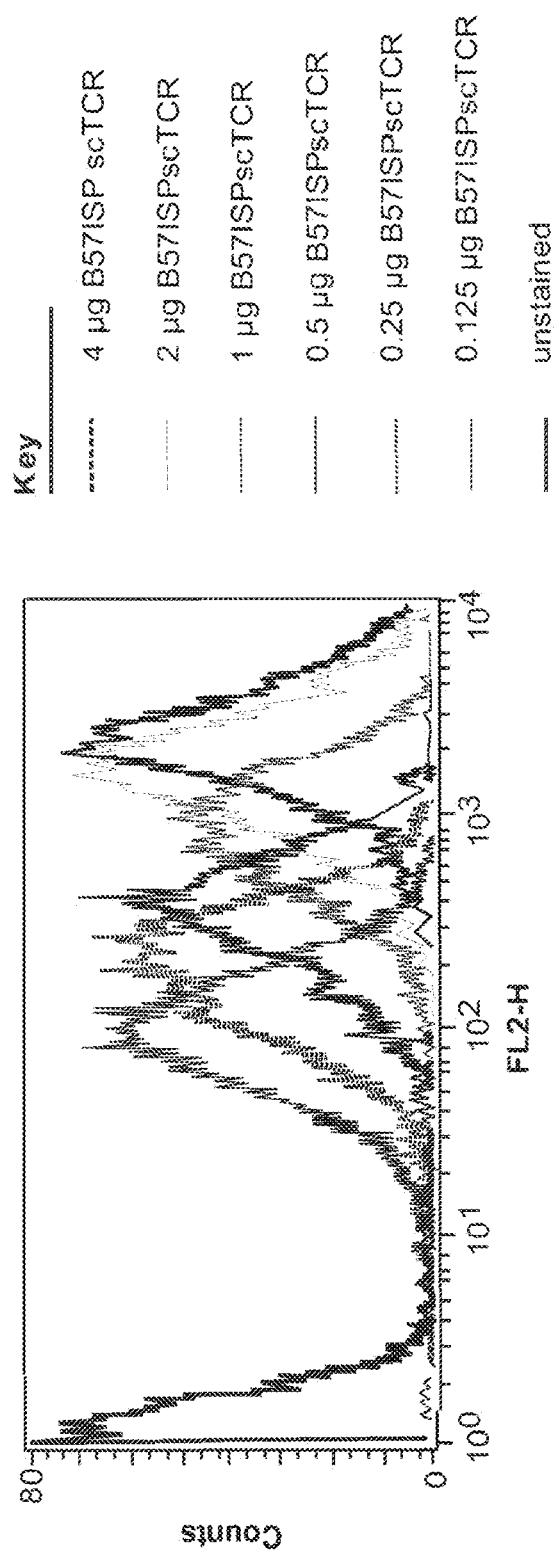
FIGS. 9A-9C demonstrate that similar results were observed with the B57ISP scTCR FIG. 9A (0.125 μg to 4 μg), FIG. 9B (20 μg/ml to 200 μg/ml)), A03RK9 scTCR (FIG. 9C) and other HIV-specific TCRs. GVA2 cells were loaded with peptides (100 μg/MI, 37° C. for 4 hours) with or without PLE. Detection with 2 μg scTCR-PE.
Figure 9B:
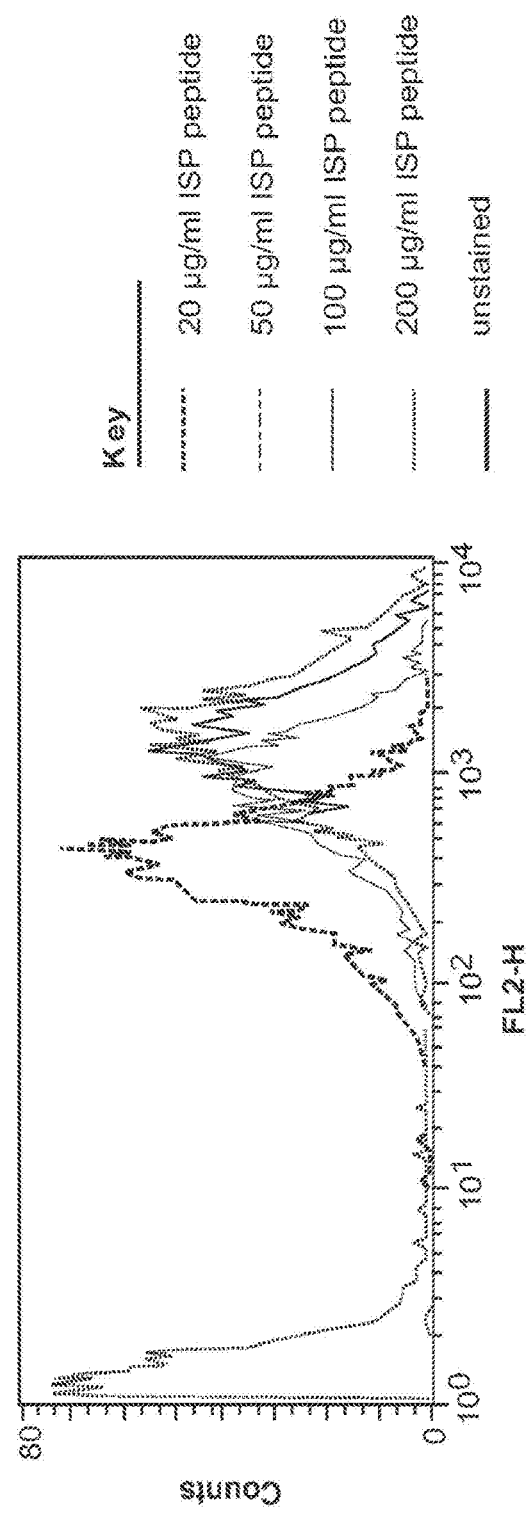
Figure 9C:
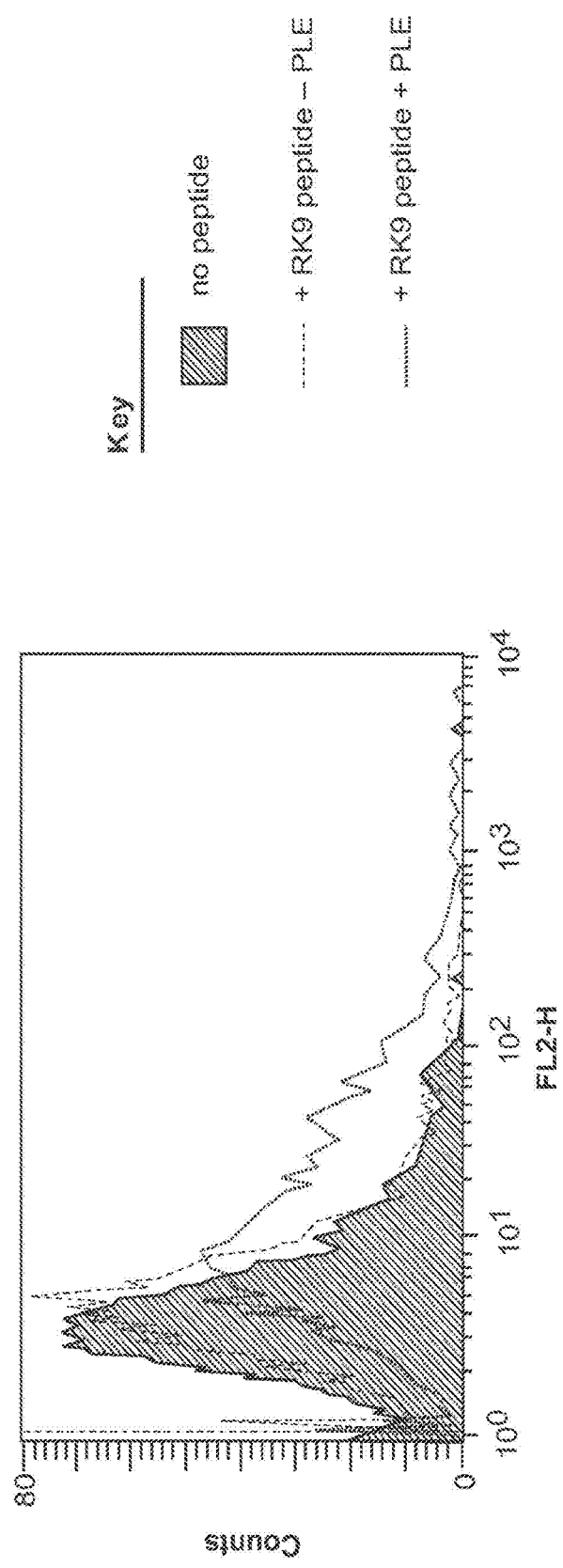

HIV-specific scTCR binding to peptide/HLA complexes on cell surfaces was assessed by flow cytometry. EBV-transformed human B cell lines expressing appropriate HLA molecules were loaded with cognate HIV peptides. Biotinylated scTCR-BirA fusions were multimerized with PE-conjugated streptavidin (SA-PE) as staining reagents. The peptide-loaded B cells were incubated with scTCR:SA-PE multimers and, following wash steps, binding was determined by flow cytometry. FIGS. 8A & 8B show binding of B08E18 scTCR tetramer to HIV EI8 peptide loaded HLA-B8 molecules depended on both the amount of loaded peptide and scTCR protein used. Similar results were observed with the B57ISP scTCR (FIGS. 9A & 9B), A03RK9 scTCR (FIG. 9C) and other HIV-specific TCRs. These results indicate that genes encoding HIV specific TCRs can be isolated from T cells of HIV infected individuals and such TCR genes can be expressed as novel TCR fusion proteins that retain the ability to bind HIV peptide/HLA complexes.

Figure 10:
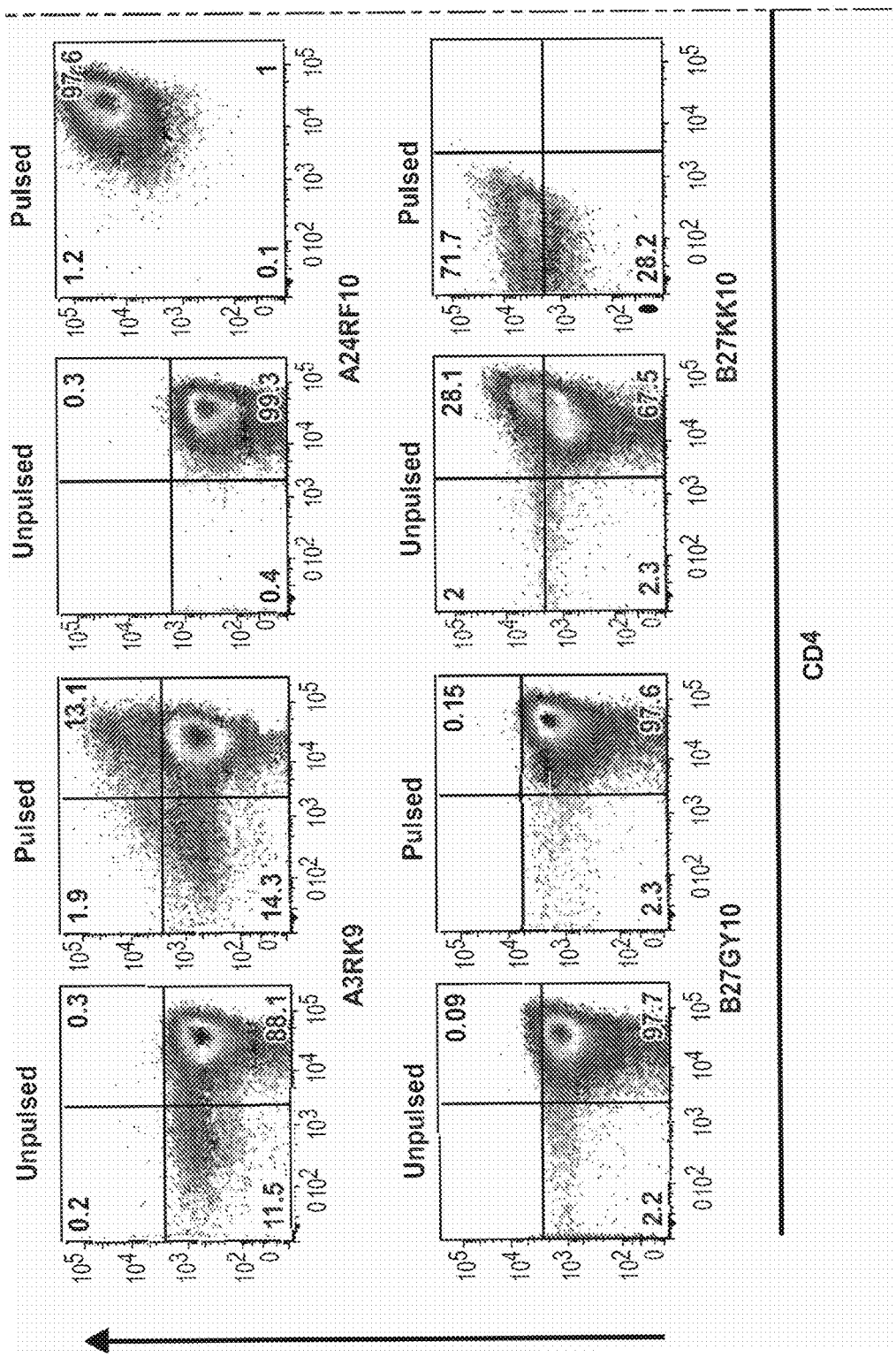
FIG. 10 is a series of density plots of scTCR multimers staining CD4+ T cells unpulsed (left) or loaded (pulsed) (right) with specific peptides. TCR names are given below each pair of plots. The first part of each name represents the HLA locus and allele. The second part of the name is the first and last amino acid in the peptide sequence (except for ISP, which is the first 3 amino acids), followed by a peptide length. See Table 1 for more details. HLA-A3-RK9 (p17) is labeled as A3RK9; HLA-A24-RF10 (Nef) is labeled as A24RF10; HLA-B8-EI8 (p24) is labeled as B8EI8; HLA-B8-FL8 (Nef) is labeled as B8FL8; HLA-B14-DA9 (p24) is labeled as B14DA9; HLA-B27-GY10 is labeled as B27GY10; HLA-B27-KK10 (p24) is labeled as B27KK10; HLA-B35-RY11 (Nef) is labeled as B35RY11; HLA-B57-QW9 (p24) is labeled as B57QW9; and HLA-B57-ISP (p24) is labeled as B57ISP.
Figure 10:
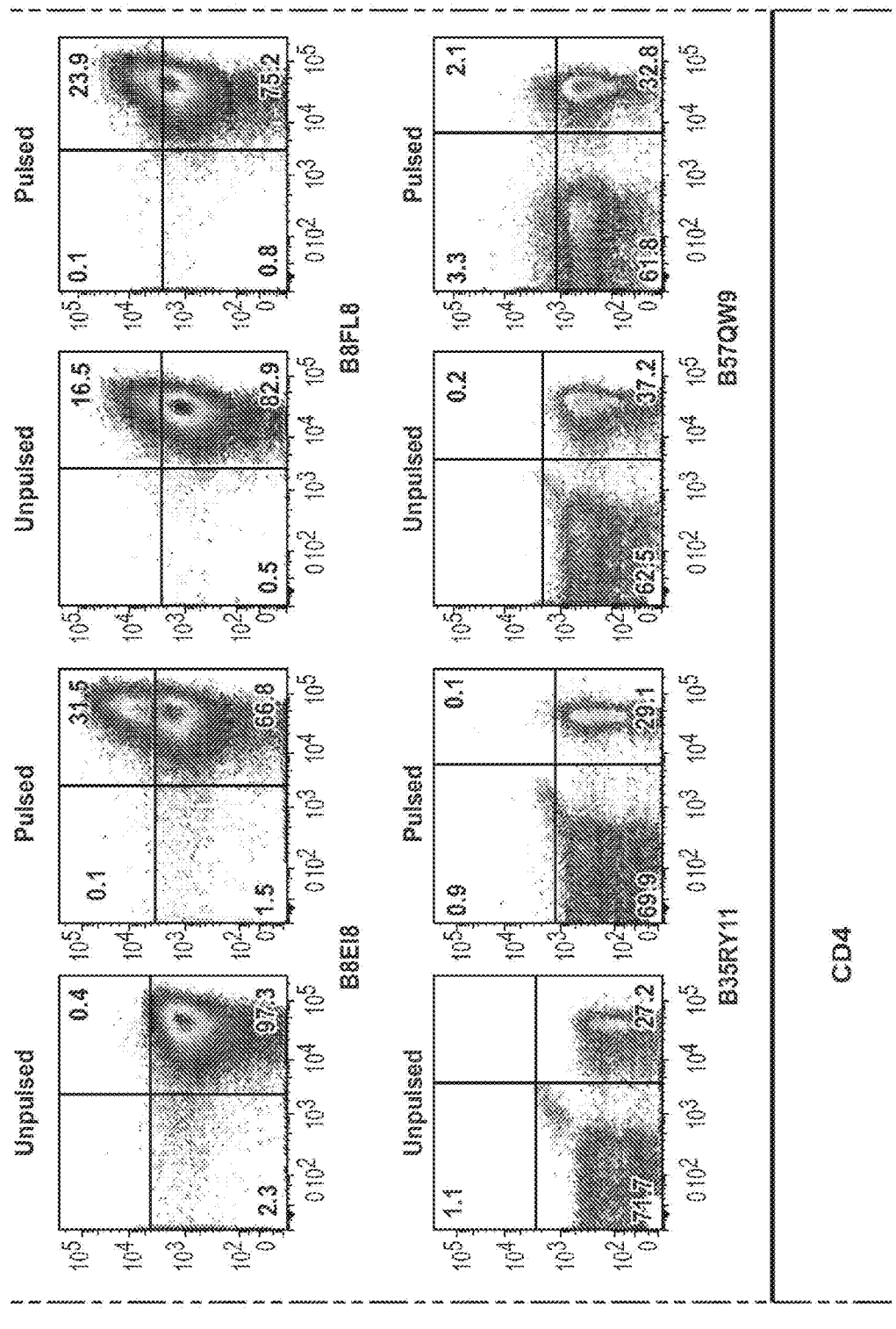
Figure 10:
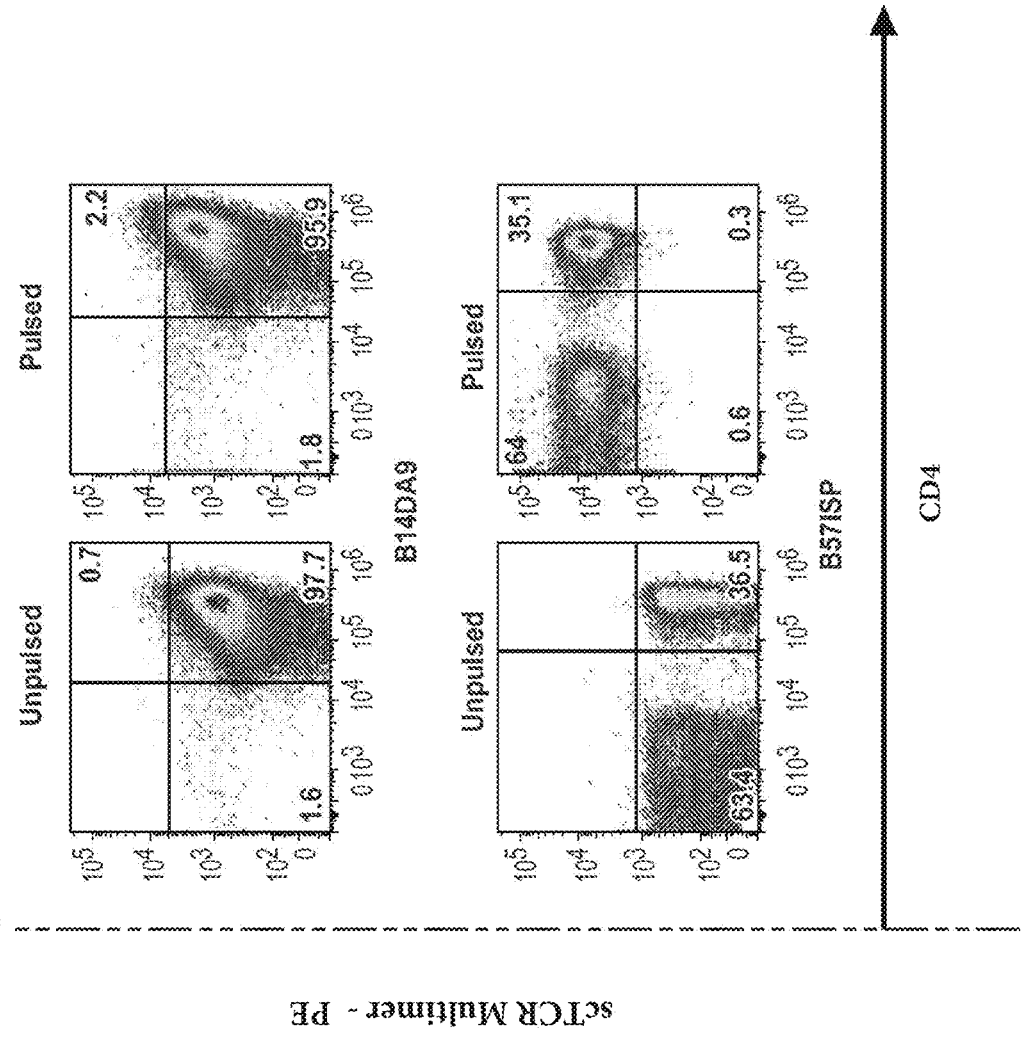

Example 3: Reactivity of HIV-specific TCRs against peptide-loaded and HIV-infected human CD4$^+$ T cells. CD4$^+$ T cells were isolated from the human PBMCs and loaded with specific HIV peptides as described above for EBV-transformed human B cells. The binding of purified scTCR:SA-PE multimers was then assessed as described in Example 2 (FIG. 10). A3RK9, A24RF10, B8EI8, B8FL8, B27KK10, and B57ISP multimers showed strong binding. B14DA9, B35RY11, and B57QW9 multimers showed less intense staining to the peptide-loaded ("pulsed") cells compared to unpulsed cells. These scTCR multimers are capable of detecting their cognate HIV peptide/HLA complexes presented on human CD4+ T cell surfaces.

Figure 11:
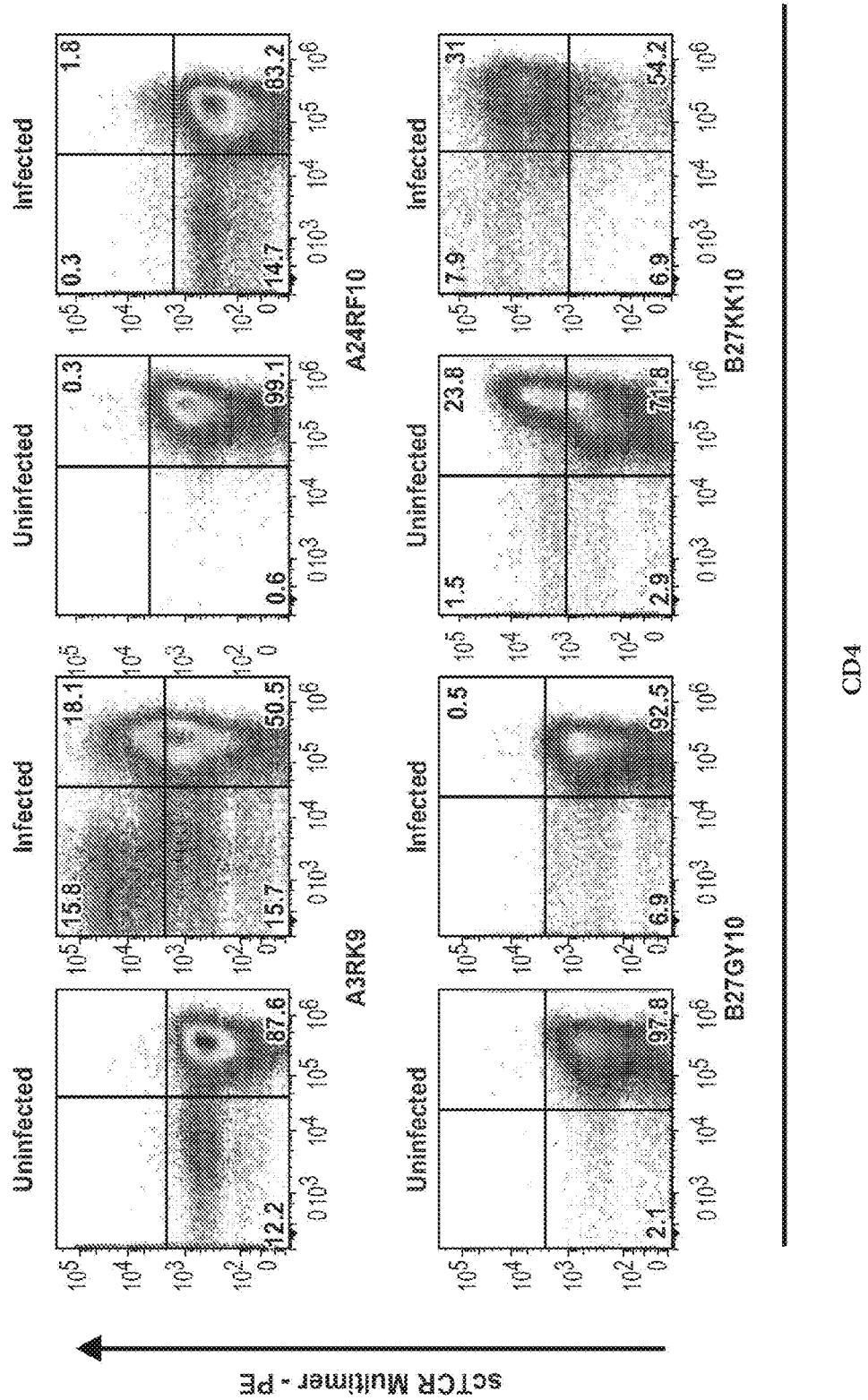
FIG. 11 is a series of density plots of scTCR multimers staining HIV-infected CD4+ T cells. TCR names are given below each pair of plots that represent uninfected and infected autologous target cells. The first part of each name represents the HLA locus and allele. The second part of the name is the first and last amino acid in the peptide sequence (except for ISP, which is the first 3 amino acids), followed by a peptide length. See Table 1 for more details. HLA-A3-RK9 (p17) is labeled as A3RK9; HLA-A24-RF10 (Nef) is labeled as A24RF10; HLA-B8-EI8 (p24) is labeled as B8EI8; HLA-B8-FL8 (Nef) is labeled as B8FL8; HLA-B14-DA9 (p24) is labeled as B14DA9; HLA-B27-GY10 is labeled as B27GY10; HLA-B27-KK10 (p24) is labeled as B27KK10; HLA-B35-RY11 (Nef) is labeled as B35RY11; HLA-B57-QW9 (p24) is labeled as B57QW9; and HLA-B57-ISP (p24) is labeled as B57ISP.
Figure 11:
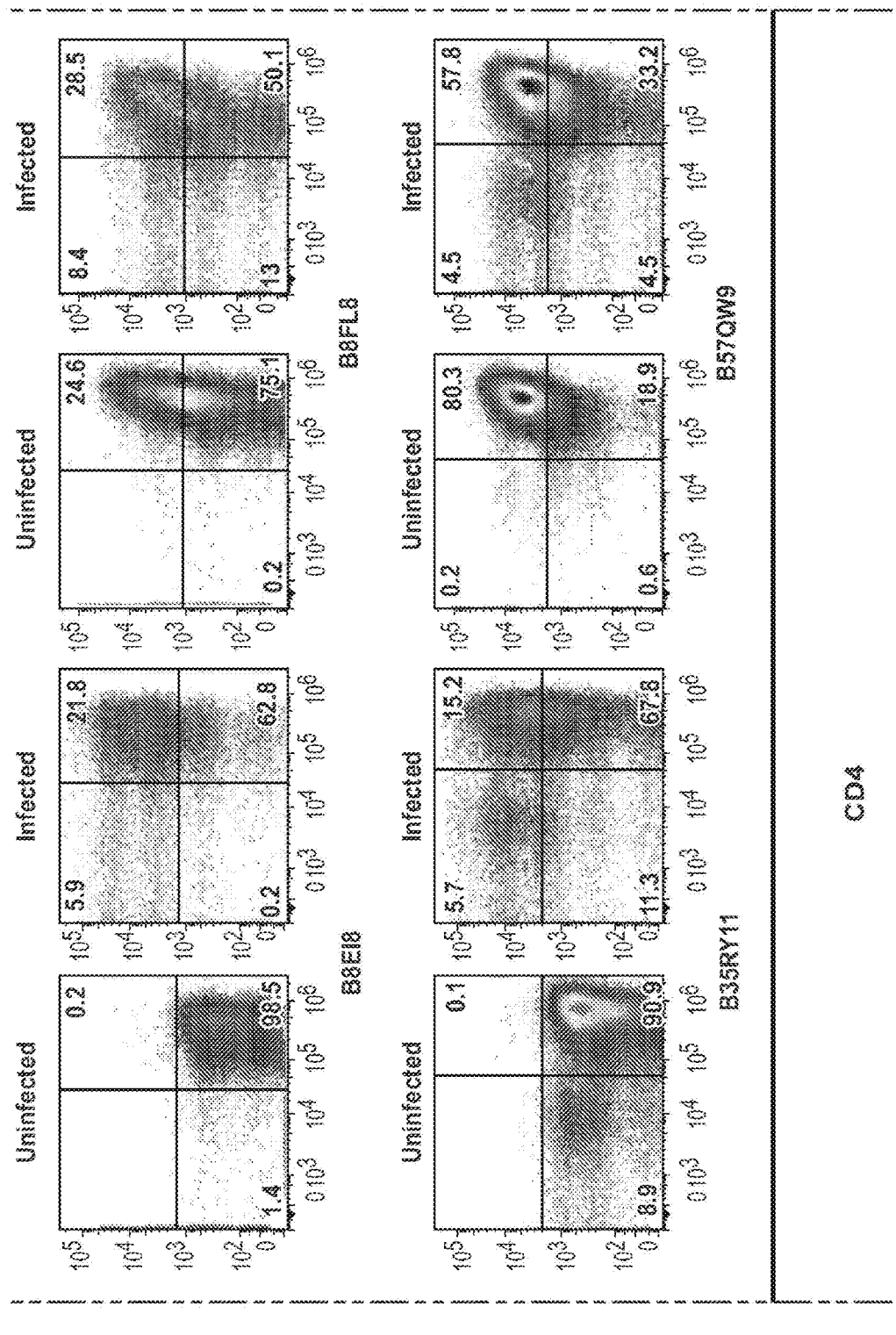
Figure 11:
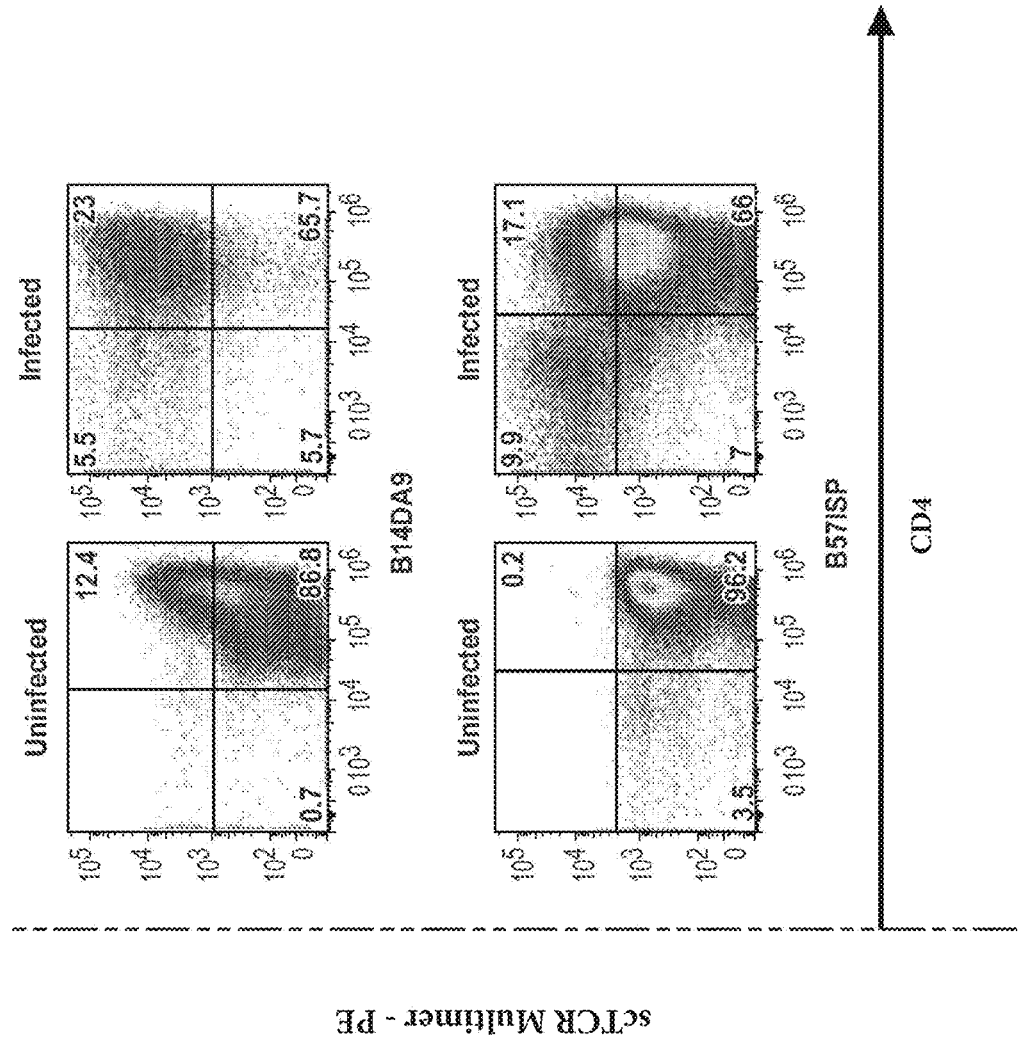

Isolated human CD4$^+$ T cells from volunteers were infected with the HIV-1 in vitro and then stained with anti-CD4 mAb and scTCR multimers. HIV-1 infectivity was confirmed by staining with a p24 mAb (data not shown). FIG. 11 shows the visualization of HIV peptide/HLA complexes on the surface of infected CD4$^+$ T cells stained with scTCR multimers. Uninfected and HIV-infected CD4$^+$ T-cells were stained with anti-CD4 mAb and various scTCR multimers. CD4 is down-regulated during the late phase of HIV infection, hence the anti-CD4 Ab stained T cells population shifts left after infection. The scTCR multimers specific for A3RK9, B8EI8, B8FL8, B14DA9, B27KK10, B35RY11, and B57ISP stained their HIV peptide/HLA targets very effectively. Although the scTCR multimers specific for A24RF10 had the best staining for pulsed cells, there is very little staining of the HIV-1 infected targets. This suggests minimal RF10 presentation in HLA-A24 following HIV infection. Conversely, there appeared to be very little staining of RY11 peptide loaded cells with the scTCR multimers specific for B35RY11. However, HIV-1 infected cells showed good staining with the B35RY11 scTCR multimer. This suggests that internal processing is more efficient than external peptide loading for the RY11 peptide. These results demonstrate the advantage of the scTCR proteins in detecting and targeting HIV peptide/HLA complexes on HIV infected cells.

OTHER EMBODIMENTS

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While the technologies disclosed herein have been particularly shown and described with references to preferred embodiments thereof, it will be understood by those skilled in the art that various changes in form and details may be made therein without departing from the scope of the invention encompassed by the appended claims.

What is claimed:

1. A polypeptide comprising a single chain T cell receptor (scTCR) comprising a variable alpha (Vα) domain, a variable beta domain (Vβ) and a constant region domain (C), wherein the Vα and Vβ domains each have at least 85% sequence identity to a scTCR selected from the group consisting of SEQ ID Nos: 2, 4, 6, 8, 10, 12, 14, 16, and 18, and wherein the complementarity determining regions (CDRs) of the Vα domain each have 100% identity to the Vα CDRs of the scTCR, and wherein the CDRs of the VB domain each have 100% identity to the Vβ CDRs of the scTCR.

2. The polypeptide of claim 1, wherein the polypeptide has at least 90% sequence identity to SEQ ID NO: 2.

3. The polypeptide of claim 2, wherein the polypeptide has 100% sequence identity to SEQ ID NO: 2.

4. The polypeptide of claim 1, further comprising a CD3 signaling domain or a CD28 signaling domain.

5. A polynucleotide, wherein the nucleic acid sequence encodes the polypeptide of claim 1.

6. The polynucleotide of claim 5, wherein the nucleic acid sequence is selected from the group consisting of SEQ ID NOs: 1, 3, 5, 7, 9, 11, 13, 15, and 17.

7. The polynucleotide of claim 5, further comprising a nucleic acid sequence encoding an immune signaling domain, a transmembrane domain, a cytoplasmic domain, a biologically active domain, or a combination thereof.

8. The polynucleotide of claim 7, wherein the biologically active domain is selected from the group consisting of a cytokine, a checkpoint inhibitor, an antigen specific antibody domain, an enzyme, and a combination thereof.

9. An isolated cell comprising a polynucleotide according to claim 5.

10. The isolated cell of claim 9, wherein the isolated cell is an autologous cell.

11. A method of targeting a staining or therapeutic agent to an HIV infected cell in a subject in need thereof, the method comprising administering to the subject an effective amount of a staining or therapeutic agent, wherein the staining or therapeutic agent comprises the scTCR of claim 1.

* * * * *